(12) United States Patent
Padkjaer et al.

(10) Patent No.: US 9,908,944 B2
(45) Date of Patent: Mar. 6, 2018

(54) ANTIBODIES THAT BIND UROKINASE PLASMINOGEN ACTIVATOR

(71) Applicant: Novo Nordisk A/S, Bagsvaerd (DK)

(72) Inventors: Soeren Padkjaer, Vaerloese (DK); Jesper Pass, Alleroed (DK); Gustav Roeder, Frederikssund (DK); Kasper Almholt, Greve (DK); Pernille A. Usher, Vanloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/905,409

(22) PCT Filed: Jul. 15, 2014

(86) PCT No.: PCT/EP2014/065136
§ 371 (c)(1),
(2) Date: Jan. 15, 2016

(87) PCT Pub. No.: WO2015/007727
PCT Pub. Date: Jan. 22, 2015

(65) Prior Publication Data
US 2016/0159924 A1  Jun. 9, 2016

Related U.S. Application Data

(60) Provisional application No. 61/847,664, filed on Jul. 18, 2013.

(51) Int. Cl.
*C07K 16/40* (2006.01)
*G01N 33/68* (2006.01)

(52) U.S. Cl.
CPC ......... *C07K 16/40* (2013.01); *G01N 33/6854* (2013.01); *C07K 2317/24* (2013.01); *C07K 2317/34* (2013.01); *C07K 2317/51* (2013.01); *C07K 2317/515* (2013.01); *C07K 2317/565* (2013.01); *C07K 2317/76* (2013.01); *C07K 2317/92* (2013.01); *G01N 2333/9723* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 5,453,269 | A | 9/1995 | Haber et al. |
| 5,496,549 | A | 3/1996 | Yamazaki et al. |
| 8,062,637 | B2 | 11/2011 | Hamilton et al. |

FOREIGN PATENT DOCUMENTS

| | | |
|---|---|---|
| WO | 03/033009 A2 | 4/2003 |
| WO | 2005/048822 A2 | 6/2005 |
| WO | 2006/050177 A2 | 5/2006 |

OTHER PUBLICATIONS

Blouse et al., J. Biol. Chem. 284, 4647-4657, 2009.*
Mariuzza et al., The structural basis of antigen-antibody recognition, Ann. Rev. Biophys. Chem. 16, 139-59, 1987.*
Kenneth A. Botkjaer et al. "Targeting the Autolysis Loop of Urokinase-Type Plasminogen Activator With Conformation-Specific Monoclonal Antibodies" Biochemical Journal. 2011 vol. 438(1) pp. 39-51.
Grant E Blouse et al. "A Novel Mode of Intervention With Serine Protease Activity Targeting Zymogen Activation" The Journal of Biological Chemistry. 2009 vol. 284(7) pp. 4647-4657.
P.A. Andreasen et al. "The plasminogen activation system in tumor growth, invasion, and metastasis" Cellular and Molecular Life Sciences. 2000 vol. 57(1) pp. 25-40.
Andrew D. Cook et al. "Differing Roles for Urokinase and Tissue-Type Plasminogen Activator in Collagen-Induced Arthritis" American Journal of Pathology. 2002 vol. 160(3) pp. 917-926.
Jinan Li et al. "The Plasminogen Activator/Plasmin System Is Essential for Development of the Joint Inflammatory Phase of Collagen Type II-Induced Arthritis" American Journal of Pathology. 2005 vol. 166(3) pp. 783-792.
Andrew D. Cook et al. "Urokinase-type plasminogen activator and arthritis progression: role in systemic disease with immune complex involvement" Arthritis Research and Therapy. 2010 vol. 12: R37 pp. 1-13.
Christine M DeNardo et al. "Urokinase-type plasminogen activator and arthritis progression: contrasting roles in systemic and monoarticular arthritis models" Arthritis Research and Therapy. 2010 vol. 12:R199 pp. 1-12.
Ida K. Lund et al. "Antibody-mediated Targeting of the Urokinase-type Plasminogen Activator Proteolytic Function Neutralizes Fibrinolysis in Vivo" The Journal of Biological Chemistry. 2008. vol. 283(47) pp. 32506-32515.
Del Rosso, M. et al. "The urokinase-type plasminogen activator system and inflammatory joint diseases" Clinical and Experimental Rheumatology. 1999 vol. 17(4) pp. 485-498.
Jiang et al. "Rezymogenation of active urokinase induced by an inhibitory antibody" The Biochemical Journal. 2013 vol. 449(1) pp. 161-166.

* cited by examiner

*Primary Examiner* — Elly-Gerald Stoica
(74) *Attorney, Agent, or Firm* — Jianjie Hu

(57) ABSTRACT

The present invention relates to a method of identifying urokinase plasminogen activator (uPA) antibodies. The invention also relates to antibodies that are capable of binding uPA and which are capable of reducing or inhibiting uPA activity. Furthermore, the invention relates to uses for such antibodies, such as therapeutic and pharmaceutical uses.

3 Claims, 9 Drawing Sheets

SEQ ID NO: 7 - 0266-0000-0010VH
DVKLVESGGGLVKPGGSLKLSCVASGFTFSSYTMSWVRQTPEKRLEWVATISGGGSHIYYA
DSVKGRFTISRDNAKNTLYLQMSSLKSEDTAIYYCTRDGRDGSWFAYWGQGTLVTVSA

SEQ ID NO: 8 - 0266-0000-0010VL
DIVMTQSPATLSVTPGDRVSLSCRTSQSIGDYLHWYQQKSHESPRLLIKYVSQSISGIPS
RFSGSGSGSDFTLSINSVESEDVGVYYCQNSHSFPLTFGSGTKLELK

SEQ ID NO: 9 - CDR_H1
SYTMS

SEQ ID NO: 10 - CDR_H2
TISGGGSHIYYADSVKG

SEQ ID NO: 11 - CDR_H3
DGRDGSWFAY

SEQ ID NO: 12 - CDR_L1
RTSQSIGDYLH

SEQ ID NO: 13 - CDR_L2
YVSQSIS

SEQ ID NO: 14 - CDR_L3
QNSHSFPLT

SEQ ID NO: 15 - VH3_21/JH4
EVQLVESGGGLVKPGGSLRLSCAASGFTFSSYSMNWVRQAPGKGLEWVSSISSSSSYIYYA
DSVKGRFTISRDNAKNSLYLQMNSLRAEDTAVYYCAR/YFDYWGQGTLVTVSS

SEQ ID NO: 16 - V6D_41/JK4
DVVMTQSPAFLSVTPGEKVTITCQASEGIGNYLYWYQQKPDQAPKLLIKYASQSISGVPS
RFSGSGSGTDFTFTISSLEAEDAATYYCQQGNKHP/LTFGGGTKVEIK

SEQ ID NO: 17 - hz0266-0000-0010VH
EVQLVESGGGLVKPGGSLRLSCAASGFTFSSYTMSWVRQAPGKGLEWVSTISGGGSHIYYA
DSVKGRFTISRDNAKNSLYLQMNSLRAEDTAVYYCARDGRDGSWFAYWGQGTLVTVSS

SEQ ID NO: 18 - hz0266-0000-0010VL
DVVMTQSPAFLSVTPGEKVTITCRTSQSIGDYLHWYQQKPDQSPKLLIKYVSQSISGVPS
RFSGSGSGTDFTFTISSLEAEDAATYYCQNSHSFPLTFGGGTKVEIK

Figure 2

SEQUENCE LISTING

<160> NUMBER OF SEQ ID NOS: 26

<210> SEQ ID NO 1
<211> LENGTH: 411
<212> TYPE: PRT
<213> ORGANISM: Homo sapiens

<400> SEQUENCE: 1

```
Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Phe Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
            115                 120                 125

His Asp Cys Ala Asp Gly Lys Lys Pro Ser Ser Pro Glu Glu Leu
130                 135                 140

Lys Phe Gln Cys Gly Gln Lys Thr Leu Arg Pro Arg Phe Lys Ile Ile
145                 150                 155                 160

Gly Gly Glu Phe Thr Thr Ile Glu Asn Gln Pro Trp Phe Ala Ala Ile
                165                 170                 175

Tyr Arg Arg His Arg Gly Gly Ser Val Thr Tyr Val Cys Gly Gly Ser
            180                 185                 190

Leu Ile Ser Pro Cys Trp Val Ile Ser Ala Thr His Cys Phe Ile Asp
        195                 200                 205

Tyr Pro Lys Lys Glu Asp Tyr Ile Val Tyr Leu Gly Arg Ser Arg Leu
210                 215                 220

Asn Ser Asn Thr Gln Gly Glu Met Lys Phe Glu Val Glu Asn Leu Ile
225                 230                 235                 240

Leu His Lys Asp Tyr Ser Ala Asp Thr Leu Ala His His Asn Asp Ile
                245                 250                 255

Ala Leu Leu Lys Ile Arg Ser Lys Glu Gly Arg Cys Ala Gln Pro Ser
            260                 265                 270

Arg Thr Ile Gln Thr Ile Cys Leu Pro Ser Met Tyr Asn Asp Pro Gln
        275                 280                 285

Phe Gly Thr Ser Cys Glu Ile Thr Gly Phe Gly Lys Glu Asn Ser Thr
290                 295                 300

Asp Tyr Leu Tyr Pro Glu Gln Leu Lys Met Thr Val Val Lys Leu Ile
305                 310                 315                 320

Ser His Arg Glu Cys Gln Gln Pro His Tyr Tyr Gly Ser Glu Val Thr
                325                 330                 335

Thr Lys Met Leu Cys Ala Ala Asp Pro Gln Trp Lys Thr Asp Ser Cys
            340                 345                 350

Gln Gly Asp Ser Gly Gly Pro Leu Val Cys Ser Leu Gln Gly Arg Met
        355                 360                 365

Thr Leu Thr Gly Ile Val Ser Trp Gly Arg Gly Cys Ala Leu Lys Asp
370                 375                 380

Lys Pro Gly Val Tyr Thr Arg Val Ser His Phe Leu Pro Trp Ile Arg
385                 390                 395                 400

Ser His Thr Lys Glu Glu Asn Gly Leu Ala Leu
                405                 410
```

<210> SEQ ID NO 2
<211> LENGTH: 1296
<212> TYPE: DNA
<213> ORGANISM: Homo sapiens

<400> SEQUENCE: 2

```
atgagagccc tgctggcgcg cctgcttctc tgcgtcctgg tcgtgagcga ctccaaaggc      60
agcaatgaac ttcatcaagt tccatcgaac tgtgactgtc taaatggagg aacatgtgtg     120
tccaacaagt acttctccaa cattcactgg tgcaactgcc caagaaatt cggagggcag      180
cactgtgaaa tagataagtc aaaaacctgc tatgagggga tggtcacttt ttaccgagga     240
aaggccagca ctgacaccat gggccggccc tgcctgccct ggaactctgc cactgtcctt     300
cagcaaacgt accatgccca gatctgat gctcttcagc tgggcctggg gaaacataat       360
tactgcagga acccagacaa ccggaggcga ccctggtgct atgtgcaggt gggcctaaag     420
ccgcttgtcc aagagtgcat ggtgcatgac tgcgcagatg gaaaaaagcc ctcctctcct     480
ccagaagaat taaatttca gtgtggccaa aagactctga ggccccgctt taagattatt      540
ggggagaat tcaccaccat cgagaaccag ccctggtttg cggccatcta caggaggcac      600
cgggggggct ctgtcaccta cgtgtgtgga ggcagcctca tcagcccttg ctgggtgatc     660
agcgccacac actgcttcat tgattaccca aagaaggagg actacatcgt ctacctgggt     720
cgctcaaggc ttaactccaa cacgcaaggg gagatgaagt ttgaggtgga aaacctcatc     780
ctacacaagg actacagcgc tgacacgctt gctcaccaca cgacattgc cttgctgaag      840
atccgttcca aggagggcag gtgtgcgcag ccatcccgga ctatacagac catctgcctg     900
ccctcgatgt ataacgatcc ccagtttggc acaagctgtg agatcactgg ctttggaaaa     960
gagaattcta ccgactatct ctatccggag cagctgaaaa tgactgttgt gaagctgatt    1020
tcccaccggg agtgtcagca gccccactac tacggtctg aagtcaccac caaaatgctg      1080
tgtgctgctg acccacagtg gaaaacagat tcctgccagg gagactcagg gggaccctc     1140
gtctgttccc tccaaggccg catgacttg actggaattg tgagctgggg ccgtggatgt     1200
gccctgaagg acaagccagg cgtctacacg agagtctcac acttcttacc ctggatccgc    1260
agtcacacca aggaagagaa tggcctggcc ctctga                               1296
```

<210> SEQ ID NO 3
<211> LENGTH: 411
<212> TYPE: PRT
<213> ORGANISM: Unknown
<220> FEATURE:
<223> OTHER INFORMATION: Monkey

<400> SEQUENCE: 3

```
Leu Thr Pro Pro Leu Phe Ser Pro Ala Asp Cys Gly Cys Leu Asn Gly
1               5                   10                  15

Gly Thr Cys Met Ser Asn Lys Tyr Phe Ser Ser Ile His Trp Cys Asn
            20                  25                  30

Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly Arg Ser Cys Leu Ala Trp Asn Ser Ala Thr Val Leu
65                  70                  75                  80

Gln Gln Thr Tyr His Ala His Arg Ser Asp Ala Leu Gln Leu Gly Leu
```

85                  90                  95
Gly Lys His Asn Tyr Cys Arg Asn Pro Asp Asn Arg Arg Pro Trp
                100                 105                 110

Cys Tyr Val Gln Val Gly Leu Lys Gln Leu Val Gln Glu Cys Met Val
            115                 120                 125

Gln Asn Cys Ala Asp Gly Lys Lys Pro Ser Ser Pro Glu Glu Leu
        130                 135                 140

Gln Phe Gln Cys Gly Gln Arg Thr Leu Arg Pro Arg Phe Lys Ile Val
145                 150                 155                 160

Gly Gly Glu Phe Thr Thr Ile Glu Asn Gln Pro Trp Phe Ala Ala Ile
                165                 170                 175

Tyr Arg Arg His Arg Gly Gly Ser Val Thr Tyr Val Cys Gly Gly Ser
                180                 185                 190

Leu Ile Ser Pro Cys Trp Val Val Ser Ala Thr His Cys Phe Ile Asn
            195                 200                 205

Tyr Pro Lys Lys Glu Asp Tyr Ile Val Tyr Leu Gly Arg Ser Arg Leu
        210                 215                 220

Asn Ser Asn Thr Gln Gly Glu Met Lys Phe Glu Val Glu Asn Leu Ile
225                 230                 235                 240

Leu His Glu Asp Tyr Ser Ala Asp Thr Leu Ala His His Asn Asp Ile
                245                 250                 255

Ala Leu Leu Lys Ile Arg Ser Lys Glu Gly Arg Cys Ala Gln Pro Ser
            260                 265                 270

Arg Thr Ile Gln Thr Ile Cys Leu Pro Ser Thr Tyr Asn Asp Pro Pro
        275                 280                 285

Phe Gly Thr Ser Cys Glu Ile Thr Gly Phe Gly Lys Glu Asn Ser Thr
290                 295                 300

Asp Tyr Leu Tyr Pro Glu Arg Leu Lys Met Thr Val Val Lys Leu Val
                305                 310                 315                 320

Ser His Gln Lys Cys Arg Gln Pro His Tyr Tyr Gly Ser Glu Val Thr
                325                 330                 335

Thr Lys Met Leu Cys Ala Ala Asp Pro Gln Trp Glu Thr Asp Ser Cys
            340                 345                 350

Gln Gly Asp Ser Gly Gly Pro Leu Val Cys Ser Ile Gln Gly His Met
        355                 360                 365

Thr Leu Thr Gly Ile Val Ser Trp Gly Arg Gly Cys Ala Leu Lys Asp
        370                 375                 380

Lys Pro Gly Val Tyr Thr Arg Val Ser Arg Phe Leu Pro Trp Ile His
385                 390                 395                 400

Ser His Thr Arg Glu Glu Asn Gly Leu Ala Leu
                405                 410

<210> SEQ ID NO 4
<211> LENGTH: 1296
<212> TYPE: DNA
<213> ORGANISM: Unknown
<220> FEATURE:
<223> OTHER INFORMATION: Monkey

<400> SEQUENCE: 4
atgagagccc tgctggcaca cctgcttctc tgcgtcctgg tcgtgagcga ctccaaatcg      60
cttaccccac ctttgttctc tccagcagac tgtggctgtc taaatggagg aacatgtatg     120
tccaacaagt acttctccag cattcactgg tgcaactgcc caagaagtt cggagggcag      180 cactgtgaga tagataagtc aaaaacctgc tatgagggga tggtcacttt ttaccgagga     240

```
aaggccagca ctgacaccat gggccggtcc tgcctggcct ggaactctgc caccgtcctt    300
cagcaaacat accatgccca cagatctgat gctcttcagc tgggcctggg aagcacaat    360 tactgcagga acccagacaa ccggaggcga ccctggtgct atgtgcaggt cggcctaaag    420
cagcttgtcc aagagtgcat ggtgcaaaac tgtgcagatg aaaaaagcc ctcctctcct    480 ccagaagaat tacagtttca gtgtggccaa aggactctga ggccccgctt taagattgtt    540
gggggagaat tcaccaccat cgagaaccag ccctggtttg cagccatcta caggaggcac    600
cggggcggct ctgtcaccta cgtgtgtgga ggcagcctca tcagcccttg ctgggtggtc    660
agcgccacac actgcttcat taattaccca aagaaggagg actacatcgt ctacctgggt    720
cgctcaaggc ttaactccaa cacgcaaggg gagatgaagt ttgaggtgga aacctcatc    780 ctacatgagg actacagcgc tgacacgctt gctcaccaca cgacattgc cttgctgaag    840 atccgttcta aggagggcag gtgtgcgcag ccatcccgga ccatacagac catctgcctg    900
ccctcgacgt ataacgatcc ccttttggc acaagctgtg agatcactgg ctttggaaaa    960
gagaattcta ccgactatct ctatccggag cggctgaaaa tgactgttgt gaagctggtt   1020
tcccaccaga agtgtcggca gccccactac tacggctctg aagtcaccac caaaatgctg   1080
tgtgctgctg acccacagtg ggaaacagat tcctgccagg gagactcagg gggacccctt   1140
gtctgttcca tccaaggcca catgactttg actggaattg tgagctgggg ccgtggatgt   1200
gccctaaagg acaagccagg cgtctacacg agagtctcac gcttcttgcc ctggattcac   1260
agtcacacca gggaagagaa tggcctagcc ctctga                              1296
```

<210> SEQ ID NO 5
<211> LENGTH: 122
<212> TYPE: PRT
<213> ORGANISM: Unknown
<220> FEATURE:
<223> OTHER INFORMATION: Mouse
<400> SEQUENCE: 5

```
Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Asp Tyr
            20                  25                  30

Gly Met Asn Trp Ile Lys Gln Thr Pro Gly Lys Gly Leu Lys Trp Met
        35                  40                  45

Gly Trp Ile Asn Thr Tyr Ser Gly Glu Pro Thr Tyr Ser Asp Glu Phe
    50                  55                  60

Lys Gly Arg Phe Ala Phe Ser Leu Glu Thr Ser Ala Ser Thr Ala Ser
65                  70                  75                  80

Leu Gln Ile Asn Asn Leu Lys Asn Glu Asp Met Ala Thr Tyr Phe Cys
                85                  90                  95

Ala Arg Asp Phe Asp Asp Tyr Asp Ser Ser Arg Tyr Phe Asp Val Trp
            100                 105                 110

Gly Ala Gly Thr Thr Val Thr Val Ser Ser
        115                 120
```

<210> SEQ ID NO 6
<211> LENGTH: 113
<212> TYPE: PRT
<213> ORGANISM: Unknown
<220> FEATURE:
<223> OTHER INFORMATION: Mouse -continued

<400> SEQUENCE: 6

Asp Ile Val Met Ser Gln Ser Pro Ser Leu Gly Val Ser Val Gly
1               5                   10                  15

Glu Lys Leu Thr Met Thr Cys Lys Ser Ser Gln Ser Leu Leu Tyr Ser
            20                  25                  30

Ser Tyr Gln Lys Asn Phe Leu Ala Trp Tyr Gln Gln Lys Pro Gly Gln
        35                  40                  45

Ser Pro Lys Leu Leu Ile Ser Trp Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ile Tyr Pro Pro Thr Phe Gly Gly Gly Thr Lys Leu Glu Ile
            100                 105                 110

Lys

<210> SEQ ID NO 7
<211> LENGTH: 119
<212> TYPE: PRT
<213> ORGANISM: Unknown
<220> FEATURE:
<223> OTHER INFORMATION: Mouse

<400> SEQUENCE: 7

Asp Val Lys Leu Val Glu Ser Gly Gly Gly Leu Val Lys Pro Gly Gly
1               5                   10                  15

Ser Leu Lys Leu Ser Cys Val Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Gly Gly Gly Ser His Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Thr Arg Asp Gly Arg Asp Gly Ser Trp Phe Ala Tyr Trp Gly Gln Gly
            100                 105                 110

Thr Leu Val Thr Val Ser Ala
        115

<210> SEQ ID NO 8
<211> LENGTH: 107
<212> TYPE: PRT
<213> ORGANISM: Unknown
<220> FEATURE:
<223> OTHER INFORMATION: Mouse

<400> SEQUENCE: 8

Asp Ile Val Met Thr Gln Ser Pro Ala Thr Leu Ser Val Thr Pro Gly
1               5                   10                  15

Asp Arg Val Ser Leu Ser Cys Arg Thr Ser Gln Ser Ile Gly Asp Tyr
            20                  25                  30

Leu His Trp Tyr Gln Gln Lys Ser His Glu Ser Pro Arg Leu Leu Ile
        35                  40                  45

Lys Tyr Val Ser Gln Ser Ile Ser Gly Ile Pro Ser Arg Phe Ser Gly

```
                    50                  55                  60
Ser Gly Ser Gly Ser Asp Phe Thr Leu Ser Ile Asn Ser Val Glu Ser
 65                  70                  75                  80

Glu Asp Val Gly Val Tyr Tyr Cys Gln Asn Ser His Ser Phe Pro Leu
                 85                  90                  95

Thr Phe Gly Ser Gly Thr Lys Leu Glu Leu Lys
            100                 105
```

<210> SEQ ID NO 9
<211> LENGTH: 5
<212> TYPE: PRT
<213> ORGANISM: Unknown
<220> FEATURE:
<223> OTHER INFORMATION: Mouse

<400> SEQUENCE: 9

```
Ser Tyr Thr Met Ser
 1               5
```

<210> SEQ ID NO 10
<211> LENGTH: 17
<212> TYPE: PRT
<213> ORGANISM: Unknown
<220> FEATURE:
<223> OTHER INFORMATION: Mouse

<400> SEQUENCE: 10

```
Thr Ile Ser Gly Gly Gly Ser His Ile Tyr Tyr Ala Asp Ser Val Lys
 1               5                  10                  15

Gly
```

<210> SEQ ID NO 11
<211> LENGTH: 10
<212> TYPE: PRT
<213> ORGANISM: Unknown
<220> FEATURE:
<223> OTHER INFORMATION: Mouse

<400> SEQUENCE: 11

```
Asp Gly Arg Asp Gly Ser Trp Phe Ala Tyr
 1               5                  10
```

<210> SEQ ID NO 12
<211> LENGTH: 11
<212> TYPE: PRT
<213> ORGANISM: Unknown
<220> FEATURE:
<223> OTHER INFORMATION: Mouse

<400> SEQUENCE: 12

```
Arg Thr Ser Gln Ser Ile Gly Asp Tyr Leu His
 1               5                  10
```

<210> SEQ ID NO 13
<211> LENGTH: 7
<212> TYPE: PRT
<213> ORGANISM: Unknown
<220> FEATURE:
<223> OTHER INFORMATION: Mouse

<400> SEQUENCE: 13

```
Tyr Val Ser Gln Ser Ile Ser
 1               5
```

```
<210> SEQ ID NO 14
<211> LENGTH: 9
<212> TYPE: PRT
<213> ORGANISM: Unknown
<220> FEATURE:
<223> OTHER INFORMATION: Mouse

<400> SEQUENCE: 14

Gln Asn Ser His Ser Phe Pro Leu Thr
1               5

<210> SEQ ID NO 15
<211> LENGTH: 113
<212> TYPE: PRT
<213> ORGANISM: Unknown
<220> FEATURE:
<223> OTHER INFORMATION: Recombinant-Mouse

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 16
<211> LENGTH: 107
<212> TYPE: PRT
<213> ORGANISM: Unknown
<220> FEATURE:
<223> OTHER INFORMATION: Recombinant-Mouse

<400> SEQUENCE: 16

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro Leu
                85                  90                  95

Thr Phe Gly Gly Gly Thr Lys Val Glu Ile Lys
            100                 105

<210> SEQ ID NO 17
<211> LENGTH: 119
```

```
<212> TYPE: PRT
<213> ORGANISM: Homo sapiens

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Thr Ile Ser Gly Gly Gly Ser His Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Arg Asp Gly Ser Trp Phe Ala Tyr Trp Gly Gln Gly
            100                 105                 110

Thr Leu Val Thr Val Ser Ser
            115

<210> SEQ ID NO 18
<211> LENGTH: 107
<212> TYPE: PRT
<213> ORGANISM: Homo sapiens

<400> SEQUENCE: 18

Asp Val Val Met Thr Gln Ser Pro Ala Phe Leu Ser Val Thr Pro Gly
1               5                   10                  15

Glu Lys Val Thr Ile Thr Cys Arg Thr Ser Gln Ser Ile Gly Asp Tyr
            20                  25                  30

Leu His Trp Tyr Gln Gln Lys Pro Asp Gln Ser Pro Lys Leu Leu Ile
        35                  40                  45

Lys Tyr Val Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asn Ser His Ser Phe Pro Leu
                85                  90                  95

Thr Phe Gly Gly Gly Thr Lys Val Glu Ile Lys
            100                 105

<210> SEQ ID NO 19
<211> LENGTH: 443
<212> TYPE: PRT
<213> ORGANISM: Unknown
<220> FEATURE:
<223> OTHER INFORMATION: Mouse

<400> SEQUENCE: 19

Asp Val Lys Leu Val Glu Ser Gly Gly Gly Leu Val Lys Pro Gly Gly
1               5                   10                  15

Ser Leu Lys Leu Ser Cys Val Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Gly Gly Gly Ser His Ile Tyr Tyr Ala Asp Ser Val
    50                  55                  60
```

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
            85                  90                  95

Thr Arg Asp Gly Arg Asp Gly Ser Trp Phe Ala Tyr Trp Gly Gln Gly
        100                 105                 110

Thr Leu Val Thr Val Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
            245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
            325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440

<210> SEQ ID NO 20
<211> LENGTH: 214
<212> TYPE: PRT
<213> ORGANISM: Unknown
<220> FEATURE:

<223> OTHER INFORMATION: Mouse

<400> SEQUENCE: 20

```
Asp Ile Val Met Thr Gln Ser Pro Ala Thr Leu Ser Val Thr Pro Gly
1               5                   10                  15

Asp Arg Val Ser Leu Ser Cys Arg Thr Ser Gln Ser Ile Gly Asp Tyr
            20                  25                  30

Leu His Trp Tyr Gln Gln Lys Ser His Glu Ser Pro Arg Leu Leu Ile
        35                  40                  45

Lys Tyr Val Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Ser
65                  70                  75                  80

Glu Asp Val Gly Val Tyr Tyr Cys Gln Asn Ser His Ser Phe Pro Leu
                85                  90                  95

Thr Phe Gly Ser Gly Thr Lys Leu Glu Leu Lys Arg Thr Val Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 21
<211> LENGTH: 446
<212> TYPE: PRT
<213> ORGANISM: Homo sapiens

<400> SEQUENCE: 21

```
Asp Val Lys Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Ser His Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Gly Arg Asp Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 22
<211> LENGTH: 214
<212> TYPE: PRT
<213> ORGANISM: Homo sapiens

<400> SEQUENCE: 22

Asp Ile Val Met Thr Gln Ser Pro Ala Phe Leu Ser Val Thr Pro Gly
1               5                   10                  15

Glu Lys Val Thr Ile Ser Cys Arg Thr Ser Gln Ser Ile Gly Asp Tyr
                20                  25                  30

Leu His Trp Tyr Gln Gln Lys Pro Asp Gln Ser Pro Lys Leu Leu Ile
            35                  40                  45

Lys Tyr Val Ser Gln Ser Ile Ser Gly Ile Pro Ser Arg Phe Ser Gly
        50                  55                  60
```

Ser Gly Ser Gly Ser Asp Phe Thr Phe Thr Ile Ser Ser Leu Glu Ala
 65                  70                  75                  80

Glu Asp Ala Ala Thr Tyr Tyr Cys Gln Asn Ser His Ser Phe Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 1332
<212> TYPE: DNA
<213> ORGANISM: Unknown
<220> FEATURE:
<223> OTHER INFORMATION: Mouse

<400> SEQUENCE: 23
gacgtcaagc tggtggaaag cggaggaggc ctggtcaaac ccggaggcag cctgaagctg      60
agctgcgtgg ccagcggctt caccttcagc agctacacaa tgagctgggt gaggcagaca     120
cccgagaaga ggctggagtg ggtggctacc attagcggag cggcagcca catctactac      180 gccgacagcg tgaagggcag gttcaccatc agcagggaca cgccaagaa caccctgtac      240 ctgcagatga gcagcctgaa gagcgaggac accgccatct actactgcac cagggacggc     300
agagacggca gctggttcgc ctactgggga cagggaaccc tggtgaccgt gagcgccgcc     360
aaaacgacac cccatctgt ctatccgcta gcccctggat ctgctgccca aactaactcc      420
atggtgaccc tgggatgcct ggtcaagggc tatttccctg agccagtgac agtgacctgg     480
aactctggat ccctgtccag cggtgtgcac accttccag ctgtcctgca gtctgacctc     540
tacactctga gcagctcagt gactgtcccc tccagcacct ggcccagcga ccgtcacc      600 tgcaacgttg cccacccggc cagcagcacc aaggtggaca agaaaattgt gcccagggat     660
tgtggttgta agccttgcat atgtacagtc ccagaagtat catctgtctt catcttcccc     720
ccaaagccca aggatgtgct caccattact ctgactccta aggtcacgtg tgttgtggta     780
gacatcagca aggatgatcc cgaggtccag ttcagctggt ttgtagatga tgtggaggtg     840
cacacagctc agacgcaacc ccgggaggag cagttcaaca gcactttccg ctcagtcagt     900
gaacttccca tcatgcacca ggactggctc aatggcaagg agttcaaatg cagggtcaac     960
agtgcagctt tccctgcccc catcgagaaa accatctcca aaaccaaagg cagaccgaag    1020
gctccacagg tgtacaccat tccacctccc aaggagcaga tggccaagga taaagtcagt    1080
ctgacctgca tgataacaga cttcttccct gaagacatta ctgtggagtg cagtggaat     1140 gggcagccag cggagaacta caagaacact cagcccatca tggacacaga tggctcttac    1200

| | |
|---|---|
| ttcgtctaca gcaagctcaa tgtgcagaag agcaactggg aggcaggaaa tactttcacc | 1260 |
| tgctctgtgt tacatgaggg cctgcacaac caccatactg agaagagcct ctcccactct | 1320 |
| cctggtaaat ga | 1332 |

<210> SEQ ID NO 24
<211> LENGTH: 645
<212> TYPE: DNA
<213> ORGANISM: Unknown
<220> FEATURE:
<223> OTHER INFORMATION: Mouse

<400> SEQUENCE: 24

| | |
|---|---|
| gacatcgtga tgacccagag ccctgctaca ctgagcgtga cccccggaga cagggtgagc | 60 |
| ctgagctgca ggacctccca gagcatcggc gactacctgc actggtacca gcagaagagc | 120 |
| cacgagagcc ccaggctgct gatcaagtac gtgagccaga gcatcagcgg cattcccagc | 180 |
| aggttcagcg gcagcggaag cggaagcgac ttcaccctca gcatcaacag cgtggaaagc | 240 |
| gaggacgtgg gcgtgtacta ctgccagaac agccacagct tccccctcac cttcggcagc | 300 |
| ggcaccaagc tggagctgaa gaggaccgtg gcggcgccaa ctgtatccat cttcccacca | 360 |
| tccagtgagc agttaacatc tggaggtgcc tcagtcgtgt gcttcttgaa caacttctac | 420 |
| cccaaagaca tcaatgtcaa gtggaagatt gatggcagtg aacgacaaaa tggcgtcctg | 480 |
| aacagttgga ctgatcagga cagcaaagac agcacctaca gcatgagcag caccctcacg | 540 |
| ttgaccaagg acgagtatga acgacataac agctatacct gtgaggccac tcacaagaca | 600 |
| tcaacttcac ccattgtcaa gagcttcaac aggaatgagt gttag | 645 |

<210> SEQ ID NO 25
<211> LENGTH: 1341
<212> TYPE: DNA
<213> ORGANISM: Homo sapiens

<400> SEQUENCE: 25

| | |
|---|---|
| gacgtgaagc tggtggaaag cggaggcggc ctcgtgaaac ctggcggaag cctgagactg | 60 |
| agctgcgctg ccagcggctt caccttcagc agctacacca tgagctgggt gaggcaggct | 120 |
| cccggcaaag gactggagtg ggtggccaca attagcggag cggctcccca tatctactac | 180 |
| gccgacagcg tcaagggcag gttcaccatc agcagggaca cgccaagaa cagcctgtac | 240 |
| ctgcagatga acagcctgag ggccgaggac accgccgtgt actactgcac cagggacggc | 300 |
| agggacggaa gctggttcgc ctactgggga cagggcaccc tcgtgaccgt gagcagcgct | 360 |
| agcaccaagg gcccatccgt cttccccctg gcgccctgct ccaggagcac ctccgagagc | 420 |
| acagccgccc tgggctgcct ggtcaaggac tacttccccg aaccggtgac ggtgtcgtgg | 480 |
| aactcaggcg ccctgaccag cggcgtgcac accttcccgg ctgtcctaca gtcctcagga | 540 |
| ctctactccc tcagcagcgt ggtgaccgtg ccctccagca gcttgggcac gaagacctac | 600 |
| acctgcaacg tagatcacaa gcccagcaac accaaggtgg acaagagagt tgagtccaaa | 660 |
| tatggtcccc catgcccacc atgcccagca cctgagttcc tggggggacc atcagtcttc | 720 |
| ctgttccccc caaaacccaa ggacactctc atgatctccc ggacccctga ggtcacgtgc | 780 |
| gtggtggtgg acgtgagcca ggaagacccc gaggtccagt tcaactggta cgtggatggc | 840 |
| gtggaggtgc ataatgccaa gacaaagccg cgggaggagc agttcaacag cacgtaccgt | 900 |
| gtggtcagcg tcctcaccgt cctgcaccag gactggctga acggcaagga gtacaagtgc | 960 |

-continued

```
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc ctcccgtgct ggactccgac    1200
ggctccttct tcctctacag caggctaacc gtggacaaga gcaggtggca ggaggggaat    1260
gtcttctcat gctccgtgat gcatgaggct ctgcacaacc actacacaca gaagagcctc    1320
tccctgtctc tgggtaaatg a                                              1341

<210> SEQ ID NO 26
<211> LENGTH: 645
<212> TYPE: DNA
<213> ORGANISM: Homo sapiens

<400> SEQUENCE: 26
gacatcgtga tgacccagag ccccgccttc ctgagcgtga cacctggaga gaaggtgacc      60
atcagctgca ggaccagcca gagcatcggc gactacctgc actggtacca gcagaagccc    120
gaccagagcc ccaagctgct gatcaagtac gtgagccagt ccatcagcgg catcccttcc    180
agatttagcg gcagcggcag cggaagcgac ttcaccttca ccatcagcag cctggaagcc    240
gaagacgccg ccacctacta ctgccagaac tcccacagct tcccctgac attcggcggc     300 ggcaccaagg tggagatcaa gaggactgtg gcggcgccat ctgtcttcat cttcccgcca    360
tctgatgagc agttgaaatc tggtaccgct agcgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacctgacg    540 ctgagcaaag cagactacga gaacacaaa gtctacgcct gcgaagtcac ccatcagggc    600
ctgagctcgc ccgtcacaaa gagcttcaac aggggagagt gttag                   645
```

ANTIBODIES THAT BIND UROKINASE PLASMINOGEN ACTIVATOR

CROSS-REFERENCE TO RELATED APPLICATIONS

This application is a 35 U.S.C. § 371 National Stage application of International Application PCT/EP2014/065136 (WO 2015/007727), filed Jul. 15, 2014, which claims priority to European Patent Application 13176519.0, filed Jul. 15, 2013; this application claims priority under 35 U.S.C. §119 to U.S. Provisional Application 61/847,664; filed Jul. 18, 2013.

SEQUENCE LISTING

In accordance with 37 C.F.R. §1.52(e)(5), Applicants enclose herewith the Sequence Listing for the above-captioned application entitled "8692US02_SeqListing", created on Jan. 15, 2016. The Sequence Listing is made up of 37,882 bytes, and the information contained in the attached "SEQUENCE LISTING" is identical to the information in the specification as originally filed. No new matter is added.

TECHNICAL FIELD OF THE INVENTION

The present invention relates to a method of identifying urokinase plasminogen activator (uPA) antibodies. The invention also relates to antibodies that are capable of binding uPA and which are capable of inhibiting or blocking uPA activities. Furthermore, the invention relates to uses of such antibodies, such as therapeutic and pharmaceutical uses.

BACKGROUND OF INVENTION

The urokinase plasminogen activator (uPA) is an extracellular serine protease. UPA consists of 3 domains: 1) The growth factor domain (GFD) that mediates binding of uPA to its receptor uPAR; 2) The kringle domain of uPA that is described to interact with integrins; and 3) The catalytic domain that mediates the proteolytic function of uPA. The primary proteolytic function of uPA is to convert the inactive zymogen plasminogen (Plg) to the active serine protease plasmin. UPA is produced as a single-chain zymogen (sc-uPA), which can be endoproteolytically cleaved at the Lys158-Ile159 peptide bond (numbering corresponding to human sc-uPA). The resulting two-chain form of uPA (tc-uPA) is held together by a single disulfide bridge. The proteolytic activity of sc-uPA is minimal compared to that of tc-uPA, but sc-uPA does harbour some intrinsic proteolytic activity. The catalytic domain of uPA exists in equilibrium of two structural conformations, an active and an inactive conformation. In sc-uPA the inactive conformation of the catalytic domain is favoured. Hydrolysis of the Lys158-Ile159 peptide bond shifts the dynamic equilibrium between these structural conformations to favour the active form (Jiang et al., Biochem. J. 449:161-166, 2013).

In the healthy organism, the presence of uPA outside the urinary and gastrointestinal tract is generally limited to circulating granulocytes and certain cell types in tissues undergoing remodelling. During disease, uPA is also found at sites of inflammatory disorders and cancer lesions. Animal studies have demonstrated a functional role of uPA in cancer and in inflammatory disorders including arthritic diseases. Antagonising uPA would therefore be desirable in treatment of cancer and inflammatory diseases such as rheumatoid arthritis and psoriatic arthritis.

Patent documents U.S. Pat. No. 8,062,637 and WO03033009 provide experimental evidence for a functional role of uPA in arthritic diseases. The documents further describe a method for ameliorating the effects of an inflammatory disease in a subject, comprising administering to the subject an antagonist, including antibodies that specifically bind uPA. The documents U.S. Pat. No. 8,062,637 and WO03033009 describe possible uses of antibodies that bind uPA but neither of the documents describe or provide data for any antibody that binds uPA.

Patent document WO2006050177 describes a method for identifying anti-uPA antibodies that are specific for an 86 amino acid long epitope corresponding to the kringle domain of uPA and the potential use of these antibodies for treatment of inflammatory diseases. The WO2006050177 patent document does not describe or provide data for any antibody that binds uPA. Furthermore, antibodies that bind to the kringle domain are predicted to have no effect on the proteolytic function of uPA, because the proteolytic properties of uPA are primarily associated with the catalytic domain.

Patent document WO2005048822 describes two anti-uPA antibodies, ATN-291 and ATN-292, that specifically bind to the growth factor domain (GFD) (ATN-292) and the kringle domain (ATN-291) of uPA. The WO2005048822 patent document further describes the potential use of these antibodies for treatment of cancer or other diseases. Antibodies that bind to either the GFD or the kringle domain are predicted to have no effect on the proteolytic function of uPA, because the proteolytic properties of uPA are primarily associated with the catalytic domain.

Patent document U.S. Pat. No. 5,496,549 describes a bispecific antibody, in which one of the two specificities is conferred by either of three anti-uPA antibodies, UK1-3, UK1-87, and UK1-6. The other specificity is towards a platelet surface protein and the patent further describes the potential use of these bispecific antibodies to deliver an active biological substance, in this case uPA, for treatment of thrombosis or other cardiovascular disease. None of these three antibodies inhibit the proteolytic activity of uPA but are designed to deliver or concentrate uPA at sites of platelet deposition.

As described above, antibodies that bind uPA are known; and their uses in treatment of inflammatory diseases have been envisaged. However to current date, no anti-uPA antibodies have entered clinical trials. Thus, there is still an unmet need for therapeutic anti-uPA antibodies for example for use in patients with inflammatory diseases or patients with cancer.

Disclosed herein are anti-uPA antibodies with novel characteristics. These antibodies are suitable for the development of pharmaceuticals. Such antibodies may have a substantial impact upon the quality of life of individuals with cancer or inflammatory diseases.

SUMMARY OF INVENTION

The present invention relates to antibodies or antigen-binding fragments thereof that are capable of binding to human uPA characterised in that they inhibit the proteolytic activity of the proteolytically active form of uPA and inhibit activation of single chain uPA (sc-uPA) from a proteolytically inactive form of uPA to a proteolytically active form of uPA. For the first time, inhibitory monoclonal antibodies specific for human uPA that harbour this dual functionality have been identified. These antibodies inhibit the activation of the zymogen form of uPA, sc-uPA, by (active) plasmin, and at the same time the antibodies inhibit the proteolytic activity of two-chain uPA (tc-uPA) towards the (inactive) zymogen plasminogen. The antibodies thus inhibit both proteolytic reactions of the reciprocal zymogen activation loop between sc-uPA and plasminogen, providing a more potent inhibition of the overall proteolytic cascade reaction. The advantage of a dual-acting antibody compared to an antibody that only inhibits the proteolytic activity of tc-uPA is illustrated by a set of mouse antibodies, mU1 and mU3. The dual-acting mouse antibody mU1 had similar ability to bind mouse uPA and to inhibit the proteolytic function of mouse tc-uPA compared to mU3, but had superior ability to functionally inhibit mouse uPA activity in a cell-based assay and in an in vivo mouse model (Lund et al., J. Biol. Chem. 283:32506-32515, 2008). These antibodies are specific for mouse uPA, and are therefore not expected to bind human uPA, and are as such therefore not suitable for use within the scope of this application. They do not have all of the same novel characteristics or the potential for pharmaceutical development as the anti-uPA antibodies described in the present invention.

The binding sites of several prior art anti-uPA antibodies on human uPA or on mouse uPA have been published (Jiang et al., 2013, Biochem J 449, 161-166; Kromann-Hansen et al., 2013, Biochemistry 52, 7114-7126). We describe a dual-acting anti-uPA antibody that binds to a novel epitope on human uPA, and demonstrate that this antibody induces a synergistic conformational change throughout the human uPA polypeptide that involves amino acids in all three major domains of uPA: the GFD, kringle, and catalytic domains. In addition to the novel epitope and novel way of inhibiting the enzyme, this domain-spanning conformational change is also unprecedented.

In one aspect of the invention, the antibodies are capable of binding to and inhibiting both receptor-bound uPA and non-receptor-bound uPA. This adds an advantage because certain proteolytic functions of uPA are demonstrated to be dependent on binding to the uPA receptor, uPAR, while other proteolytic functions of uPA are demonstrated to be independent of uPAR. Data disclosed in patent document WO03033009A illustrates a role of uPA in a mouse arthritis model that is likely dependent on uPAR and also dependent on the proteolytic activity of uPA. Antibodies with the capability to inhibit the function of both receptor-bound uPA and non-receptor-bound uPA therefore have an advantage, because all forms of uPA will be inhibited by such antibodies, and it is not known for any given human disease, as described herein, to what degree the disease-relevant function of uPA is dependent on binding to uPAR. It is not trivial to identify antibodies that inhibit the activation of sc-uPA and at the same time are capable of binding to receptor-bound uPA with high affinity. This is illustrated by the antibody, mAb-PUK, which as disclosed in the literature is able to inhibit the activation of sc-uPA but has >10-fold diminished ability to bind sc-uPA that is bound to uPAR compared to non-receptor-bound sc-uPA (Botkjaer et al., Biochem J. 438:39-51, 2011). MAb-PUK has no effect on the activity of tc-uPA and does not have the same novel characteristics as the anti-uPA antibodies described in the present invention, as demonstrated in Example 14.

In another aspect of the invention, the antibodies are capable of binding to and inhibiting endogenously expressed human uPA in inflammatory cells. This is illustrated in Example 9 of the example section below, in which antibodies of the invention inhibit endogenously expressed uPA in primary human macrophages. This demonstrates the ability of the antibodies to inhibit uPA in the natural form that is present in a disease-relevant cell type. Known uPA antibodies are not known to be able to inhibit the proteolytic activity of uPA, including endogenous uPA, in primary human macrophages.

In another aspect of the invention, the antibodies are capable of binding to and inhibiting human uPA and also capable of binding to and inhibiting non-human primate uPA. This adds a distinctive advantage to the antibodies of the present invention since known uPA antibodies are not known to bind to or inhibit uPA from non-human primates, such as cynomolgus monkeys, which means that the known antibodies cannot be tested in these animals that are commonly used in preclinical studies for the development of pharmaceuticals.

The anti-uPA antibodies of the invention may be used as pharmaceuticals for the treatment of individuals with one or more autoimmune diseases and/or chronic inflammatory diseases and/or individuals with cancer. Hence, the present invention also relates to a method of treatment of individuals with one or more autoimmune diseases and/or inflammatory diseases and/or individuals with cancer.

The present invention also relates to a method of identifying anti-uPA antibodies. This immunisation and screening method has been designed to allow for the identification of dual-acting anti-uPA antibodies according to the invention. The method of identifying a dual-acting anti-uPA antibody comprises the steps of: (a) generating anti-uPA antibodies; (b) identifying antibodies from the antibodies generated in step (a) that inhibit proteolytic activity of tc-uPA; (c) identifying antibodies from the antibodies generated in step (a) that inhibit activation of sc-uPA from a proteolytically inactive form to a proteolytically active form; and (d) selecting antibodies that are inhibitory in both steps (b) and (c).

BRIEF DESCRIPTION OF DRAWINGS

FIG. 2: represent the VH, VL and CDR amino acid sequences of the 0266-0000-0010 and hz0266-0000-0010 antibodies (as described in more detail in Example 13).

BRIEF DESCRIPTION OF THE SEQUENCES

Figure 1:
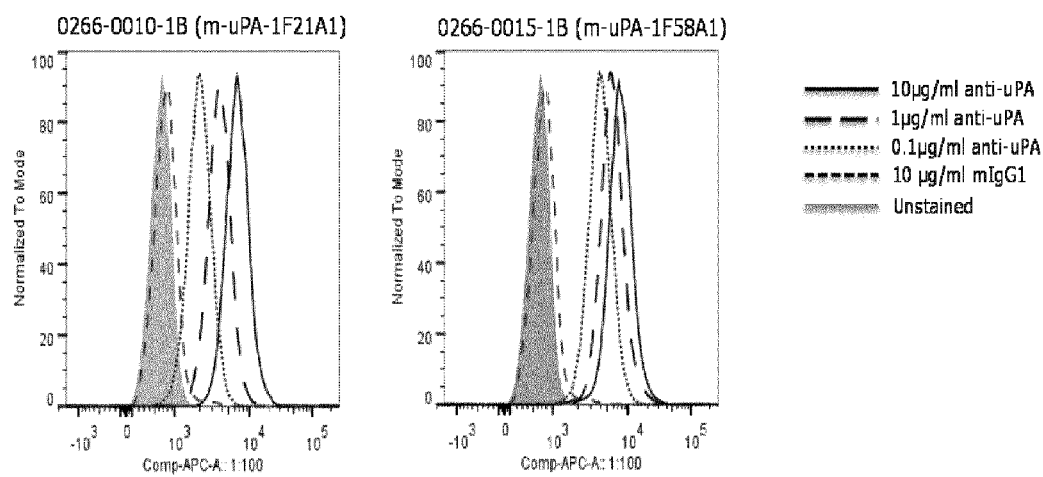
FIG. 1: Flow cytometric analysis showing dose-dependent binding of Alexa647-conjugated 0266-0000-0010 and 0266-0000-0015, respectively, to primary human macrophages.

SEQ ID NO: 1 represents the amino acid sequence of recombinant human sc-uPA.

SEQ ID NO: 2 represents the DNA sequence of recombinant human sc-uPA.

SEQ ID NO: 3 represents the amino acid sequence of wild type cynomolgus sc-uPA.

SEQ ID NO: 4 represents the DNA sequence of wild type cynomolgus sc-uPA.

SEQ ID NO: 5 represents the VH sequence of 0266-0000-0015.

SEQ ID NO: 6 represents the VL sequence of 0266-0000-0015.

SEQ ID NO: 7 represents the VH sequence of 0266-0000-0010.

SEQ ID NO: 8 represents the VL sequence of 0266-0000-0010.

SEQ ID NO: 9 represents the CDR-H1 sequence of 0266-0000-0010.

SEQ ID NO: 10 represents the CDR-H2 sequence of 0266-0000-0010.

SEQ ID NO: 11 represents the CDR-H3 sequence of 0266-0000-0010

SEQ ID NO: 12 represents the CDR-L1 sequence of 0266-0000-0010.

SEQ ID NO: 13 represents the CDR-L2 sequence of 0266-0000-0010.

SEQ ID NO: 14 represents the CDR-L3 sequence of 0266-0000-0010.

SEQ ID NO: 15 represents the VH3_21/JH4 sequence.

SEQ ID NO: 16 represents the V6D_41/JK4 sequence.

SEQ ID NO: 17 represents the VH sequence of hz0266-0000-0010.

SEQ ID NO: 18 represents the VL sequence of hz0266-0000-0010.

SEQ ID NO: 19 represents the heavy chain sequence of rec0266-0000-0010

SEQ ID NO: 20 represents the light chain sequence of rec0266-0000-0010

SEQ ID NO: 21 represents the heavy chain sequence of 0266-0000-0043

SEQ ID NO: 22 represents the light chain sequence of 0266-0000-0043

SEQ ID NO: 23 represents the DNA sequence for the heavy chain of rec0266-0000-0010.

SEQ ID NO: 24 represents the DNA sequence for the light chain of mAb rec0266-0000-0010.

SEQ ID NO: 25 represents the DNA sequence for the heavy chain of mAb 0266-0000-0043.

SEQ ID NO: 26 represents the DNA sequence for the light chain of mAb 0266-0000-0043.

DETAILED DESCRIPTION

In one aspect, the present invention provides antibodies or antigen-binding fragments thereof that are capable of binding to human uPA characterised in that they inhibit the proteolytic activity of tc-uPA and inhibit activation of sc-uPA from a proteolytically inactive form of uPA to a proteolytically active form of uPA.

Urokinase Plasminogen Activator (uPA):

UPA is an extracellular serine protease that contains 411 amino acids (SEQ ID NO: 1) (Andreasen et al., Cell Mol. Life Sci. 57:25-40, 2000; Ulisse et al., Current Cancer Drug Targets, 9:32-71, 2009). UPA consists of 3 domains: 1) The N-terminal growth factor-like domain (GFD) that mediates binding of uPA to its cell surface-bound receptor uPAR; 2) The kringle domain of uPA that is described to interact with integrins; and 3) The C-terminal catalytic domain of uPA that mediates its proteolytic activity. UPA is produced as a single-chain zymogen (sc-uPA), which can be endoproteolytically cleaved at the Lys158-Ile159 peptide bond (numbering corresponding to human sc-uPA). The resulting two-chain form of uPA (tc-uPA) is held together by a single disulfide bridge. The proteolytic activity of sc-uPA is minimal compared to that of tc-uPA, but sc-uPA does harbour some intrinsic proteolytic activity. The catalytic domain of uPA exists in equilibrium of two structural conformations, an active and an inactive conformation. In sc-uPA the inactive conformation of the catalytic domain is favoured. Hydrolysis of the Lys158-Ile159 peptide bond shifts the dynamic equilibrium between these structural conformations to favour the active form (Jiang et al., Biochem. J. 449:161-166, 2013). The primary proteolytic function of uPA is to convert the inactive zymogen plasminogen (Plg) to the active serine protease plasmin. Plasminogen is a liver-secreted zymogen present in plasma at ~2 µM, and also present extracellularly at high concentration throughout the interstitial space. In turn, plasmin is the most potent activator of sc-uPA forming a so-called reciprocal zymogen activation loop between sc-uPA and plasminogen. Both sc-uPA and tc-uPA can bind with sub-nanomolar affinity to the glycosylphosphatidylinositol (GPI)-anchored cell surface receptor uPAR (CD87) that contributes to the spatial restriction of uPA activity. In addition to temporal and spatial control of enzymatic activation, the activity of uPA and plasmin are further balanced by their endogenous inhibitors plasminogen activator inhibitor-1 (PAI-1) and α2-antiplasmin (α2-AP), respectively. These serine protease inhibitors (serpins) form irreversible covalent complexes with their cognate proteases.

Definitions uPA:

The terms urokinase plasminogen activator and uPA as used interchangeably herein, and encompass any naturally occurring, endogenously produced and/or recombinant forms of uPA which may be derived from any suitable organism. For example, uPA may be the single-chain zymogen form (sc-uPA) and the two-chain active form (tc-uPA). The terms urokinase plasminogen activator and uPA furthermore encompass all structural conformations of sc-uPA and tc-uPA including the inactive and active conformations of the catalytic domain. The terms urokinase plasminogen activator and uPA furthermore encompass both receptor-bound and non-receptor-bound forms of uPA, as well as uPA in any subcellular location including uPA that is found on the surface of a cell or uPA that is found intracellularly. The terms urokinase plasminogen activator and uPA furthermore encompass any precursor forms of uPA and any degradation forms of uPA. The terms urokinase plasminogen activator and uPA furthermore encompass human uPA or uPA from another species, such as mammalian uPA, such as uPA from a primate (e.g. a chimpanzee, a cynomolgus monkey or a rhesus monkey); a rodent (such as a mouse or a rat), a lagomorph (such as a rabbit), or an artiodactyl (such a cow, sheep, pig or camel). The terms urokinase plasminogen activator and uPA furthermore encompass recombinantly generated uPA. This includes any uPA "generated by recombinant gene technology", including but not limited to proteins expressed in a mammalian cell line or bacteria or yeast.

The term 'recombinant' does not imply that the protein has been altered relative to the naturally occurring form, as recombinantly generated protein are as close as possible to the natural occurring form of the protein. The term 'recombinant' as used within the current application, therefore applies to wild-type as well as mutant forms of proteins.

Single-Chain uPA (sc-uPA):

The term single-chain uPA (sc-uPA) is used herein to denote the single-chain 411 amino acid zymogen form (or pro-form) of human uPA, that has not been subject to proteolytic cleavage at the Lys158-Ile159 peptide bond (of human sc-uPA). sc-uPA is interchangeably referred to in the literature as either sc-uPA or pro-uPA. The term sc-uPA furthermore encompasses all structural conformations of sc-uPA including the inactive and active conformations of the catalytic domain. The term sc-uPA furthermore encompasses both receptor-bound and non-receptor-bound forms of sc-uPA. The term sc-uPA encompasses sc-uPA from all species including human and other relevant species.

Two-Chain uPA (tc-uPA):

The term two-chain uPA (tc-uPA) is used herein to denote the two-chain form of human uPA that has been subject to proteolytic cleavage at the Lys158-Ile159 peptide bond (of human sc-uPA). The term tc-uPA furthermore encompasses all structural conformations of tc-uPA including the inactive and active conformations of the catalytic domain. The term tc-uPA furthermore encompasses both receptor-bound and non-receptor-bound forms of tc-uPA. The term tc-uPA also encompasses tc-uPA from all species including human and other relevant species.

Inactive Form of uPA:

The term 'inactive form of uPA' or 'proteolytically inactive uPA' or 'inactive uPA' is used herein to denote all forms of uPA that are proteolytically inactive or have significantly reduced proteolytic activity (i.e. 50%, 60%, 70%, 80%, 85%, 90% or 95% reduction in proteolytic activity relative to a negative control) The term 'inactive form of uPA' or 'proteolytically inactive uPA' or 'inactive uPA' furthermore encompasses both sc-uPA and tc-uPA provided that these forms of uPA are in a state where they are proteolytically inactive or have significantly reduced proteolytic activity. The term 'inactive form of uPA' or 'proteolytically inactive uPA' or 'inactive uPA' furthermore encompasses all structural conformations of uPA provided that these structural conformations of uPA are proteolytically inactive or have significantly reduced proteolytic activity. The term 'inactive form of uPA' or 'proteolytically inactive uPA' or 'inactive uPA' furthermore encompasses both receptor-bound and non-receptor-bound forms of uPA. The term 'inactive form of uPA' or 'proteolytically inactive uPA' or 'inactive uPA' furthermore encompasses uPA from all species including human and other relevant species.

Active Form of uPA:

The term 'active form of uPA' or 'proteolytically active uPA' or 'active uPA' is used herein to denote all forms of uPA that are proteolytically active and do not have significantly reduced proteolytic activity. The term 'active form of uPA' or 'proteolytically active uPA' or 'active uPA' furthermore encompasses both sc-uPA and tc-uPA provided that these forms of uPA are in a state where they are proteolytically active and do not have significantly reduced proteolytic activity (i.e. 50%, 60%, 70%, 80%, 85%, 90% or 95% reduction in proteolytic activity relative to a negative control). The term 'active form of uPA' or 'proteolytically active uPA' or 'active uPA' furthermore encompasses all structural conformations of uPA provided that these structural conformations of uPA are proteolytically active and do not have significantly reduced proteolytic activity. The term 'active form of uPA' or 'proteolytically active uPA' or 'active uPA' furthermore encompasses both receptor-bound and non-receptor-bound forms of uPA. The term 'active form of uPA' or 'proteolytically active uPA' or 'active uPA' furthermore encompasses uPA from all species including human and other relevant species.

Dual-Acting Anti-uPA Antibodies:

One important aspect of the anti-uPA antibodies of the present invention is their dual mode-of-action, herein referred to as "dual-acting" antibodies. The antibodies of the invention inhibit both proteolytic activity of human tc-uPA and activation of human sc-uPA from a proteolytically inactive form of human uPA to a proteolytically active form of human uPA.

Activation of sc-uPA:

The present invention describes antibodies that inhibit the activation of sc-uPA from a proteolytically inactive form of uPA to a proteolytically active form of uPA. The activation of sc-uPA is a multi-step process that has not been entirely described in the literature. The following should not be interpreted as an exhaustive description of the steps involved in the activation of sc-uPA: One of the steps involved in the activation of sc-uPA is the protein-protein interaction between sc-uPA and another protease, for which sc-uPA is a substrate. A non-exclusive example of such a protease is plasmin. Another step in the activation of sc-uPA is the endoproteolytic cleavage of a single peptide bond between Lys158 and Ile159 (of human sc-uPA), located within the so-called activation loop. Another step in the activation of uPA is the insertion of the newly formed N-terminus into a hydrophobic pocket termed the activation pocket situated within the catalytic domain. Another step in the activation of uPA is a structural change in the catalytic domain from a conformation characterised by several flexible loop regions in the three-dimensional structure to a structurally more compact conformation. Four segments have been defined as involved in significant conformation changes upon activation of serine proteases, including sc-uPA. These four segments are termed the activation loop, the autolysis loop, the oxyanion-stabilizing loop, and the S1 entrance frame.

An antibody that binds uPA as described in the present invention may inhibit one or more steps in the activation of sc-uPA including steps that are not known or not described above. As an example, an antibody as described in the present invention may inhibit the activation of sc-uPA by blocking the protein-protein interaction between sc-uPA and a protease required to cleave the Lys158-Ile159 peptide bond. As another example, such an antibody may inhibit the activation of sc-uPA by binding to or close (e.g. less than 10, 5, 2 or 1 amino acid(s)) to the Lys158-Ile159 peptide bond and thereby protecting this peptide bond from cleavage. As another example, such an antibody may inhibit the activation of uPA by inhibiting the insertion of the newly formed N-terminus into the hydrophobic activation pocket of the catalytic domain. As another example, such an antibody may inhibit the activation of uPA by inhibiting a conformational change involved in the transition from an inactive to an active structural conformation.

Example 8, of the Example section of this specification, describes one specific way of identifying antibodies that inhibit this activation of sc-uPA by measuring the catalytic activity of uPA using a chromogenic uPA substrate.

Activity of tc-uPA:

The present invention describes antibodies that inhibit the activity of tc-uPA. The activity of tc-uPA in this context refers to the proteolytic activity of tc-uPA towards natural and synthetic substrates. A non-exclusive example of such a substrate is plasminogen. The activity of tc-uPA is a multi-step process that has not been entirely described in the literature. The following should not be interpreted as an exhaustive description of the steps involved in the proteolytic activity of tc-uPA. One of the steps involved in the proteolytic activity of tc-uPA is the protein-protein interaction between tc-uPA and a protein that can act as a substrate for tc-uPA. Another requirement for the activity of tc-uPA is access to the catalytic site of tc-uPA. Another requirement for the activity of tc-uPA is the stability of a structurally compact conformation of the catalytic domain. Four segments that undergo significant conformational changes upon activation of serine proteases are considered to be important for the activity of tc-uPA. These four segments are termed the activation loop, the autolysis loop, the oxyanion-stabilizing loop, and the S1 entrance frame. Another requirement for the activity of tc-uPA is the release of substrates that are bound to the catalytic site of tc-uPA.

An antibody that binds uPA as described in the present invention may inhibit one or more steps and/or requirements for the activity of tc-uPA including steps and/or requirements that are not known or not described above. As an example, an antibody as described in the present invention may inhibit the activity of tc-uPA by blocking the protein-protein interaction between tc-uPA and a protein that can act as a substrate for tc-uPA. As another example, such an antibody may inhibit the activity of tc-uPA by blocking access to the catalytic site of tc-uPA. As another example, such an antibody may inhibit the activity of tc-uPA by inducing a conformational change in tc-uPA that renders the protease less active (i.e. 50%, 60%, 70%, 80%, 85%, 90% or 95% reduction in proteolytic activity relative to a negative control) or inactive, compared to tc-uPA in the absence of the antibody (negative control). As another example, such an antibody may inhibit the activity of tc-uPA by inhibiting the release of substrates that are bound to the catalytic site of tc-uPA.

Previously published and recognised functional assays of measuring the proteolytic activity of uPA include chromogenic and fluorogenic uPA/plasmin substrate-based assays as described in Blouse G E, et al. J Biol Chem. 2009 Feb. 13; 284(7):4647-57. Examples 5, 6, 7, and 8 of the Example section of this specification, describe specific applications of chromogenic assays.

Inhibit/Inhibition/Inhibitory:

The terms "inhibit/inhibition/inhibitory" as used herein refer to a statistically significant reduction in a level of activity or a property, relative to a control.

The antibodies of the invention inhibit proteolytic activity of tc-uPA. Exemplary reductions are from 50 to 100%, and thus include at least 50%, 60%, 70%, 80%, 85%, 90% or 95% reduction in proteolytic activity relative to a negative control, e.g. antibody omission control or isotype-matched irrelevant antibody control. Widely accepted functional assays of measuring proteolytic activity include chromogenic and fluorogenic uPA/plasmin substrate-based assays as described in Blouse G E, et al. J Biol Chem. 2009 Feb. 13; 284(7):4647-57. Examples 5, 6 and 7, of the Example section of this specification, describe specific applications of chromogenic assays. Here the anti-uPA antibodies were tested in several different concentrations within a normal reasonable concentration range to determine $IC_{50}$ values of the level of inhibition, which would always reach 80%-100% at the highest antibody concentrations for inhibiting antibodies.

In one embodiment, the antibodies of the present invention inhibit the proteolytic activity of tc-uPA. In other embodiments, the antibodies of the present invention also inhibit the activation of sc-uPA.

The antibodies of the invention inhibit activation of sc-uPA from a proteolytically inactive form of uPA to a proteolytically active form of uPA. Exemplary reductions are from 50 to 100%, and thus include at least 50%, 60%, 70%, 80%, 85%, 90% or 95% reduction in activation rate relative to a negative control, e.g. relative to antibody omission control or isotype-matched irrelevant antibody control. Functional assays of measuring the activated fraction include chromogenic and fluorogenic uPA substrates as described in Blouse G E, et al. J Biol Chem. 2009 Feb. 13; 284(7):4647-57. Example 8, of the Example section of this specification, describes a specific way of identifying antibodies that inhibit this activation of sc-uPA by measuring the catalytic activity of uPA using a chromogenic uPA substrate. Here the anti-uPA antibodies were tested in several different concentrations within a normal reasonable concentration range to determine $IC_{50}$ values of the level of inhibition, which would always reach 80-100% at the highest antibody concentrations for inhibiting antibodies.

Binding of uPA to uPAR:

In one embodiment, the antibodies of the present invention are capable of binding to both receptor-bound and non-receptor-bound forms of uPA. uPA can bind with sub-nanomolar affinity to the uPA receptor (uPAR or CD87). This interaction is primarily mediated through the GFD domain of uPA. Naturally occurring uPAR is present in several forms. As an example, uPAR can be attached to cell surfaces via a glycosylphosphatidylinositol (GPI) anchor. As another example, several forms of soluble uPAR (suPAR) have been demonstrated, including full-length and truncated forms. As another example, truncated forms of uPAR have been demonstrated, including cell surface-bound forms and soluble forms. The full-length forms of uPAR, including the cell surface-bound full-length form and the soluble full-length form of uPAR have high affinity for uPA. The truncated forms of uPAR have variable affinity for uPA, including high affinity, low affinity, or no significant affinity for uPA.

Receptor-Bound uPA:

The terms 'receptor-bound uPA' and 'uPAR-bound uPA' are used interchangeably herein to denote all forms of uPA that are bound to uPAR or to any variant form of uPAR, including uPAR bound to cell surfaces or present in soluble form. The term receptor-bound uPA furthermore encompasses both sc-uPA and tc-uPA provided that these forms are bound to uPAR. The term receptor-bound uPA furthermore encompasses all structural conformations of uPA provided that these forms are bound to uPAR. The term receptor-bound uPA furthermore encompasses all forms of uPA including active forms of uPA and inactive forms of uPA provided that these forms are bound to uPAR. The term receptor-bound uPA furthermore encompasses uPA from all species including human and other relevant species provided that these forms are bound to uPAR.

Previously published and recognised functional assays of measuring the proteolytic activity of uPAR-immobilized uPA include chromogenic and fluorogenic uPA/plasmin substrate-based assays as described in Blouse G E, et al. J Biol Chem. 2009 Feb. 13; 284(7):4647-57. Example 6 in the Examples section of this specification: 'uPAR receptor immobilized sc-uPA in a coupled zymogen activation assay' describes a specific way of measuring the proteolytic activity of uPAR-immobilized uPA using a chromogenic plasmin substrate. Here, antibodies should be inhibitory even when uPA is bound to uPAR.

Non-Receptor-Bound uPA:

The term 'non-receptor-bound uPA' is used herein to denote all forms of uPA that are not bound to uPAR or to any variant form of uPAR, including uPAR bound to cell surfaces or present in soluble form. The term non-receptor-bound uPA furthermore encompasses both sc-uPA and tc-uPA provided that these forms are not bound to uPAR. The term non-receptor-bound uPA furthermore encompasses all structural conformations of uPA provided that these forms are not bound to uPAR. The term non-receptor-bound uPA furthermore encompasses all forms of uPA including active forms of uPA and inactive forms of uPA provided that these forms are not bound to uPAR. The term non-receptor-bound uPA furthermore encompasses uPA from all species including human and other relevant species provided that these forms are not bound to uPAR.

Method of Identifying Anti-uPA Antibodies:

In one aspect, the present invention provides a method of identifying dual-acting anti-uPA antibodies. The method of identifying anti-uPA antibodies, according to the present invention, comprises the steps of: (a) generating anti-uPA antibodies; (b) identifying antibodies from the antibodies generated in step (a) that inhibit proteolytic activity of tc-uPA; (c) identifying antibodies from the antibodies generated in step (a) that inhibit activation of sc-uPA from a proteolytically inactive form of uPA to a proteolytically active form of uPA; and (d) selecting antibodies that are inhibitory in both steps (b) and (c).

Step (a) of the method of identifying dual-acting anti-uPA antibodies according to the invention, i.e. generating anti-uPA antibodies, can be done according to methods known in the art. For example, anti-uPA antibodies could be generated in, but is not limited to, various animal hosts as well as using phage display, bacterial display, yeast display, mammalian cell display or ribosome or mRNA display. Example 3, of the Example section of this specification describes a specific way of generating anti-uPA antibodies in mice.

Step (b) of the method of identifying dual-acting anti-uPA antibodies according to the invention, i.e. identifying antibodies that inhibit proteolytic activity of tc-uPA, can be done according to methods known in the art. Previously published and recognised functional assays of measuring the proteolytic activity of uPA include chromogenic and fluorogenic uPA/plasmin substrate-based assays as described in Blouse G E, et al. J Biol Chem. 2009 Feb. 13; 284(7):4647-57. Examples 5, 6 and 7, of the Example section of this specification, describe specific applications of chromogenic assays.

Step (c) of the method of identifying dual-acting anti-uPA antibodies according to the invention, i.e. identifying antibodies that inhibit activation of sc-uPA from a proteolytically inactive form of uPA to a proteolytically active form of uPA can be done according to methods known in the art. Previously published and recognised functional assays of measuring the activation of sc-uPA to an active form of uPA include chromogenic and fluorogenic uPA/plasmin substrate-based assays as described in Blouse G E, et al. J Biol Chem. 2009 Feb. 13; 284(7):4647-57. Example 8, of the Example section of this specification, describes a specific way of identifying antibodies that inhibit this activation of sc-uPA by measuring the catalytic activity of uPA using a chromogenic uPA substrate.

Step (d) of the method of identifying dual-acting anti-uPA antibodies according to the invention, i.e. selecting antibodies that are inhibiting in both steps (b) and (c), is done by selecting antibodies that both inhibit the activation of sc-uPA to an active form of uPA, and also inhibit the proteolytic activity of tc-uPA. Only anti-uPA antibodies that inhibit at least 50% of proteolytic activity, (from 50 to 100%, and thus include at least 50%, 60%, 70%, 80%, 85%, 90% or 95% reduction in activation rate relative to a negative control, e.g. antibody omission control or isotype-matched irrelevant antibody control, in step (b) and at least 50% (exemplary reductions are from 50 to 100%, and thus include at least 50%, 60%, 70%, 80%, 85%, 90% or 95% reduction in activation rate relative to a negative control (e.g. antibody omission control or isotype-matched irrelevant antibody control) of activation in step (c) are selected. Examples 5, 6, 7 and 8, in the Example section of this specification, describe a unique way of identifying antibodies that inhibit both the activation of sc-uPA and proteolytic activity of uPA by measuring the catalytic activity of uPA or plasmin using chromogenic substrates for these enzymes.

In one embodiment, the method of identifying dual-acting anti-uPA antibodies according to the invention further comprises the step of identifying anti-uPA antibodies that are inhibitory even when uPA is bound to uPAR. Previously published and recognised functional assays of measuring the proteolytic activity of uPAR-immobilized uPA include chromogenic and fluorogenic uPA/plasmin substrate-based assays as described in Blouse G E, et al. J Biol Chem. 2009 Feb. 13; 284(7):4647-57. Example 6 in the Examples section of this specification: 'uPAR receptor immobilized sc-uPA in a coupled zymogen activation assay' describes a specific way of measuring the proteolytic activity of uPAR-immobilized uPA using a chromogenic substrate for plasmin. Here, antibodies are tested for their ability to inhibit the enzymatic activity of uPA, even when uPA is bound to uPAR.

In another embodiment, the method of identifying dual-acting anti-uPA antibodies according to the invention further comprises the step of inhibiting endogenously derived uPA. In auto-immune or inflammatory diseases or in cancer, immune cells may migrate and infiltrate to the site of inflammation. These cells may play a major role in both the early and late stages of the disease by inflammation of tissues, and uPA may ultimately cause tissue remodelling supporting disease progression. In case of rheumatoid arthritis, macrophages are believed to be pivotal through their endogenous production of uPA. Therefore, the anti-uPA antibodies described in this specification should be able to inhibit uPA produced by macrophages. Example 9 in the Examples section of this specification: Antibodies inhibiting endogenously derived uPA describe a specific and unique way of measuring the proteolytic activity of endogenously derived uPA from M1/M2 macrophages.

In another embodiment, the method of identifying dual-acting anti-uPA antibodies according to the invention further comprises the step of identifying antibodies that, in addition to binding and inhibiting human uPA, also bind and inhibit uPA from other species. It is clearly advantageous to avoid the usage of surrogate antibodies and use the candidate antibody directly for toxicology studies. Previously published and recognised functional assays of measuring the proteolytic activity of human uPA include chromogenic and fluorogenic uPA/plasmin substrate-based assays as described in Blouse G E, et al. J Biol Chem. 2009 Feb. 13; 284(7):4647-57. Example 5, of the Example section of this specification, describes the alternative use of chromogenic assays measuring the proteolytic activity of uPA from the cynomolgus monkey.

Antibodies:

The term "antibody" herein refers to a protein, derived from a germline immunoglobulin sequence, which is capable of binding to an antigen or a portion thereof. The term antibody includes full length antibodies of any class (or isotype), that is, IgA, IgD, IgE, IgG, IgM and/or IgY. An antibody that binds to an antigen, or portion thereof, may bind specifically or exclusively to that antigen, or portion thereof, or it may bind to a limited number of homologous antigens (cross-react), or portions thereof.

In some embodiments of the present invention, the antibodies are capable of binding to and inhibiting human uPA and also capable of binding to and inhibiting uPA from another species, such as other mammalian uPA, such as uPA from a non-human primate (e.g. a chimpanzee, a cynomolgus monkey or a rhesus monkey); a rodent (such as a mouse or a rat), a lagomorph (such as a rabbit), or an artiodactyl (such a cow, sheep, pig or camel).

In a specific embodiment of the present invention, the antibodies are capable of binding to human uPA and also capable of binding to non-human primate uPA (e.g. a chimpanzee, a cynomolgus monkey or a rhesus monkey).

As used herein, the terms "specifically binds" and "specific binding" mean that a the compound, or antibody, exclusively or selectively recognizes and binds a specified epitope, isoform, ortholog (species) or variant of uPA, for example human uPA. The antibodies of the present invention bind to other species of uPA than human (such as cynomolgus monkey) and are therefore not specifically human uPA binding antibodies.

Natural full-length antibodies usually comprise at least four polypeptide chains: two heavy (H) chains and two light (L) chains that are connected by disulfide bonds. In some cases, natural antibodies comprise less than four chains, as in the case of the heavy chain only antibodies found in camelids (VHH fragments) and the IgNARs found in Chondrichthyes. One class of immunoglobulins of particular pharmaceutical interest are the IgGs. In humans, the IgG class may be sub-divided into 4 sub-classes IgG1, IgG2, IgG3 and IgG4, based on the sequence of their heavy chain constant regions. The light chains can be divided into two types, kappa and lambda chains based on differences in their sequence composition. IgG molecules are composed of two heavy chains, interlinked by two or more disulfide bonds, and two light chains, each attached to a heavy chain by a disulfide bond. An IgG heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs) or hypervariable regions (HvRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The variable domains with the hypervariable regions of the heavy and light chains form a [binding] domain that is capable of interacting with an antigen, whilst the constant region of an antibody may mediate binding of the immunoglobulin to host tissues or factors, including, but not limited to various cells of the immune system (effector cells), Fc receptors and the first component (C1q) of the C1 complex of the classical complement system.

Antibodies of the invention may be monoclonal antibodies, in the sense that they represent a set of unique heavy and light chain variable domain sequences as expressed from a single B-cell or by a clonal population of B cells. Antibodies of the invention may be produced and purified using various methods that are known to the person skilled in the art. For example, antibodies may be produced from hybridoma cells. Antibodies may be produced by B-cell expansion. Antibodies or fragments thereof may be recombinantly expressed in mammalian or microbial expression systems, or by in-vitro translation. Antibodies or fragments thereof may also be recombinantly expressed as cell surface bound molecules, by means of e.g. phage display, bacterial display, yeast display, mammalian cell display or ribosome or mRNA display.

Antibodies of the current invention may be isolated. The term "isolated antibody" refers to an antibody that has been separated and/or recovered from (an)other component(s) in the environment in which it was produced and/or that has been purified from a mixture of components present in the environment in which it was produced.

Certain antigen-binding fragments of antibodies may be suitable in the context of the current invention, as it has been shown that the antigen-binding function of an antibody can be performed by fragments of a full-length antibody. The term "antigen-binding fragment" of an antibody refers to one or more fragment(s) of an antibody that retain the ability to bind to an antigen, such as uPA or another target molecule, as described herein. Examples of antigen-binding fragments include Fab, Fab', F(ab)2, F(ab')2, F(ab)S, Fv (typically the VL and VH domains of a single arm of an antibody), single-chain Fv (scFv; see e.g. Bird et al., Science 1988; 242:42S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al. Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 2S:1126-1136; WO2005040219, and published U.S. Patent Applications 20050238646 and 20020161201. These antibody fragments may be obtained using conventional techniques known to those of skill in the art, and the fragments may be screened for utility in the same manner as intact antibodies.

"Fab fragments" of an antibody, including "Fab" and "F(ab')2" fragments, are derived from said antibody by cleavage of the heavy chain in the hinge region on the N-terminal or C-terminal side of the hinge cysteine residues connecting the heavy chains of the antibody. A "Fab" fragment includes the variable and constant domains of the light chain and the variable domain and the first constant domain (CH1) of the heavy chain. "F(ab')2" fragments comprise a pair of "Fab" fragments that are generally covalently linked by their hinge cysteines. A Fab' is formally derived from a F(ab')2 fragment by cleavage of the hinge disulfide bonds connecting the heavy chains in the F(ab')2. Other chemical couplings than disulfide linkages of antibody fragments are also known in the art. A Fab fragment retains the ability of the parent antibody to bind to its antigen, potentially with a lower affinity. F(ab')2 fragments are capable of divalent binding, whereas Fab and Fab' fragments can bind monovalently. Generally, Fab fragments lack the constant CH2 and CH3 domains, i.e. the Fc part, where interaction with the Fc receptors would occur. Thus, Fab fragments are in general devoid of effector functions. Fab fragments may be produced by methods known in the art, either by enzymatic cleavage of an antibody, e.g. using papain to obtain the Fab or pepsin to obtain the F(ab')2, Fab fragments including Fab, Fab', F(ab')2 may be produced recombinantly using techniques that are well known to the person skilled in the art.

An "Fv" fragment is an antibody fragment that contains a complete antigen recognition and binding site, and generally comprises a dimer of one heavy and one light chain variable domain in association that can be covalent in nature, for example in a single chain variable domain fragment (scFv). It is in this configuration that the three hypervariable regions of each variable domain interact to define an antigen-binding site on the surface of the VH-VL dimer. Collectively, the six hypervariable regions or a subset thereof confer antigen binding specificity to the antibody. However, even a single variable domain comprising only three hypervariable regions specific for an antigen can retain the ability to recognize and bind antigen, although usually at a lower affinity than the entire binding site (Cai & Garen, Proc. Natl. Acad. Sci. USA, 93: 6280-6285, 1996). For example, naturally occurring camelid antibodies that only have a heavy chain variable domain (VHH) can bind antigen (Desmyter et al., J. Biol. Chem., 277: 23645-23650, 2002; Bond et al., J. Mol. Biol. 2003; 332: 643-655).

"Single-chain Fv" or "scFv" antibody fragments comprise the VH and VL domains of antibody, where these domains are present in a single polypeptide chain. Generally, the Fv polypeptide further comprises a polypeptide linker between the VH and VL domains that enables the scFv to form the desired structure for antigen binding. For a review of scFv, see Pluckthun, 1994, In: The Pharmacology of Monoclonal Antibodies, Vol. 113, Rosenburg and Moore eds. Springer-Verlag, New York, pp. 269-315.

The term "diabodies" refers to small antibody fragments with two antigen-binding sites, in which fragments comprise a heavy chain variable domain (VH) connected to a light chain variable domain (VL) in the same polypeptide chain (VH and VL). By using a linker that is too short to allow pairing between the two variable domains on the same chain, the variable domains are forced to pair with complementary domains of another chain, creating two antigen-binding sites. Diabodies are described more fully, for example, in EP 404,097; WO 93/11161; and Hollinger et al., 1993, Proc. Natl. Acad. Sci. USA, 90:6444-6448.

The expression "linear antibodies" refers to antibodies as described in Zapata et al., 1995, Protein Eng., 8(10):1057-1062. Briefly, these antibodies contain a pair of tandem Fd segments (VH-CH1-VH-CH1) that, together with complementary light chain polypeptides, form a pair of antigen binding regions. Linear antibodies can be bispecific or monospecific.

The term "monobody" as used herein, refers to an antigen binding molecule with a heavy chain variable domain and no light chain variable domain. A monobody can bind to an antigen in the absence of light chains and typically has three hypervariable regions, for example CDRs designated CDRH1, CDRH2, and CDRH3. A heavy chain IgG monobody has two heavy chain antigen binding molecules connected by a disulfide bond. The heavy chain variable domain comprises one or more hypervariable regions, preferably a CDRH3 or HVL-H3 region.

Antibody fragments may be obtained using conventional recombinant or protein engineering techniques and the fragments can be screened for binding to human uPA, or another function, in the same manner as intact antibodies.

Antibody fragments of the invention may be made by truncation, e.g. by removal of one or more amino acids from the N and/or C-terminal ends of a polypeptide. Fragments may also be generated by one or more internal deletions.

An antibody of the invention may be, or may comprise, a fragment of the mAb 0266-0000-0010 or 0266-0000-0015 antibodies, or variants of these antibodies. An antibody of the invention may be, or may comprise, an antigen binding portion of one of these antibodies, or variants thereof. For example, the antibody of the invention may be a Fab fragment of one of these antibodies or variants thereof, or it may be a single chain antibody derived from one of these antibodies, or a variant thereof.

An antibody of the invention may be a human antibody or a humanised antibody. The term "human antibody", as used herein, is intended to include antibodies having variable regions in which at least a portion of a framework region and/or at least a portion of a CDR region are derived from human germline immunoglobulin sequences. (For example, a human antibody may have variable regions in which both the framework and CDR regions are derived from human germline immunoglobulin sequences.) Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Such a human antibody may be a human monoclonal antibody. Such a human monoclonal antibody may be produced by a hybridoma which includes a B cell obtained from a transgenic nonhuman animal, e.g., a transgenic mouse, having a genome comprising human immunoglobulin heavy and light chain gene segments repertoires, fused to an immortalized cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivative" refers to any modified form of the human antibody, such as a conjugate of the antibody and another agent or antibody.

The term "humanised antibody", as used herein, refers to a human/non-human chimeric antibody that contains a sequence (CDR regions or parts thereof) derived from a non-human immunoglobulin. A humanised antibody is, thus, a human immunoglobulin (recipient antibody) in which at least residues from a hyper-variable region of the recipient are replaced by residues from a hyper-variable region of an antibody from a non-human species (donor antibody) such as from a mouse, rat, rabbit or non-human primate, which have the desired specificity, affinity, sequence composition and functionality. In some instances, FR residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. C. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where reintroduction (backmutation) of the amino acid residue from the donor antibody has beneficial impact on the properties. of the humanised antibody. In addition to donor antibody derived backmutations, the humanised antibody can be engineered by introduction of germline residues in the CDR or framework regions, elimination of immunogenic epitopes, site-directed mutagenesis, affinity maturation, etc.

Furthermore, humanised antibodies may comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and another agent or antibody.

The term "chimeric antibody", as used herein, refers to an antibody whose light and heavy chain genes have been constructed, typically by genetic engineering, from immunoglobulin variable and constant region genes that originate from different species. For example, the variable segments of genes from a mouse monoclonal antibody may be joined to human constant regions.

The fragment crystallizable region ("Fc region"/"Fc domain") of an antibody is the N-terminal region of an antibody, which comprises the constant CH2 and CH3 domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprises one or more, and perhaps all of the following mutations that will result in decreased affinity to certain Fc receptors (L234A, L235E, and G237A) and in reduced C1q-mediated complement fixation (A330S and P331S), respectively (residue numbering according to the EU index).

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CH1 is modified such that the number of cysteine residues in the hinge region is altered, e.g., increased or decreased. This approach is described further for instance in U.S. Pat. No. 5,677,425 by Bodmer et al.

The constant region may be modified to stabilize the antibody, e.g., to reduce the risk of a bivalent antibody separating into two monovalent VH-VL fragments. For example, in an IgG4 constant region, residue S228 (residue numbering according to the EU index) may be mutated to a proline (P) residue to stabilise inter heavy chain disulphide bridge formation at the hinge (see, e.g., Angal et al., Mol Immunol. 199S; 30:105-8).

Antibodies or fragments thereof may also be defined in terms of their complementarity-determining regions (CDRs). The term "complementarity-determining region" or "hypervariable region", when used herein, refers to the regions of an antibody in which amino acid residues involved in antigen binding are situated. The region of hypervariability or CDRs can be identified as the regions with the highest variability in amino acid alignments of antibody variable domains. Databases can be used for CDR identification such as the Kabat database, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196: 901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

An antibody of the invention may comprise a CDR region from one or more of the specific antibodies disclosed herein, such as a CDR regions from anti-uPA antibody 0266-0000-0010 (SEQ ID NOs: 9 to 14) or the VH and VL sequences of anti-uPA antibody 0266-0000-0015 (SEQ ID NOs 5-6) or the VH and VL sequences of humanized anti-uPA antibody hz0266-0000-0010 (SEQ ID NO: 17 and 18), or the Heavy and Light chain sequences of humanized anti-uPA antibody 0266-0000-0043 (SEQ ID NO: 21 and 22).

The term "antigen" (Ag) refers to the molecular entity used for immunisation of an immunocompetent vertebrate to produce the antibody (Ab) that recognizes the Ag. Herein, Ag is termed more broadly and is generally intended to include target molecules that are recognized by the Ab, thus including fragments or mimics of the molecule used in the immunisation process, or other process, e.g. phage display, used for generating the Ab.

Epitope:

The term "epitope", as used herein, is defined in the context of a molecular interaction between an "antigen binding molecule", such as an antibody (Ab), and its corresponding "antigen" (Ag). The term antigen (Ag) may refer to the molecular entity used for immunization of an immunocompetent vertebrate to produce the antibody (Ab) that recognizes the Ag. Generally, "epitope" refers to the area or region on an Ag to which an Ab specifically binds, i.e. the area or region in physical contact with the Ab. Physical contact may be defined through distance criteria (e.g. a distance cut-off of 4 Å) for atoms in the Ab and Ag molecules.

A "discontinuous epitope" is an epitope which is formed by two or more regions of a polypeptide which are not adjacent to each other in the linear peptide sequence, but which are arranged in the three-dimensional structure of the polypeptide to form a structural epitope. Other types of epitopes include: linear peptide epitopes, conformational epitopes which consist of two or more non-contiguous amino acids located near each other in the three-dimensional structure of the antigen; and post-translational epitopes which consist, either in whole or part, of molecular structures covalently attached to the antigen, such as carbohydrate groups.

The epitope for a given antibody (Ab)/antigen (Ag) pair can be defined and characterized at different levels of detail using a variety of experimental and computational epitope mapping methods. The experimental methods include mutagenesis, X-ray crystallography, Nuclear Magnetic Resonance (NMR) spectroscopy and Hydrogen deuterium eXchange Mass Spectrometry (HX-MS), methods that are known in the art. As each method relies on a unique principle, the description of an epitope is intimately linked to the method by which it has been determined. Thus, depending on the epitope mapping method employed, the epitope for a given Ab/Ag pair will be described differently.

At its most detailed level, the epitope for the interaction between the Ag and the Ab can be described by the spatial coordinates defining the atomic contacts present in the Ag-Ab interaction, as well as information about their relative contributions to the binding thermodynamics. At a less detailed level, the epitope can be described by the spatial coordinates defining the atomic contacts between the Ag and Ab. At an even less detailed level the epitope can be described by the amino acid residues that it comprises as defined by a specific criteria such as the distance between atoms in the Ab and the Ag. At a further less detailed level the Ab-Ag interaction can be characterized through function, e.g. by competition binding with other Abs and "binning" although competition binding does not provide any structural information about the epitope.

In the context of an X-ray derived crystal structure defined by spatial coordinates of a complex between an Ab, e.g. a Fab fragment, and its Ag, the term epitope is herein, unless otherwise specified or contradicted by context, specifically defined as uPA residues characterized by having a heavy atom (i.e. a non-hydrogen atom) within a distance of about 3.5 to about 5.0 Å, such as e.g. 4 Å from a heavy atom in the Ab.

From the fact that descriptions and definitions of epitopes, dependant on the epitope mapping method used, are obtained at different levels of detail, it follows that comparison of epitopes for different Abs on the same Ag can similarly be conducted at different levels of detail.

Epitopes described on the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue are shared by the epitopes.

The definition of the term "paratope" is derived from the above definition of "epitope" by reversing the perspective. Thus, the term "paratope" refers to the area or region on the Ab to which an Ag specifically binds, i.e. with which it makes physical contact to the Ag.

In the context of an X-ray derived crystal structure, defined by spatial coordinates of a complex between an Ab, such as a Fab fragment, and its Ag, the term paratope is herein, unless otherwise specified or contradicted by context, specifically defined as Ab residues characterized by having a heavy atom (i.e. a non-hydrogen atom) within a distance of about 4 Å (3.5 to 5.0 Å) from a heavy atom in uPA.

Binding Region:

The term binding region of an antigen refers to a region on an antigen, defined by amino acid sequence, o which one or more antigen binding molecules, such as antibodies bind. A binding region therefore comprises at least one epitope, but can also comprise multiple epitopes of multiple antibodies, both identical epitopes, overlapping epitopes and possible separate epitopes. A binding region can be discontinuous, where it is formed by two or more regions of a the antigen polypeptide which are not adjacent to each other in the linear peptide sequence, but which are arranged in the three-dimensional structure of the polypeptide to form a structural binding region. The binding region can also be linear peptide region on the antigen, or a conformational binding region which consist of two or more non-contiguous amino acids located near each other in the three-dimensional structure of the antigen; and post-translational binding region which consist, either in whole or part, of molecular structures covalently attached to the antigen, such as carbohydrate groups.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques such as surface plasmon resonance (SPR), ELISA or flow cytometry.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope. Competing antibodies, i.e. antibodies belonging to the same "bin" may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes.

The term "binding affinity" is herein used as a measure of the strength of a non-covalent interaction between two molecules, e.g. an antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determining the equilibrium dissociation constant (KD). In turn, KD can be determined by measurement of the kinetics of complex formation and dissociation, e.g. by the SPR method. The rate constants corresponding to the association and the dissociation of a monovalent complex are referred to as the association rate constant ka (or kon) and dissociation rate constant kd (or koff), respectively. KD is related to ka and kd through the equation KD=kd/ka.

Following the above definition, binding affinities associated with different molecular interactions, such as comparison of the binding affinity of different antibodies for a given antigen, may be compared by comparison of the KD values for the individual antibody/antigen complexes.

An antibody according to the current invention may be able to compete with another molecule, such as a naturally occurring ligand or receptor or another antibody, for binding to uPA. Therefore, an antibody according to the current invention may be able to bind uPA with a greater affinity than another molecule also capable of binding uPA. The ability of an antibody to compete with a natural ligand/receptor for binding to an antigen may be assessed by determining and comparing the KD value for the interactions of interest, such as a specific interaction between an antibody and an antigen, with that of the KD value of an interaction not of interest. Typically, the KD for the antibody with respect to the target will be 2-fold, preferably 5-fold, more preferably 10-fold less than KD with respect to the other, non-target molecule such as unrelated material or accompanying material in the environment. More preferably, the KD will be 50-fold less, such as 100-fold less, or 200-fold less; even more preferably 500-fold less, such as 1,000-fold less, or 10,000-fold less.

The value of this dissociation constant can be determined directly by well-known methods. Standard assays to evaluate the binding ability of ligands such as antibodies towards targets are known in the art and include, for example, ELISAs, Western blots, RIAs, and flow cytometry analysis. The binding kinetics and binding affinity of the antibody also can be assessed by standard assays known in the art, such as SPR.

A competitive binding assay can be conducted in which the binding of the antibody to the target is compared to the binding of the target by another ligand of that target, such as another antibody.

The antibodies of the invention, may be capable of competing with antibody 0266-0000-0010 (i.e. antibody or fragment thereof comprising the VH sequence of mAb 0266-0000-0010 (SEQ ID NO: 7) and the VL sequence of mAb 0266-0000-0010 (SEQ ID NO: 8)), or mAb 0266-0000-0015 (i.e. antibody or fragment thereof comprising the VH sequence of mAb 0266-0000-0015 (SEQ ID NO: 5) and the VL sequence of mAb 0266-0000-0015 (SEQ ID NO: 6)) or mAb hz0266-0000-0010 (i.e. antibody or fragment thereof comprising the VH sequence of mAb hz0266-0000-0010 (SEQ ID NO: 17) and the VL sequence of mAb hz0266-0000-0010 (SEQ ID NO: 18)), or mAb 0266-0000-0043 (i.e. an antibody or fragment thereof comprising the Heavy and Light chain sequences of humanized anti-uPA antibody mAb 0266-0000-0043 (SEQ ID NO: 21 and 22)) for binding to human uPA, including sc-uPA and tc-uPA. Antibodies of the invention may be capable of competing with antibody 0266-0000-0010 (i.e. antibody or fragment thereof comprising the VH sequence of mAb 0266-0000-0010 (SEQ ID NO: 7) and the VL sequence of mAb 0266-0000-0010 (SEQ ID NO: 8)), or mAb 0266-0000-0015 (i.e. antibody or fragment thereof comprising the VH sequence of mAb 0266-0000-0015 (SEQ ID NO: 5) and the VL sequence of mAb 0266-0000-0015 (SEQ ID NO: 6)) or mAb hz0266-0000-0010 (i.e. antibody or fragment thereof comprising the VH sequence of mAb hz0266-0000-0010 (SEQ ID NO: 17) and the VL sequence of mAb hz0266-0000-0010 (SEQ ID NO: 18)), or mAb 0266-0000-0043 (i.e. an antibody or fragment thereof comprising the Heavy and Light chain sequences of humanized anti-uPA antibody mAb 0266-0000-0043 (SEQ ID NO: 21 and 22)) for binding to cynomolgus monkey uPA, including sc-uPA and tc-uPA.

An antibody of the invention may have a KD for binding to its target of $1\times10^{-7}$M or less, $1\times10^{-8}$M or less, or $1\times10^{-9}$M or less, or $1\times10^{-10}$M or less, $1\times10^{-11}$M or less, or $1\times10^{-12}$M or less. The KD of an antibody of the current invention may be less than 0.8 nM, such as less than 0.7 nM, such as less than 0.6 nM, such as less than 0.5 nM, such as less than 0.4 nM, such as less than 0.3 nM, such as less than 0.2 nM, such as less than 0.1 nM, such as less than 0.05 nM, such as less than 0.025 nM, such as less than 0.015 nM, such as between 0.015 nM and 0 nM.

The term "identity" as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., Proc. Natl. Acad. Sci USA 89, 10915-10919 (1992) for the BLOSUM 62 comparison matrix) is also used by the algorithm.

Preferred parameters for a peptide sequence comparison include the following: Algorithm: Needleman et al., J. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

The term "similarity" is a related concept, but in contrast to "identity", refers to a sequence relationship that includes both identical matches and conservative substitution matches. If two polypeptide sequences have, for example, (fraction (10/20)) identical amino acids, and the remainder are all non-conservative substitutions, then the percent identity and similarity would both be 50%. If, in the same example, there are 5 more positions where there are conservative substitutions, then the percent identity is 25% and the percent similarity would be 75% ((fraction (15/20))). Therefore, in cases where there are conservative substitutions, the degree of similarity between two polypeptides will be higher than the percent identity between those two polypeptides.

Pharmaceutical Formulations:

In one aspect, the present invention provides compositions and formulations comprising molecules of the invention, such as the anti-uPA antibodies, described herein. For example, the invention provides a pharmaceutical composition that comprises one or more anti-uPA antibodies of the invention, formulated together with a pharmaceutically acceptable carrier.

Accordingly, one object of the invention is to provide a pharmaceutical formulation comprising such an antibody which is present in a concentration from 0.25 mg/ml to 250 mg/ml, and wherein said formulation has a pH from 2.0 to 10.0. The formulation may further comprise one or more of a buffer system, a preservative, a tonicity agent, a chelating agent, a stabilizer, or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, 19th edition, 1995.

In one embodiment, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

Inflammation:

Antibodies that bind uPA as described in the invention may be suitable for use in the treatment of individuals who suffer from an inflammatory condition. Inflammation is the complex biological response of tissues to a variety of stimuli, including but not limited to pathogens, damaged cells, or irritants. Inflammation is a protective response by the organism to remove, neutralize or isolate the injurious stimuli and initiate the healing process. Inflammation is not a synonym for infection—infection is invasion of an organism by an exogenous pathogen, while inflammation is the immune system's response to the pathogen. Accordingly, inflammation is a component of infection, but infection is not necessarily a component of inflammation.

Inflammation is a cascade of events involving multiple components, including the vasculature (e.g., endothelial cells, pericytes, smooth muscle cells), cells of the immune system (e.g., T and B lymphocytes; polymorphonuclear leukocytes or granulocytes, such as monocytes and neutrophils; dendritic cells, macrophages, and NK cells), cell-derived soluble mediators (cytokines, chemokines) and also resident cells in the targeted tissue (e.g., epithelial cells, synovial fibroblasts, neuronal cells). Acute inflammation is of short duration (hours to days) and largely involves resident cells in tissue, migration of cells of the immune system and exudation of fluid and plasma proteins to sites of inflammation. This results from change in vascular flow, cell activation and cellular components that attract cells of the immune system from the circulation into sites of injury. Chronic inflammation is of prolonged duration in which active inflammation, tissue destruction and attempt at repair are proceeding simultaneously. Chronic inflammation can result from persistent infection, prolonged and repeated exposure to toxic agents or due to autoimmunity, a phenomenon by which the body's immune cells attack their own tissues, causing damage.

Normally, the immune system is able to distinguish between the body's normal cells (or "self") and foreign pathogens or abnormal cells ("non-self"). In some instances, the immune system loses the ability to recognize "self" as normal and inappropriately initiates a response against tissue or cells. This response stems from a loss of tolerance to self and is termed "autoimmunity". The pathologies resulting from autoimmunity often have serious clinical consequences and are one of the major health problems in the world, especially in developed nations. Examples of such diseases include inflammatory bowel disease (IBD), Crohns disease (CD), ulcerative colitis (UC), irritable bowel syndrome, rheumatoid arthritis (RA), psoriasis, psoriatic arthritis, systemic lupus erythematosus (SLE), lupus nephritis, type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atoptic dermatitis, vitiligo, graft versus host disease, Sjogrens's syndrome, autoimmune nephritis, Goodpasture's syndrome, chronic inflammatory demyelinating polyneutopathy, allergy, asthma and other autoimmune diseases that are a result of either acute or chronic inflammation.

Targeted biological therapeutics are now available for the treatment of certain autoimmune diseases and/or cancer. For example, patients with cancer may be treated with an antibody against CD20 (anti-CD20); patients with rheumatoid arthritis may be treated with anti-CD20, a TNF antagonist (soluble TNFR or anti-TNF-α); patients with psoriasis may be treated with anti-CD11a; patients with multiple sclerosis may be treated with INF-beta; patients with ulcerative colitis may be treated with anti-TNF-α and patients with Crohn's disease may be treated with anti-TNF-α or anti-α4 integrin. Unfortunately, a large number of patients that receive treatment with any one of these biologics can experience a variety of side-effects, could fail to respond, and/or can develop neutralizing antibodies against the therapeutic medicament. There is still a need for alternative biological medicaments which specifically target pathologies, but that do not affect healthy cells/tissue, resulting in fewer and/or less severe side effects. In addition, such alternative biological medicaments can be used long-term and/or do not result in the generation of neutralizing antibodies. In one aspect, the current invention relates to these unmet needs amongst patients with autoimmune diseases and chronic inflammatory diseases."

Inflammatory Bowel Disease:

Inflammatory Bowel Disease (IBD) is a disease that may affect any part of the gastrointestinal tract from mouth to anus, causing a wide variety of symptoms. IBD primarily causes abdominal pain, diarrhea (which may be bloody), vomiting, or weight loss, but may also cause complications outside of the gastrointestinal tract such as skin rashes, arthritis, inflammation of the eye, fatigue, and lack of concentration. Patients with IBD can be divided into two major classes, those with ulcerative colitis (UC) and those with Crohn's disease (CD). While CD generally involves the ileum and colon, it can affect any region of the intestine but is often discontinuous (focused areas of disease spread throughout the intestine), UC always involves the rectum (colonic) and is more continuous. In CD, the inflammation is transmural, resulting in abscesses, fistulas and strictures, whereas in UC, the inflammation is typically confined to the mucosa. There is no known pharmaceutical or surgical cure for Crohn's disease, whereas some patients with UC can be cured by surgical removal of the colon. Treatment options are restricted to controlling symptoms, maintaining remission and preventing relapse. Efficacy in inflammatory bowel disease in the clinic may be measured as a reduction in the Crohn's Disease Activity Index (CDAI) score for CD which is scoring scale based on laboratory tests and a quality of life questionnaire. In animal models, efficacy is mostly measured by increase in weight and also a disease activity index (DAI), which is a combination of stool consistency, weight and blood in stool.

Multiple Sclerosis:

Multiple sclerosis (MS) is a disease of the central nervous system (CNS) marked by numbness, weakness, loss of muscle coordination and problems with vision, speech, and bladder control. MS is an autoimmune disease in which the body's immune system attacks myelin, a substance that serves as a nerve insulator and helps in the transmission of nerve signals. MS causes demyelinization of the white matter of the brain, with this process sometimes extending into the grey matter. Demyelinization is loss of myelin, which is composed of lipids and protein. When myelin is damaged in MS, nerve fiber conduction is faulty or absent. Impaired bodily functions or altered sensations associated with those demyelinated nerve fibers give rise to the symptoms of MS. There are multiple sub-groups of MS, including relapsing remitting, primary progressive, and secondary progressive. Mouse models representing some of these subtypes are available for testing efficacy of potential therapies. Efficacy in mouse models is measured by a reduction in paralysis in the limbs. Efficacy in patients is measured by a reduced activity score in the brain as measured by MRI and also an improvement in muscle tone/movement.

Genome-wide expression analyses of peripheral blood mononuclear cells (PBMCs) from patients with relapsing—remitting multiple sclerosis (RRMS) revealed that expression of the uPA gene (PLAU) is significantly increased in PBMCs from patients with RRMS compared to PBMCs from healthy controls (Cox et al., Mult Scler 19:1268-74, 2013). In the experimental autoimmune encephalomyelitis (EAE) mouse model of multiple sclerosis, treatment with a uPA-inhibitory PAI-1-derived peptide reduced the disease score (Gur-Wahnon et al., J Neuroinflammation 10:124, 2013).

Psoriasis:

Psoriasis is a T-cell mediated inflammatory disorder of the skin that can cause considerable discomfort. It is a disease for which there is currently no cure and which affects people of all ages. Although individuals with mild psoriasis can often control their disease with topical agents, more than one million patients worldwide require ultraviolet light treatments or systemic immunosuppressive therapy. Unfortunately, the inconvenience and risks of ultraviolet radiation and the toxicities of many therapies limit their long-term use. Moreover, patients usually have recurrence of psoriasis, and in some cases rebound shortly after stopping immunosuppressive therapy. A recently developed model of psoriasis based on the transfer of CD4+ T cells mimics many aspects of human psoriasis and therefore can be used to identify compounds suitable for use in treatment of psoriasis (Davenport et al., Internat. Immunopharmacol 2:653-672, 2002). Efficacy in this model is a measured by reduction in skin pathology using a scoring system. Similarly, efficacy in patients is measured by a decrease in skin pathology.

Psoriatic Arthritis:

Psoriatic arthritis (PsA) is a type of inflammatory arthritis that occurs in a subset of patients with psoriasis. In these patients, the skin pathology/symptoms are accompanied by joint swelling, similar to that seen in rheumatoid arthritis. It features patchy, raised, red areas of skin inflammation with scaling. Psoriasis often affects the tips of the elbows and knees, the scalp, the navel and around the genital areas or anus. Approximately 10% of patients who have psoriasis also develop an associated inflammation of their joints.

Rheumatoid Arthritis:

Rheumatoid arthritis (RA) is a systemic disease that affects nearly if not all of the body and is one of the most common forms of arthritis. It is characterized by inflammation of the joint, which causes pain, stiffness, warmth, redness and swelling. This inflammation is a consequence of inflammatory cells invading the joints, and these inflammatory cells release enzymes that may digest bone and cartilage. As a result, this inflammation can lead to severe bone and cartilage damage and to joint deterioration and severe pain amongst other physiologic effects. The involved joint can lose its shape and alignment, resulting in pain and loss of movement.

There are several animal models for rheumatoid arthritis known in the art. For example, in the collagen-induced arthritis (CIA) model, mice develop an inflammatory arthritis that resembles human rheumatoid arthritis. Since CIA shares similar immunological and pathological features with RA, this makes it a suitable model for screening potential human anti-inflammatory compounds. Efficacy in this model is measured by decrease in joint swelling. Efficacy in RA in the clinic is measured by the ability to reduce symptoms in patients which is measured as a combination of joint swelling, erythrocyte sedimentation rate, C-reactive protein levels and levels of serum factors, such as anti-citrullinated protein antibodies.

Increased levels of uPA have been described in blood, synovial fluid and tissue from patients with RA (Baran et al., J. Cell Mol. Med. 13:3797-3808, 2009; Belcher et al., Ann. Rheum. Dis. 55:230-236, 1996; Busso et al., Ann. Rheum. Dis. 56:550-557, 1997; Ronday et al., Br. J. Rheumatol. 35:416-423, 1996). UPA has been implicated in joint inflammation and arthritic diseases in a number of mouse models. A functional role of uPA in joint inflammation was demonstrated using uPA knock-out mice in the collagen-induced arthritis (CIA) model (Cook et al., Am. J. Pathol. 160:917-926, 2002), in the anti-type II collagen antibody-induced arthritis (CAIA) model (Cook et al., Arthritis Res. Ther. 12:R37, 2010), and in the K/BxN serum transfer arthritis model (De Nardo et al., Arthritis Res. Ther. 12:R199, 2010). In the CIA model, the reduction of arthritic symptoms observed in uPA knock-out mice can be reversed by transplanting wild-type bone marrow, demonstrating that uPA derived from immune cells is crucial for disease progression.

Haemophilic Arthropathy:

Haemophilic arthropathy is a deforming arthritis caused by recurrent bleeding into the joints (haemarthrosis). It is a frequent complication of haemophilia A and B, but may also be seen in other coagulation disorders. Recurrent haemarthroses lead to chronic inflammation of the synovium, cartilage degradation, and bone remodelling. The affected joints are characterized by pain, stiffness, warmth, redness, swelling, and restricted joint movement. The joints most commonly affected are the knees, ankles, elbows, shoulders, and hips.

There are several animal models for haemophilic arthropathy. Some animal models experience spontaneous haemarthrosis, such as haemophilic dogs, whereas other established models are based on artificial induction of joint bleeds, such as the needle-induced knee bleeding model established in haemophilic mice. These animal models may be suitable for screening drug candidates for their effect on haemophilic arthropathy, either by preventing haemarthosis or by attenuating the inflammatory and degradative processes caused by haemarthrosis.

Significantly increased levels of uPA were observed in tissue and synovial fluid from the affected joints in an animal model of haemarthrosis that involves needle-induced knee bleeding in haemophilic mice (Nieuwenhuizen et al., Thromb Haemost 110:173-183, 2013).

Systemic Lupus Erythematosus:

Systemic lupus erythematosus (SLE) is an immune-complex related disorder characterized by chronic IgG antibody production directed at ubiquitous self antigens such as anti-dsDNA. The central mediator of disease in SLE is the production of auto-antibodies against self-proteins/tissues and the subsequent generation of immune-mediated inflammation. Antibodies either directly or indirectly mediate inflammation. Although T lymphocytes are not thought to directly cause disease, they are required for auto-antibody production. The effects of SLE are systemic (e.g., kidney, lung, musculoskeletal system, mucocutaneous, eye, central nervous system cardiovascular system, gastrointestinal tract, bone marrow, blood), rather than localized to a specific organ, although glomerulonephritis may result in some cases (i.e. lupus nephritis). Multiple chromosomal loci have been associated with the disease and may contribute towards different aspects of the disease, such as anti-dsDNA antibodies and glomerulonephritis. Efficacy in SLE in human disease and in appropriate mouse models is measured by the ability of the therapeutic entity to decrease auto-antibodies (Eg: anti-dsDNA) and/or by decrease in renal pathology (enhanced kidney function), leading to amelioration of disease symptoms.

Cancer:

Antibodies that bind uPA as described in the invention may be suitable for use in the treatment of individuals with cancers and other proliferative diseases including, but not limited to: carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma, and multiple myeloma; hematopoietic tumors of myeloid lineage, including acute and chronic myelogenous leukemias, promyelocytic leukemia, and myelodysplastic syndrome; tumors of mesenchymal origin, including fibrosarcoma and rhabdomyoscarcoma; other tumors, including melanoma, seminoma, terato-carcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

Particular disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); adult T-cell leukemia lymphoma (ATLL); T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; lym-phoma/leukaemia (T-Lbly/T-ALL), multiple myeloma.

Other proliferative disorders can also be treated according to the invention, including for example hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

There is still a need for alternative biological medicaments with greater efficacy and/or less severe side effects compared to current treatments. The current invention relates to these unmet needs amongst patients with cancer including patients with metastatic (disseminated) disease.

Increased tissue and plasma levels of uPA have been demonstrated in a number of different cancer forms (Ulisse et al., Current Cancer Drug Targets, 9:32-71, 2009). UPA has also been implicated in cancer and cancer metastasis in a number of mouse models. A functional role of uPA was demonstrated by interfering with uPA mRNA expression (Yu et al., Cancer Res. 50:7623-76331, 1990), by the use of uPA gene-deficient mice (Almholt et al, Int. J. Cancer 113:525-532, 2005), and by applying neutralizing antibodies (Ossowski and Reich, Cell 35:611-619, 1983; Kobayashi et al., Thromb. Haemost. 71:474-480, 1994) or a uPA-specific inhibitor (Schweinitz et al., J. Biol. Chem. 279:33613-33622, 2004; Henneke et al., Am. J. Respir. Crit Care Med. 181:611-619, 2010).

Treatment:

The term "treatment", as used herein, refers to the medical therapy of any human or other animal subject in need thereof. Said subject is expected to have undergone physical examination by a medical or veterinary medical practitioner, who has given a tentative or definitive diagnosis which would indicate that the use of said treatment is beneficial to the health of said human or other animal subject. The timing and purpose of said treatment may vary from one individual to another, according to many factors, such as the status quo of the subject's health. Thus, said treatment may be prophylactic, palliative, symptomatic and/or curative.

In terms of the present invention, prophylactic, palliative, symptomatic and/or curative treatments may represent separate aspects of the invention.

Mode of Action:

An antibody of the invention may be administered parenterally, such as intravenously, such as intramuscularly, such as subcutaneously. Alternatively, an antibody of the invention may be administered via a non-parenteral route, such as perorally or topically. An antibody of the invention may be administered prophylactically. An antibody of the invention may be administered therapeutically (on demand).

Non-Limiting Embodiments

The invention is further described by the following non-limiting embodiments:

1. A monoclonal antibody or antigen-binding fragment thereof that is capable of binding to human uPA characterised in that it inhibits the proteolytic activity of human tc-uPA and inhibits activation of human sc-uPA from a proteolytically inactive form of human uPA to a proteolytically active form of human uPA.
2. A monoclonal antibody or fragment thereof according to embodiment 1, wherein the antibody inhibits both receptor-bound human uPA and non-receptor-bound human uPA.
3. A monoclonal antibody or fragment thereof according to any of embodiments 1 or 2, wherein the antibody also inhibits proteolytic activity of non-human primate tc-uPA, such as cynomolgus monkey tc-uPA.
4. Antibody or fragment thereof according to any of embodiments 1, 2 or 3 wherein the antibody also inhibits activation of non-human sc-uPA such as cynomolgus monkey uPA from a proteolytically inactive form of the non-human uPA to a proteolytically active form of the non-human uPA.
5. An antibody or antigen-binding fragment thereof, according to any of embodiments 1-4, that is capable of binding to human uPA and to uPA from other species, such as chimpanzee, cynomolgus monkey, rhesus monkey, mouse, rat, rabbit, cow, sheep, pig or camel uPA, characterised in that it inhibits the proteolytic activity of tc-uPA, and inhibits activation of sc-uPA from a proteolytically inactive form of uPA to a proteolytically active form of uPA.
6. Antibody or fragment thereof according to embodiments 1-5, wherein the antibody also inhibits endogenously produced/naturally occurring uPA in primary cells.
7. Antibody or an antigen-binding fragment thereof according to any of embodiments 1-6, wherein the antibody inhibits the proteolytic activity of tc-uPA with a reduction in proteolytic activity of 50 to 100%, such as at least 50%, 60%, 70%, 80%, 85%, 90 or 95% reduction in proteolytic activity.
8. Antibody or antigen-binding fragment thereof according to any of embodiments 1-7, wherein the antibody inhibits activation of sc-uPA from a proteolytically inactive form of uPA to a proteolytically active form of uPA with a reduction in activation rate of 50 to 100%, such as at least 50%, 60%, 70%, 80%, 85%, 90 or 95% reduction in activation rate.
9. An antibody or an antigen-binding fragment thereof, according to any of embodiments 1-4, wherein the antibody is a dual-acting anti-uPA antibody, that acts by inducing a conformational change in human uPA (SEQ ID NO:1).
10. An antibody or an antigen-binding fragment thereof, according to embodiment 9, wherein the dual-acting anti-uPA antibody induces a conformational change in any of the amino acids no. 1-33, 67-80, 187-215, 230-234, 243-256, 260-274, 291-306, 322-341, 375-389 and 397-410 of human uPA (SEQ ID NO:1).
11. An antibody or an antigen-binding fragment thereof, according to embodiment 9 or 10, wherein the dual-acting anti-uPA antibody induces a conformational change in any of the amino acids no. 1-33, 67-80, 187-215, 230-234, 243-256, 260-274, 291-306, 322-341, 375-389 and 397-410 of human uPA (SEQ ID NO:1), by binding to the epitope covering Ile167-Ala175 and Tyr218-Leu224 (SEQ ID NO:1).
12. An antibody or antigen-binding fragment thereof, according to any of embodiments 1-4, wherein the heavy chain of said antibody comprises:
a CDR3 sequence of amino acid residues 95 (Kabat; 99 sequential) to 102 (Kabat; 108 sequential) (DGRDG-SWFAY) of SEQ ID NO: 7, wherein one, two or three of these amino acid residues may be substituted by a different amino acid especially where D95 (Kabat; 99 sequential) may be mutated to any amino acid but D, and/or G96 (Kabat; 100 sequential) may be mutated to any amino acid but G, and/or D98 (Kabat; 102 sequential) may be mutated to any amino acid but D, and/or G99 (Kabat; 103 sequential) may mutated to any amino acid but G.
13. An antibody or antigen-binding fragment thereof, according to any of embodiments 1-4 or 12, wherein the heavy chain of said antibody comprises:
a CDR1 sequence of amino acid residues 31 (Kabat and sequential) to 35 (Kabat and sequential) (SYTMS) of SEQ ID NO: 7, wherein one of these amino acid residues may be substituted by a different amino acid residue.
14. An antibody or antigen-binding fragment thereof, according to any of embodiments 1-4 or 12-13, wherein the heavy chain of said antibody comprises:

a CDR2 sequence of amino acids 50 (Kabat and sequential) to 65 (Kabat; 66 sequential) (TISGGGSHIYY-ADSVKG) of SEQ ID NO: 7, wherein one, two or three of these amino acids may be substituted by a different amino acid residue.
15. An antibody or antigen-binding fragment thereof, according to any of embodiments 1-4 or 10-14, wherein the heavy chain of said antibody comprises:
a CDR3 sequence of amino acid residues 95 (Kabat; 99 sequential) to 102 (Kabat; 108 sequential) (DGRDG-SWFAY) of SEQ ID NO: 7.
16. An antibody or antigen-binding fragment thereof, according to any of embodiments 1-4 or 10-14, wherein the heavy chain of said antibody comprises:
a CDR1 sequence of amino acid residues 31 (Kabat and sequential) to 35 (Kabat and sequential) (SYTMS) of SEQ ID NO: 7, and
a CDR2 sequence of amino acids 50 (Kabat and sequential) to 65 (Kabat; 66 sequential) (TISGGGSHIYY-ADSVKG) of SEQ ID NO: 7, and
a CDR3 sequence of amino acid residues 95 (Kabat; 99 sequential) to 102 (Kabat; 108 sequential) (DGRDG-SWFAY) of SEQ ID NO: 7.
17. An antibody or antigen-binding fragment thereof, according to any of embodiments 1-4, wherein the light chain of said antibody comprises:
a CDR1 sequence of amino acid residues 24 (Kabat and sequential) to 34 (Kabat and sequential) (RTSQSIGDYLH) of SEQ ID NO: 8, wherein one, two or three of these amino acid residues may be substituted with a different amino acid.
18. An antibody or antigen-binding fragment thereof, according to any of embodiments 1-4 or embodiment 17, wherein the light chain of said antibody comprises:
a CDR2 sequence of amino acid residues 50 (Kabat and sequential) to 56 (Kabat and sequential) (YVSQSIS) of SEQ ID NO: 8, wherein one or two of these amino acid residues may be substituted with a different amino acid.
19. An antibody or antigen-binding fragment thereof, according to any of embodiments 1-4 or embodiments 17-18, wherein the light chain of said antibody comprises:
a CDR3 sequence of amino acid residues 89 (Kabat and sequential) to 97 (Kabat and sequential) (QNSHSF-PLT) of SEQ ID NO: 8, wherein one or two of these amino acid residues may be substituted with a different amino acid especially N90 may be mutated to any amino acid but N, and/or S91 may be mutated to any amino acid but S.
20. An antibody or antigen-binding fragment thereof, according to any of embodiments 1-4 or embodiments 17-19, wherein the light chain of said antibody comprises:
a CDR1 sequence of amino acid residues 24 (Kabat and sequential) to 34 (Kabat and sequential) (RTSQSIGDYLH) of SEQ ID NO: 8; and
a CDR2 sequence of amino acid residues 50 (Kabat and sequential) to 56 (Kabat and sequential) (YVSQSIS) of SEQ ID NO: 8; and
a CDR3 sequence of amino acid residues 89 (Kabat and sequential) to 97 (Kabat and sequential) (QNSHSF-PLT) of SEQ ID NO: 8.
21. An antibody or antigen-binding fragment thereof, according to any of embodiment 1-4 or 17-19, wherein the light chain of said antibody comprises:
a CDR1 sequence of amino acid residues 24 (Kabat and sequential) to 34 (Kabat and sequential) (RTSQSIGDYLH) of SEQ ID NO: 8; and/or
a CDR2 sequence of amino acid residues 50 (Kabat and sequential) to 56 (Kabat and sequential) (YVSQSIS) of SEQ ID NO: 8; and/or
a CDR3 sequence of amino acid residues 89 (Kabat and sequential) to 97 (Kabat and sequential) (QNSHSF-PLT) of SEQ ID NO: 8, wherein N90 may be mutated to any amino acid but N, and/or S91 may be mutated to any amino acid but S.
22. An antibody or antigen-binding fragment thereof, according to any of embodiments 1-4 or 12-14, wherein the heavy chain of said antibody comprises:
a CDR1 sequence of amino acid residues 31 (Kabat and sequential) to 35 (Kabat and sequential) (SYTMS) of SEQ ID NO: 7; and/or
a CDR2 sequence of amino acids 50 (Kabat and sequential) to 65 (Kabat; 66 sequential) (TISGGGSHIYY-ADSVKG) of SEQ ID NO: 7; and/or
a CDR3 sequence of amino acid residues 95 (Kabat; 99 sequential) to 102 (Kabat; 108 sequential) (DGRDG-SWFAY) of SEQ ID NO: 7, wherein D95 (Kabat; 99 sequential) may be mutated to any amino acid but D, and/or G96 (Kabat; 100 sequential) may be mutated to any amino acid but G, and/or D98 (Kabat; 102 sequential) may be mutated to any amino acid but D, and/or G99 (Kabat; 103 sequential) may be mutated to any amino acid but G.
23. An antibody or antigen-binding fragment thereof, according to any of embodiments 1-4 or 12-22, wherein the heavy chain of said antibody comprises:
a CDR1 sequence of amino acid residues 31 (Kabat and sequential) to 35 (Kabat and sequential) (SYTMS) of SEQ ID NO: 7; and/or
a CDR2 sequence of amino acids 50 (Kabat and sequential) to 65 (Kabat; 66 sequential) (TISGGGSHIYY-ADSVKG) of SEQ ID NO: 7; and/or
a CDR3 sequence of amino acid residues 95 (Kabat; 99 sequential) to 102 (Kabat; 108 sequential) (DGRDG-SWFAY) of SEQ ID NO: 7, wherein D95 (Kabat; 99 sequential) may be mutated to any amino acid but D, and/or G96 (Kabat; 100 sequential) may be mutated to any amino acid but G, and/or D98 (Kabat; 102 sequential) may be mutated to any amino acid but D, and/or G99 (Kabat; 103 sequential) may be mutated to any amino acid but G,
and wherein the light chain of said antibody comprises:
a CDR1 sequence of amino acid residues 24 (Kabat and sequential) to 34 (Kabat and sequential) (RTSQSIGDYLH) of SEQ ID NO: 8; and/or
a CDR2 sequence of amino acid residues 50 (Kabat and sequential) to 56 (Kabat and sequential) (YVSQSIS) of SEQ ID NO: 8; and/or
a CDR3 sequence of amino acid residues 89 (Kabat and sequential) to 97 (Kabat and sequential) (QNSHSF-PLT) of SEQ ID NO: 8, wherein N90 may be mutated to any amino acid but N, and/or S91 may be mutated to any amino acid but S.
24. An antibody or antigen-binding fragment thereof, according to any of embodiments 1-4 or 12-22, wherein the heavy chain of said antibody comprises:
a CDR1 sequence of amino acid residues 31 (Kabat and sequential) to 35 (Kabat and sequential) (SYTMS) of SEQ ID NO: 7; and
a CDR2 sequence of amino acids 50 (Kabat and sequential) to 65 (Kabat; 66 sequential) (TISGGGSHIYY-ADSVKG) of SEQ ID NO: 7; and a CDR3 sequence of amino acid residues 95 (Kabat; 99 sequential) to 102 (Kabat; 108 sequential) (DGRDGSWFAY) of SEQ ID NO: 7;

and wherein the light chain of said antibody comprises:

a CDR1 sequence of amino acid residues 24 (Kabat and sequential) to 34 (Kabat and sequential) (RTSQSIGDYLH) of SEQ ID NO: 8; and a CDR2 sequence of amino acid residues 50 (Kabat and sequential) to 56 (Kabat and sequential) (YVSQSIS) of SEQ ID NO: 8; and a CDR3 sequence of amino acid residues 89 (Kabat and sequential) to 97 (Kabat and sequential) (QNSHSFPLT) of SEQ ID NO: 8.

25. An antibody or antigen-binding fragment thereof, according to embodiments 1-4, wherein the light chain of said antibody comprises SEQ ID NO: 18, wherein V2 (Kabat and sequential) may be mutated to I and/or T22 (Kabat and sequential) may be mutated to S and/or V58 (Kabat and sequential) may be mutated to I and/or T69 (Kabat and sequential) may be mutated to S and/or N90 (Kabat and sequential) may be mutated to any amino acid but N, and/or S91 (Kabat and sequential) may be mutated to any amino acid but S, and the heavy chain of said antibody comprises SEQ ID NO: 17, wherein E1 (Kabat and sequential) may be mutated to D and/or Q3 (Kabat and sequential) may be mutated to K and/or S49 (Kabat and sequential) may be mutated to A and/or A93 (Kabat; 97 sequential) may be mutated to T and/or D95 (Kabat; 99 sequential) may be mutated to any amino acid but D, and/or G96 (Kabat; 100 sequential) may be mutated to any amino acid but G, and/or D98 (Kabat; 102 sequential) may be mutated to any amino acid but D, and/or G99 (Kabat; 103 sequential) may be mutated to any amino acid but G.

26. An antibody or antigen-binding fragment thereof, according to embodiments 1-4 or embodiment 25, wherein the light chain of said antibody comprises SEQ ID NO: 18, wherein V2 (Kabat and sequential) may be mutated to I and/or T22 (Kabat and sequential) may be mutated to S and/or V58 (Kabat and sequential) may be mutated to I and/or T69 (Kabat and sequential) may be mutated to S and/or N90 (Kabat and sequential) may be mutated to any amino acid but N, and/or S91 (Kabat and sequential) may be mutated to any amino acid but S, and combined with Kappa constant part or variants thereof, and the heavy chain of said antibody comprises SEQ ID NO: 17, wherein E1 (Kabat and sequential) may be mutated to D and/or Q3 (Kabat and sequential) may be mutated to K and/or S49 (Kabat and sequential) may be mutated to A and/or A93 (Kabat; 97 sequential) may be mutated to T and/or D95 (Kabat; 99 sequential) may be mutated to any amino acid but D, and/or G96 (Kabat; 100 sequential) may be mutated to any amino acid but G, and/or D98 (Kabat; 102 sequential) may be mutated to any amino acid but D, and/or G99 (Kabat; 103 sequential) may be mutated to any amino acid but G, and combined with IgG1 or a variant of IgG1 or IgG2 or a variant of IgG2 or IgG4 or a variant of IgG4 constant part.

27. A humanized antibody or antigen-binding fragment thereof, according to any of embodiments 1-4 or 12-24, wherein the variable heavy chain comprises SEQ ID NO:17 and/or the variable light chain comprises SEQ ID NO:18.

28. A humanized antibody or antigen-binding fragment thereof, according to any of embodiments 1-4 or 12-24, that is capable of binding uPA, wherein the heavy chain comprises SEQ ID NO:21 and/or the light chain comprises SEQ ID NO:22.

29. A humanized antibody or antigen-binding fragment thereof, according to any of embodiments 1-4 or 12-24, wherein the heavy chain comprises:

a CDR-H1 comprising SEQ ID NO: 9, located in amino acid residues 31-35 (Kabat); and/or a CDR-H2 comprising SEQ ID NO: 10, located in amino acid residues 50-65 (Kabat); and/or a CDR-H3 comprising SEQ ID NO: 11, located in amino acid residues 95-102 (Kabat).

30. A humanized antibody or antigen-binding fragment thereof, according to any of embodiments 1-4, 12-24 or 29, wherein the light chain comprises:

a CDR-L1 comprising SEQ ID NO: 12, located in amino acid residues 24-34 (Kabat); and/or a CDR-L2 comprising SEQ ID NO: 13, located in amino acid residues 50-56 (Kabat); and/or a CDR-L3 comprising SEQ ID NO: 14, located in amino acid residues 89-97 (Kabat).

31. A humanized antibody or antigen-binding fragment thereof, according to any of embodiments 1-4 or 29-30, wherein the heavy chain comprises:

a CDR-H1 comprising SEQ ID NO: 9, located in amino acid residues 31-35 (Kabat); and a CDR-H2 comprising SEQ ID NO: 10, located in amino acid residues 50-65 (Kabat); and a CDR-H3 comprising SEQ ID NO: 11, located in amino acid residues 95-102 (Kabat)

and wherein the light chain comprises:

a CDR-L1 comprising SEQ ID NO: 12, located in amino acid residues 24-34 (Kabat); and a CDR-L2 comprising SEQ ID NO: 13, located in amino acid residues 50-56 (Kabat); and a CDR-L3 comprising SEQ ID NO: 14, located in amino acid residues 89-97 (Kabat).

32. An antigen or antigen-binding fragment thereof, according to any of embodiments 1-11, that competes with the antibody of embodiment 22 in binding to human uPA (SEQ ID NO 1) or cynomolgus monkey uPA (SEQ ID NO 3).

33. An antigen or antigen-binding fragment thereof, according to any of embodiments 1-11, that competes with the antibody of embodiment 23 in binding to human uPA (SEQ ID NO 1) or cynomolgus monkey uPA (SEQ ID NO 3).

34. An antigen or antigen-binding fragment thereof, according to any of embodiments 1-11, that competes with the antibody of embodiment 26 in binding to human uPA (SEQ ID NO 1) or cynomolgus monkey uPA (SEQ ID NO 3).

35. An antigen or antigen-binding fragment thereof, according to any of embodiments 1-11, that competes with the antibody of embodiment 27 in binding to human uPA (SEQ ID NO 1) or cynomolgus monkey uPA (SEQ ID NO 3).

36. An antigen or antigen-binding fragment thereof, according to any of embodiments 1-11, that competes with the antibody of embodiment 30 in binding to human uPA (SEQ ID NO 1) or cynomolgus monkey uPA (SEQ ID NO 3).

37. An antibody or antigen-binding fragment thereof, according to any of embodiments 1-11, that binds to a discontinuous epitope/binding region on human uPA (SEQ ID NO:1), wherein the first binding part of the discontinuous epitope/binding region is defined by amino acids no. 167-175 of SEQ ID NO:1, and the second binding part of the discontinuous epitope/binding region is defined by amino acids no. 218-224 of SEQ ID NO:1.

38. An antibody or antigen-binding fragment thereof, according to embodiments 1-11, that binds to one or more amino acids of the first binding part of a discontinuous epitope/binding region on human uPA (SEQ ID NO:1), wherein the first binding part of the discontinuous epitope/binding region is defined by amino acids no. 167-175 of SEQ ID NO:1, and to one or more amino acids on the second binding part of the discontinuous epitope/binding region, wherein the second binding part is defined by amino acids no. 218-224 of SEQ ID NO:1.

39. An antibody or antigen-binding fragment thereof, according to any of embodiments 1-11, that binds to a discontinuous epitope/binding region on human uPA (SEQ ID NO:1), wherein said binding region comprises one or more (preferably two or more, preferably three or more, preferably four or more, preferably five or more, preferably six or more, preferably seven or more, preferably eight or more, preferably all nine of the following amino acids of SEQ ID NO 1: Ile 167, Glu 168, Asn 169, Gln 170, Pro 171, Trp 172, Phe 173, Ala 174 and Ala 175, and one or more (preferably two or more, preferably three or more, preferably four or more, preferably five or more, preferably 6 or more, preferably all seven of the following amino acids of SEQ ID NO:1: Tyr 218, Leu 219, Gly 220, Arg 221, Ser 222, Arg 223 and Leu 224.

40. An antibody or antigen-binding fragment thereof, that competes with the antibody of embodiments 23, 24, 27, 28 or 31, in binding to a discontinuous epitope/binding region on human uPA (SEQ ID NO:1), wherein the first binding part of the discontinuous epitope/binding region is defined by amino acids no. 167-175 of SEQ ID NO:1, and the second binding part of the discontinuous epitope/binding region is defined by amino acids no. 218-224 of SEQ ID NO:1.

41. Antibody or fragment thereof according to any of the preceding embodiments, wherein the antibody is selected from the group consisting of a monoclonal antibody, a human antibody, a humanized antibody, a chimeric antibody, an antigen binding region of a human antibody, an scFv, a Fab, a F(ab')2, an Fv, and a single chain antibody.

42. Antibody or fragment thereof according to any of the preceding embodiments, wherein the antibody or fragment thereof is an antigen-binding fragment selected from the group consisting of:
Fab, Fab', F(ab)2, F(ab')2, F(ab)S, Fv, single-chain, dsFv, Fd, and dAb fragments; VH, VL, VhH, and V-NAR domains; monovalent molecules comprising a single VH and a single VL chain; minibodies, diabodies, triabodies, tetrabodies, and kappa bodies; camel IgG; IgNAR; as well as one or more isolated CDRs or a functional paratope, where the isolated CDRs or antigen-binding residues or polypeptides can be associated or linked together so as to form a functional antibody fragment.

43. Antibody or fragment thereof according to any of the preceding embodiments, wherein the antibody is conjugated to a therapeutic agent.

44. Antibody or fragment thereof according to any of the preceding embodiments, for use as a medicament.

45. Antibody or fragment thereof according to any one of the preceding embodiments for the manufacture of a medicament for the treatment of an autoimmune disease and/or chronic inflammation.

46. Antibody or fragment thereof according to any one of the preceding embodiments for use in the treatment of a cancer disease, and/or an autoimmune disease and/or chronic inflammation.

47. Antibody or fragment thereof according to embodiments 44-46 for use in the treatment of rheumatoid arthritis.

48. A method of treating an autoimmune disease or a chronic inflammatory disease which comprises administering an antibody or fragment thereof according to any one of the preceding embodiments to a subject in need thereof.

49. Pharmaceutical composition that comprises one or more anti-uPA antibodies or fragments thereof according to any one of embodiments 1-48, formulated together with a pharmaceutically acceptable carrier.

50. Method of identification of anti-uPA antibodies comprising the steps of: (a) generating anti-uPA antibodies; (b) identifying antibodies from the antibodies generated in step (a) that inhibit proteolytic activity of human tc-uPA; (c) identifying antibodies from the antibodies generated in step (a) that inhibit activation of human sc-uPA from a proteolytically inactive form of human uPA to a proteolytically active form of human uPA; and (d) selecting antibodies that are inhibiting in both steps (b) and (c).

51. Method according to embodiment 50, wherein the method further comprises the step of identifying anti-uPA antibodies that are inhibitory even when human uPA is bound to human uPAR.

52. Method according to embodiment 50, wherein the method further comprises the step of identifying anti-uPA antibodies that inhibit endogenously derived human uPA.

53. Method according to embodiment 50, wherein the method further comprises the step of identifying anti-uPA antibodies that also bind and inhibit uPA from other species such as chimpanzee, cynomolgus monkey, rhesus monkey, mouse, rat, rabbit, cow, sheep, pig or camel uPA.

54. Method of producing an antibody or antigen-binding fragment thereof that is capable of binding to human uPA, wherein the antibody is identified according to the method of identification according to any of embodiments 50-53.

EXAMPLES

Example 1: Production of Human sc-uPA

For expression of recombinant human sc-uPA (SEQ ID NO: 1), the full length cDNA sequence was synthesized (SEQ ID NO: 2) and cloned into a mammalian expression construct with CMV promoter by standard techniques. The generated expression plasmid was denoted as pJSV-human pro-uPA. All constructs were verified by DNA sequencing. In the cDNA sequence of human sc-uPA (SEQ ID NO 2), the nucleotide sequence encoding the mature sc-uPA protein is preceded by nucleotide sequence encoding a 20 amino acid signal peptide [MRALLARLLLCVLVVSDSKG]. This signal peptide is not present in the mature human sc-uPA protein.

Recombinant wild-type human sc-uPA proteins was expressed in human embryonic kidney 293 cells (HEK293) by transient transfection, using 293Fectin™ Transfection Reagent (Life Technologies—Invitrogen, Carlsbad, Calif., USA). The cell culture medium was harvested 72 hours after transfection.

The recombinant wild type sc-uPA protein was purified by Q chromatography in flow through mode and SP purification process, and an additional Superdex75 as a polish step. The final protein products have the purity >95% (estimated by SDS-PAGE, Bioanalyzer CE and SEC-HPLC) and endotoxin <1 EU/mg (assessed by Kinetic turbidimetric test).

Example 2: Production of Cynomolgus sc-uPA

For expression of recombinant cynomolgus sc-uPA (SEQ ID NO: 3), the full length cDNA sequence was synthesized (SEQ ID NO: 4) and cloned into expression vector pcDNA3.1+ (Invitrogen, Carlsbad, Calif., USA) with a 6×His tag at C-terminus (by standard techniques. The generated expression plasmid was denoted as pcDNA3.1-cyno pro-uPA-6×His. In the cDNA sequence of cynomolgus sc-uPA (SEQ ID NO: 4), the nucleotide sequence encoding the mature sc-uPA protein is preceded by nucleotide sequence encoding a signal peptide that based on homology between the human and cynomolgus sequences is predicted to be 20 amino acids long [MRALLAHLLLCVLVVSDSKS]. The exact identity of the signal peptide for cynomolgus sc-uPA has not been established. The signal peptide is not present in the mature cynomolgus sc-uPA protein.

Recombinant cynomolgus sc-uPA protein was expressed in HEK293 cells by transient transfection, using 293Fectin™ Transfection Reagent (Life Technologies—Invitrogen, Carlsbad, Calif., USA), with presence of 10 µg/mL aprotinin (Petersen H H, et al. Eur J Biochem. 2001 August; 268(16): 4430-9; Blouse G E, et al. J Biol Chem. 2009 Feb. 13; 284(7):4647-57 in culture medium (Roche Applied Science, Mannheim Germany) to prevent proteolytic cleavage at the activation site. The cell culture medium was harvested 24 hours after transfection.

The recombinant cynomolgus sc-uPA protein was purified by Nickel column and followed by Superdex_75 purification. Nickel column purification was conducted with presence of 10 µg/mL aprotinin. The buffer of Superdex_75 and final storage buffer is 20 mM NaAc, 150 mM NaCl, pH 5.0 (Lin L, et al. J Biol Chem. 2010 Apr. 2; 285(14):10982-92), to prevent spontaneous activation. The final protein products have the purity >90% (estimated by SDS-PAGE, Bioanalyzer CE and SEC-HPLC) and endotoxin <1 EU/mg (assessed by Kinetic turbidimetric test).

Example 3: Generation of Monoclonal Anti-uPA Antibodies

In order to generate mouse monoclonal antibodies (mAb) RBF mice were immunised with recombinant human sc-uPA (SEQ ID NO: 1).

Mice were immunised subcutaneously. For the first immunisation, 20 µg of antigen was mixed with complete Freund's adjuvant. In subsequent immunisations incomplete Freund's adjuvant was used with the same amount of antigen. Ten days after the last immunisation, eye-blood from the mice was analysed by ELISA for uPA-specific antibodies. Mice with positive titers were boosted intravenously with 10 µg antigen in PBS, and sacrificed after three days. The spleens were aseptically removed and dispersed into a single cell suspension. Fusion of spleen cells and myeloma cells was performed by electrofusion. Hybridomas secreting specific antibodies were selected using a specific binding assay as described in example 5.

Example 4: Primary Screening for Antibodies Binding to Human sc-uPA

Immunoplates (Maxisorb, Nunc) were coated with 2 µg/ml recombinant human sc-uPA. A 1:1 vol. ratio of 20 µg/ml aprotinin in PBS and hybridoma culture supernatant, were added to the plates and incubated at room temperature for one hour. Detection was done with a HRP-conjugated polyclonal antibody (pAb) specific to murine antibodies.

Example 5: The Coupled Zymogen Activation Assay uPA converts the zymogen plasminogen to the active plasmin. In turn, a positive feedback loop exists, in which plasmin also activates sc-uPA to tc-uPA, thus enhancing the reaction kinetics.

We adapted this assay from Blouse et al. 2009 (Blouse G E, et al. J Biol Chem. 2009 Feb. 13; 284(7):4647-57), and used it to identify anti-uPA antibodies that inhibit the activation of sc-uPA and/or inhibit the catalytic activity of tc-uPA. Briefly, 10 µL of hybridoma culture supernatant containing the anti-uPA test antibody was incubated with 40 µL of recombinant human sc-uPA (SEQ ID NO: 1) to a final concentration of 0.625 nM in HBS-B buffer (30 mM HEPES, 135 mM NaCl, 1 mM EDTA, 0.1% BSA, pH 7.4) in a microtiter plate (Perkin Elmer, #6005659) at room temperature for 30 min. No significant interference of the supernatants on the assay kinetics was observed, which allowed the screening of non-purified antibodies directly from crude culture supernatant. After incubation, 50 µL was added of a mix containing human plasminogen (american diagnostica inc, #400) to a final concentration of 0.5 µM and the chromogenic plasmin substrate H-D-Val-Leu-Lys-p-nitroanilide (Chromogenix, #820332) named S-2251 at a final concentration of 0.5 mM. The S-2251 hydrolysis was recorded for the parabolic increase in absorbance at 405 nm over a time course of three hours. The absorbance was used as a measure of plasmin activity which is an indirect measure of uPA activity. Antibodies resulting in low or even absent absorbance were identified as functionally inhibiting human uPA, and were included for further testing in a modified version of this assay using recombinant sc-uPA from cynomolgus (cyno) monkeys instead of human sc-uPA. All other components and assay steps are the same to what is described above. Antibodies capable of functionally inhibiting cyno uPA were selected for further characterization. Purified batches of the selected antibodies were used to determine $IC_{50}$ values of inhibition (Table 9).

The 0266-000-0010 antibody tested in the assay with sc-uPA from cynomolgus monkey (SEQ. ID NO: 3) resulted in an $IC_{50}$ value of 0.9 nM, showing that this antibody can also effectively neutralize sc-uPA from cynomolgus monkey.

Example 6: uPAR Receptor Immobilized sc-uPA in a Coupled Zymogen Activation Assay Human uPA naturally binds to its cognate uPA receptor (uPAR). A functional assay was used in which human sc-uPA immobilized on human uPAR was tested for its ability to activate human plasminogen to plasmin. This enabled the selection of functional antibodies that do not compete with the binding of uPAR to uPA, and are thus able to functionally inhibit both receptor-bound and non-receptor-bound uPA. Briefly, U937 cells that were shown to express uPAR on the cell surface were washed in HBS-B buffer, and then treated with glycin buffer (pH 3.0) for three min to strip endogenously bound uPA. The low pH was then neutralized with HEPES buffer (500 mM HEPES, 100 mM NaCl, pH 7.5). The cells were resuspended in HBS-B buffer at $10 \times 10^6$ cells/mL, and incubated with 12.5 nM recombinant human sc-uPA (SEQ ID NO: 1) at room temperature for one hour. The cells were washed three times with HBS-B buffer to remove unbound sc-uPA, and then 25 μL, corresponding to 0.25×10⁶ cells, were distributed in the wells in a 96-well microtiter plate (Perkin Elmer, #6005659), and incubated with 25 μL of hybridoma culture supernatant containing the anti-uPA test antibody at room temperature for 30 min. After incubation, 50 μL was added of a mix containing human plasminogen (american diagnostica inc, #400) to a final concentration of 0.5 μM and the chromogenic plasmin substrate H-D-Val-Leu-Lys-p-nitroanilide (Chromogenix, #820332) named S-2251 at a final concentration of 0.5 mM. The S-2251 hydrolysis was monitored real-time for the parabolic increase in absorbance at 405 nm over a time course of three hours. The absorbance was used as a measure of plasmin activity which is an indirect measure uPA activity while bound to uPAR. For reference, both 0266-0000-0010 and 0266-0000-0015 and also the humanized antibody 0266-0000-0043 inhibited the activity of human uPA (SEQ ID NO: 1) with $IC_{50}$ values <0.7 nM in this assay. Antibodies resulting in low or even absent absorbance were identified as functionally capable of inhibiting human uPA while immobilized on uPAR, and were selected for further testing.

Example 7: Identification of Anti-Catalytic Anti-uPA Antibodies

An assay measuring tc-uPA-catalyzed conversion of plasminogen to plasmin was used to determine if the functionally neutralizing antibodies selected in the coupled zymogen activation assay (see Example 5) would inhibit the catalytic activity of human tc-uPA. Briefly, 10 μL of hybridoma culture supernatant containing the anti-uPA test antibody was preincubated with 40 μL of recombinant human tc-uPA (R&D Systems, #1310-SE) to a final concentration of 0.6 nM in HBS-B buffer (30 mM HEPES, 135 mM NaCl, 1 mM EDTA, 0.1% BSA, pH 7.4) in a microtiter plate (Perkin Elmer, #6005659) at room temperature for 30 min. No significant interference of the supernatants on the assay kinetics was observed, which allowed the screening of non-purified antibodies directly from crude culture supernatant. After incubation, 50 μL was added of a mix containing human plasminogen (american diagnostica inc #400) to a final concentration of 0.5 μM and the chromogenic plasmin substrate H-D-Val-Leu-Lys-p-nitroanilide (Chromogenix, #820332) named S-2251 at a final concentration of 0.5 mM. The S-2251 hydrolysis was monitored real-time for the parabolic increase in absorbance at 405 nm over a time course of three hours. The absorbance was used as a measure of plasmin activity which is an indirect measure of the tc-uPA catalytic activity in the conversion of plasminogen to plasmin. Antibodies capable of neutralizing the catalytic activity of human tc-uPA were selected for further screening. Purified batches of the selected antibodies were used to determine $IC_{50}$ values of inhibition (Table 9).

Example 8: Identification of Anti-uPA Antibodies that Inhibit Activation of sc-uPA from an Inactive Form to an Active Form To determine if the functionally neutralizing anti-uPA antibodies identified in the coupled zymogen activation assay (see Example 5) are able to inhibit activation of human sc-uPA from an inactive form to an active form of uPA they were further tested in an activation assay, in which human sc-uPA is activated from an inactive form to an active form by plasmin. Briefly, 10 μL of hybridoma culture supernatant containing the anti-uPA test antibody was preincubated with 40 μL of recombinant human sc-uPA (SEQ ID NO: 1) to a final concentration of 6.4 nM in a microtiter plate (Perkin Elmer, #6005659) in HBS-B buffer (30 mM HEPES, 135 mM NaCl, 1 mM EDTA, 0.1% BSA, pH 7.4) at room temperature for 30 min. After incubation, 50 μL was added of a mix containing human plasmin (Raybiotech, Inc, # MD-14-0070P) to a final concentration of 5 nM and the chromogenic uPA substrate <Glu-Gly-Arg-p-nitroanilide (Chromogenix, #S-2444) named S-2444 at a final concentration of 0.5 mM. The S-2444 hydrolysis was recorded for the parabolic increase in absorbance at 405 over a time course of three hours. The absorbance was used as a direct measure of the active form of human uPA.

Selection and Characterisation of Dual-Acting Antibodies

Antibodies that inhibited uPA including receptor-bound uPA (see Examples 5 and 6) and were found to have both anti-activation (see Example 8) and anti-catalytic capability (see Example 7) were defined as dual-acting and selected for further characterization. Purified batches of the selected antibodies were used to determine IC50 values of inhibition of the assays described in Examples 5, 7, and 8 (see Table 9).

Example 9: Antibodies Functionally Inhibiting Endogenously Derived uPA

To assess whether the selected dual-acting anti-uPA monoclonal antibodies are able to functionally inhibit endogenously derived uPA we established an assay, in which the activity of human M1 and M2 macrophage-derived uPA could be measured. Briefly, macrophages were matured to M1 and M2 from monocytes isolated from human buffy coats. The cells were washed and resuspended in RM buffer (0.4 mM $MgSO_4$, 0.5 mM $MgCl_2$, 0.5 mM $CaCl_2$, 20 mM HEPES, 0.01% BSA, pH 7.4). Forty microliter corresponding to 0.5×10⁶ cells were added per well in a 96-well microtiter plate (Perkin Elmer, #6005659), and 10 μL of purified anti-uPA test antibody was added, and the reaction was incubated at room temperature for 30 min. After incubation, 50 μL was added of a mix containing human plasminogen (american diagnostica inc, #400) to a final concentration of 0.5 μM and the chromogenic plasmin substrate H-D-Val-Leu-Lys-p-nitroanilide (Chromogenix, #820332) named S-2251 at a final concentration of 0.5 mM. The S-2251 hydrolysis was recorded for the parabolic increase in absorbance at 405 nm in a 96-well microtiter plate over a time course of three hours. The absorbance was used as a measure of plasmin activity which is an indirect measure uPA activity derived from the macrophages. For reference, 0266-0000-0010 inhibited uPA with an $IC_{50}$ of 1.3 nM, and 0266-0000-0015 with an $IC_{50}$<0.7 nM in this assay. Importantly, the humanized antibody, 0266-0000-0043, was also able to inhibit uPA activity derived from macrophages with an $IC_{50}$ of 2.1 nM. The dual-acting antibodies capable of inhibiting uPA from the M1 and M2 macrophages were selected as candidates to treat rheumatoid arthritis, since macrophages are believed to play a major role in the development of the disease.

Example 10: Binding to Human In Vitro Generated Macrophages, Analysed by Flow Cytometry Material and Methods: Buffy Coats were obtained from normal healthy volunteers from Copenhagen University Hospital. Monocytes were isolated using Human Monocyte Enrichment Coctail Rosette Separation. Purified monocytes were cultured for 6 days, in the presence of 40 ng/ml rhM-CSF, at 37° C., 5% $CO_2$. The media was replaced at day 3 with fresh media containing 40 ng/ml rhM-CSF. On day 6 the media was changed again to culture media containing rhIFN-gamma (50 ng/ml) and the cells were further incubated overnight in order to differentiate the cells to M1 macrophages. The cells were stained with 10, 1 or 0.1 µg/ml of the anti-uPA mAb clones 0266-0000-0010 (IgG1) or 0266-0000-0015 (IgG1). A mouse IgG1 isotype control (10 µg/ml) was used as negative control. A secondary APC-conjugated goat-anti-mouse IgG was used for detection. Flow cytometric analysis was performed on a BD FACS Fortessa (Becton & Dickinson).

Results: Both the anti-uPA monoclonal antibody clones (0266-0000-0010 and 0266-0000-0015) demonstrated binding to the M1 macrophages (FIG. 1). Both antibodies showed a dose-dependent binding with similar potency, although slightly higher MFI values were recorded for 0266-0000-0015, indicating somewhat higher affinity (Table 1). This is in agreement with affinity data generated by Biacore analysis. The isotype control antibody (mouse IgG1) showed only low background staining at 10 µg/ml.

TABLE 1

MFI values for M1 macrophages stained with two different clones of uPA mAbs

| uPA antibodies | Mean fluorescence intensity (MFI) | | | |
| --- | --- | --- | --- | --- |
| | Unstained | 0.1 µg/ml | 1 µg/ml | 10 µg/ml |
| 0266-0000-0010 | 685 | 2165 | 3882 | 6919 |
| 0266-0000-0015 | 685 | 4196 | 6181 | 7976 |

Table 1 shows mean fluorescence intensity (MFI) values for M1 macrophages stained with the two different clones of uPA antibodies.

Example 11: Determination of the Antigen Binding Affinity

Affinities of the anti-uPA mAbs towards human and cynomolgus sc-uPA (SEQ ID NO: 1 and 3) were measured by SPR using a Biacore T200 instrument (GE Healthcare). These studies were performed using a direct binding procedure. The respective antibodies were covalently coupled via free amine groups to the carboxy methylated dextran membrane (CM5/CM4) on the sensor chip surface, to a level of 300-500 Resonance Units (RU). sc-uPA in HBS-B (300 mM Hepes, 135 mM NaCl, 1 mM EDTA and 1% BSA, pH 7.4) was injected in various concentrations, followed by a dissociation period with constant buffer flow over the sensor chip surface. Injection time was 60 sec., followed by 180 sec. dissociation. Regeneration was performed by injection of two short pulses of glycine-HCl pH 1.5.

The kinetic parameters ($k_a$, $k_d$ and $K_D$) for the interaction were calculated using a 1:1 interaction Langmuir fitting model.

The measured affinities were all in the low nM range.

Kinetic parameters for the interaction between human or cynomolgus sc-uPA to immobilized mAbs 0266-0000-0010 and 0266-0000-0015 measured by SPR analysis. Results are shown in Table 2 Association rate constant (ka) and Dissociation rate constant (kd) were measured. Equilibrium dissociation constant is calculated as KD=kd/ka.

TABLE 2

Kinetic parameters for the interaction between sc-uPA to two different uPA mAbs

| mAb | Analyte | ka (1/Ms) | kd (1/s) | KD (M) |
| --- | --- | --- | --- | --- |
| 0266-0000-0010 | human sc-uPA | 3.40E+05 | 3.45E−04 | 1.02E−09 |
| 0266-0000-0010 | cynomolgus sc-uPA | 4.73E+05 | 5.74E−05 | 1.21E−10 |
| 0266-0000-0015 | human sc-uPA | 1.03E+06 | 3.81E−04 | 3.70E−10 |
| 0266-0000-0015 | cynomolgus sc-uPA | 1.35E+06 | 7.17E−03 | 5.32E−09 |

Example 12: Cloning and Sequencing of Anti-uPA mAb VL and VH cDNAs from Hybridoma Total RNA was extracted from two different anti-uPA mAb expressing hybridomas designated: m-uPA-1F21A1 and m-uPA-1F58A1 expressing the antibodies 0266-0000-0010 and 0266-0000-0015, respectively. The RNA was extracted from hybridoma cells using RNeasy mini kit (Qiagen, cat. no. 74106) and an aliquot of the resulting RNA was used as template for first-stranded cDNA synthesis using SMARTer RACE cDNA Amplification kit (Clontech, cat. no. 634923) following the instruction of the manufacturer for 5' RACE and using 5' RACE CDS primer A together with SMARTer II A oligonucleotide. The light chain variable domain (VL) and heavy chain variable domain (VH) coding region cDNAs from each of the two anti-uPA hybridomas were hereafter PCR amplified using Universal primer A mix (UPM) together with either a mouse LC,kappa specific reverse primer (5' gga get ggt ggt ggc atc tca gga cct ttg 3') or together with a reverse primer recognizing mouse IgG1 sequences (5' aaaaa tctagaATA GAC AGA TGG GGG TGT CGT TTT GGC 3'). The PCR reactions were performed using phusion PCR mix (FinnZymes, cat no.: F-531 L). The resulting PCR fragments were cloned using Zero blunt Topo PCR cloning kit (Invitrogen, cat. no. K280040) and sequenced.

Example 13: Humanisation Model for Anti-uPA Antibodies

The sequence of 0266-0000-0010 was obtained from cloning of the hybridoma 1F21A1 as described in Example 12 and the variable parts of the heavy and light chains are listed in Table 3. Here the full 0266-0000-0010VH is given in SEQ ID NO: 7 and the CDRs according to the Kabat CDR definitions are given in SEQ ID NO: 9, SEQ ID NO: 10 and SEQ ID NO: 11 respectively. Further the full 0266-0000-0010VL is given in SEQ ID NO: 8 and the CDRs according to the Kabat CDR definitions are given in SEQ ID NO: 12, SEQ ID NO: 13 and SEQ ID NO: 14, respectively.

All numbering used in this example refers to the Kabat numbering scheme.

TABLE 3

Sequence listing for 0266-0000-0010

| 0266-0000-0010VH | SEQ ID NO: 7 | DVKLVESGGGLVKPGGSLKLSCVASGFTFS SYTMSWVRQTPEKRLEWVATISGGGSHIYY ADSVKGRFTISRDNAKNTLYLQMSSLKSED TAIYYCTRDGRDGSWFAYWGQGTLVTVSA (CDRs marked with bold) |

TABLE 3-continued

Sequence listing for 0266-0000-0010

| 0266-0000-0010VL | SEQ ID NO: 8 | DIVMTQSPATLSVTPGDRVSLSCRTSQSIGDYLHWYQQKSHESPRLLIKYVSQSISGIPSRFSGSGSGSDFTLSINSVESEDVGVYYCQNSHSFPLTFGSGTKLELK<br>(CDRs marked with bold) |
|---|---|---|
| CDR_H1 | SEQ ID NO: 9 | SYTMS |
| CDR_H2 | SEQ ID NO: 10 | TISGGGSHIYYADSVKG |
| CDR_H3 | SEQ ID NO: 11 | DGRDGSWFAY |
| CDR_L1 | SEQ ID NO: 12 | RTSQSIGDYLH |
| CDR_L2 | SEQ ID NO: 13 | YVSQSIS |
| CDR_L3 | SEQ ID NO: 14 | QNSHSFPLT |

A 3D model of 0266-0000-0010 was build using standard techniques in MOE (available from www.chemcomp.com) and all residues within 4.5 Å of the effective CDR regions (VH: 31-35B, 50-58, 95-102; VL: 24-34, 50-56, 89-97) are defined as Mask residues. Mask residues are all potentially important for sustaining the binding in the CDRs.

The mask residues for 0266-0000-0010 include positions 1-4, 22, 27-37, 47-60, 69-71, 73, 78, 91-104 for the heavy chain and 1-5, 6, 22-36, 46-58, 62, 64-71, 87-98 for the light chain.

Using germline searches and manual inspection VH3_21 and JH4 were identified as an appropriate human germline combination for the heavy chain and the corresponding sequence is listed in Table 4, SEQ ID NO: 15 and V6D_41 and JK4 were identified as the appropriate human germline combination for the light chain and the corresponding sequence is listed in Table 4, SEQ ID NO: 16, but other germlines might also be used.

TABLE 4

| Sequences of variable human germline combinations for heavy and light chain | | |
|---|---|---|
| VH3_21/JH4 | SEQ ID NO: 15 | EVQLVESGGGLVKPGGSLRLSCAASGFTFSSYSMNWVRQAPGKGLEWVSSISSSSYIYYADSVKGRFTISRDNAKNSLYLQMNSLRAEDTAVYYCAR/YFDYWGQGTLVTVSS |
| V6D_41/JK4 | SEQ ID NO: 16 | DVVMTQSPAFLSVTPGEKVTITCQASEGIGNYLYWYQQKPDQAPKLLIKYASQSISGVPSRFSGSGSGTDFTFTISSLEAEDAATYYCQQGNKHP/LTFGGGTKVEIK |

The humanisation can now be performed with the following rules:

Residues outside the mask are taken as human.

Residues inside the mask and inside the Kabat CDR are taken as murine.

Residues inside the mask and outside the Kabat CDR with mouse/germline consensus are taken as the consensus sequence.

Residues inside the mask and outside the Kabat CDR with mouse/germline difference are taken as human, and these residues are subject to potential back mutations.

Grafting the effective CDR regions of 0266-0000-0010 into the germlines forms the basic humanization construct of 0266-0000-0010, hz0266-0000-0010 and the variable parts of it is listed in Table 5, The heavy chain is given in SEQ ID NO: 17 and the light chain is given in SEQ ID NO: 18

TABLE 5

| Sequences of variable heavy and light chain of a humanized 0266-0000-0010 | | |
|---|---|---|
| hz0266-0000-0010VH | SEQ ID NO: 17 | EVQLVESGGGLVKPGGSLRLSCAASGFTFSSYTMSVVRQAPGKGLEVVVSTISGGGSHIYYADSVKGRFTISRDNAKNSLYLQMNSLRAEDTAVYYCARDGRDGSWFAYWGQGTLVTVSS |
| hz0266-0000-0010VL | SEQ ID NO: 18 | DWMTQSPAFLSVTPGEKVTITCRTSQSIGDYLHVVYQQKPDQSPKLLIKYVSQSISGVPSRFSGSGSGTDFTFTISSLEAEDAATYYCQNSHSFPLTFGGGTKVEIK |

From an analysis of the hz0266-0000-0010 sequences, the CDRs according to Kabats definition are as shown in Table 6 and are identical to the corresponding murine mAb 0266-0000-0010.

TABLE 6

| CDR sequences for hz0266-0000-0010 | | |
|---|---|---|
| CDR_H1 | SEQ ID NO: 9 | SYTMS |
| CDR_H2 | SEQ ID NO: 10 | TISGGGSHIYYADSVKG |
| CDR_H3 | SEQ ID NO: 11 | DGRDGSWFAY |
| CDR_L1 | SEQ ID NO: 12 | RTSQSIGDYLH |
| CDR_L2 | SEQ ID NO: 13 | YVSQSIS |
| CDR_L3 | SEQ ID NO: 14 | QNSHSFPLT |

Any discrepancy between 0266-0000-0010 and hz0266-0000-0010 in a mask residue will create a potential back-mutation and the list of potential back mutations is shown in Table 7.

TABLE 7

| Potential back-mutations | |
|---|---|
| hz0266-0000-0010VH | E1D, Q3K, S49A, A93T |
| hz0266-0000-0010VL | V2I, T22S, V58I, T69S |

Further the lead contains at least 1 potential deamidation site NS in position 90-91 of the light chain and 2 potential isoasp sites in 95-96 and 98-99 of the heavy chain. In order to evaluate candidates without these potential sites the mutants shown in Table 8 will be prepared.

TABLE 8

| Potential mutants of hz0266-0000-0010 | |
|---|---|
| hz0266-0000-0010VH | D95X1, G96X2, D98X1, G99X2 (X1 is any amino acid, but D) (X2 is any amino acid, but G) |

TABLE 8-continued

Potential mutants of hz0266-0000-0010

| hz0266-0000-0010VL | N90X3, S91X4 |
|---|---|
| | (X3 is any amino acid, but N) |
| | (X4 is any amino acid, but S) |

In order to investigate all potentially humanised mAbs all combinations of the above mutants listed in Table 7 and 8 have to be produced and based on affinity screening, expression analysis and stability studies the final humanised candidate will be selected.

Example 14: Characterisation of Commercially Available Monoclonal Antibodies

Several prior-art anti-human-uPA monoclonal antibodies have been reported and are offered commercially. All of the antibodies that were available to us were tested in the assays used to select our anti-uPA dual-acting monoclonal antibodies (see Examples 5, 7 and 8) reported in this application. The results listed in Table 9 show that four of the 18 tested antibodies were able to inhibit human uPA activity both in the coupled zymogen activation assay (see Example 5) and in the catalytic assay (see Example 7), but not in the sc-uPA activation assay (see Example 8). One antibody was able to inhibit uPA activity in both the coupled zymogen activation assay (see Example 5) and the sc-uPA activation assay (Example 8). The other nine antibodies did not significantly inhibit uPA in any of the assays. Importantly, none of the prior art antibodies were able to inhibit the uPA activity in all three assays (see assays in Examples 5, 7 and 8).

TABLE 9

$IC_{50}$ values [nM] for Novo Nordisk and prior art monoclonal antibodies in the assays described in the listed examples.

| Clone name | Supplier | Ex. 5 | Ex. 7 | Ex. 8 |
|---|---|---|---|---|
| Novo Nordisk antibodies | | | | |
| 0266-0000-0009 | | <0.7 | 6.7 | 13 |
| 0266-0000-0010 | | <0.7 | 113 | 5 |
| 0266-0000-0015 | | <0.7 | 100 | 3 |
| 0266-0000-0016 | | | 4 | 2 |
| 0266-0000-0019 | | >200 | 133 | — |
| Prior-art antibodies | | | | |
| EPR6273 | Abcam | — | — | — |
| H77A10 | Abcam | — | — | — |
| U3.3.12 | Cedarlane | 2.6 | — | — |
| MAFB4476 | Creative BioMart | — | — | — |
| 724-3A1-8 | Novus Biologicals | — | — | — |
| 724-3G6-5 | Novus Biologicals | — | — | — |
| MM0596-8G26 | Novus Biologicals | <0.7 | 22 | — |
| Clone 204212 | R&D Systems | <0.7 | <0.7 | — |
| PUK1 | Technoclone | 24 | — | 46 |
| 14scu-PA | Technoclone | >67 | — | — |
| 1scu-PA | Technoclone | — | — | — |
| 35scu-PA | Technoclone | — | — | — |
| MPW4UK | Technoclone | — | — | — |
| Clone 16 (U-16)* | Thermo Scientific | <0.7 | <0.7 | — |
| '7-18' | Thermo Scientific | — | — | — |
| Clone 12 (U-12)* | Thermo Scientific | — | — | — |
| Clone 6 (U-6)* | Thermo Scientific | 2.3 | — | — |
| 5F79 | US Biological | >67 | >67 | — |

(—) indicates a non-inhibiting antibody.

Example 15: Antibodies Functionally Inhibiting Endogenous uPA in Human Neutrophil Granulocytes (PMNs)

To assess whether the selected dual-acting anti-uPA monoclonal antibodies are able to functionally inhibit endogenous uPA in human neutrophils we used the assay described in Example 9.

PMNs were obtained from blood provided by the voluntary donor corps of Novo Nordisk A/S in Måløv. The procedure has been approved by the Scientific Ethical Committees of Region Copenhagen (Journal number H-D-2007-0055). Freshly drawn blood was collected into vials containing EDTA. The blood cells were separated by centrifugation blood (4 parts) through a Ficoll-Paque PLUS (GE Health Care) gradient (3 parts) for 30 min (400×g) at room temperature. The granulocyt-containing layer was suspended in PBS containing dextran-500 (Sigma) for 1 h to remove contaminating erythrocytes. The supernatant was centrifuged for 5 min (250×g) at room temperature and remaining erythrocytes was osmotically lysed using 0.2% NaCl for 55 s. The solution is made isotonic by 1.2% NaCl+PBS and centrifuged at 250×g for 5 min, before the osmotic lyses was repeated. After centrifugation the PMNs was resuspended in Reaction Mixture (RM): HBSS: (cat no 14175 Gibco) 137 mM NaCl, 5.3 mM KCl, 0.33 mM $Na_2HPO_4$, 4 mM $NaHCO_3$, 0.44 mM $KH_2PO_4$, 5 mM glucose supplemented with 0.4 mM $MgSO_4*7H_2O$, 0.5 mM $MgCl_2$, 0.5 mM $CaCl_2$, 20 mM HEPES. Cell density was determined by NucleoCounter (Chemometec). Test compounds were dissolved in RM. The suspension contained >95% PMNs.

Recombinant human GM-CSF at 10 nM was added to the PMNs suspension since we previously showed this to increase uPA activity. The wells were coated with human fibrinogen (cat no F3879-1G, Sigma). Each well contained 0.35-0.5 $10^6$ PMNs, human plasminogen, 0.5 µM (American diagnostic), the chromogenic plasmin substrate H-D-Val-Leu-Lys-p-nitroanilide S-2251 (Chromogenix) at 0.5 mM and anti-uPA test antibody. Absorbance at 405 and 650 nm was measured every 5 min for 3 hrs at 37° C. on a SpectraMaxPlus (Molecular Devices). The curve derived from the absorbance (405-650 nm) is a measure of plasmin activity. The curve was differentiated and the maximal slope used as maximal uPA activity.

The results showed that the dual-acting antibodies 0266-0000-0010 inhibited uPA with an $IC_{50}$ of 14 nM and 0266-0000-0015 with an $IC_{50}$ 0.9 nM. The single-acting 0266-0000-0016 and 0266-0000-0019 exhibited a lower potency with an $IC_{50}$, of 25 and ~200 nM respectively.

Example 16: Humanization of Anti-Human uPA Antibody

The humanized forms of antibodies have variable framework region(s) substantially from a human immunoglobulin (termed an acceptor immunoglobulin) and CDRs substantially from a murine antibody, in this case, the mAb 0266-0000-0010 (SEQ ID NO: 7 and 8). Back mutations which might be critical for maintaining the binding affinity and specificity were predicted by 3D model analysis. The humanized form of antibody 0266-0000-0010, the mAb 0266-0000-0043 was produced and evaluated by SPR and a uPA functional assay using a coupled zymogen activation assay with a chromogenic substrate.

Experimental data demonstrated that mAb 0266-0000-0043 and a recombinantly produced version of mAb 0266-

0000-0010 (rec0266-0000-0010) had similar binding profile to human and cynomolgus sc-uPA; and comparable inhibitory effect on plasminogen activation by human or cynomolgus uPA. The protein sequences of mAbs 0266-0000-0043 and rec0266-0000-0010 are shown in table 10. For cloning purposes the sequence in the VL to CL transition of SEQ ID NO 20, carries a RTVAA sequence motif, i.e. two residues "TV" derived from the human kappa sequence, in lieu of the fully murine RADAA kappa sequence.

Generation of Expression Vectors for mAb

The coding sequences for light chain or heavy chain were inserted into pJSV002, a CMV promoter-based expression vectors, between EcoRI and BamHI sites. A signal peptide from CD33 (mpllllllpllwagala) was added before coding sequences to facilitate secretion.

TABLE 10

The amino acid sequences of mAbs 0266-0000-0043 and rec0266-0000-0010

| Clone | Heavy chain sequence | Light chain sequence |
|---|---|---|
| rec0266-0000-0010 | Dvklvesggglvkpggslklscva sgftfssytmswvrqtpekrlewv atisgggshiyyadsvkgrftisr dnakntlylqmsslksedtaiyyc trdgrdgswfaywgqgtivtvsaa kttppsyyplapgsaaqtnsmvtl gclvkgyfpepvtvtwnsgslssg vhtfpavlgsdlytlsssvtvpss twpsetvtcnvahpasstkvdkki vprdcgckpcictvpevssvfifp pkpkdvltitltpkvtcvvvdisk ddpevqfswfvddvevhtaqtqpr eeqfnstfrsyselpimhqdwlng kefkcrynsaafpapiektisktk grpkapqvytipppkegmakdkvs ltcmitdffpeditvewqwngqpa enyknthqpimdtdgsyfvyskInv qksnweagntftcsvlheglhnhh tekslshspgk (SEQ ID NO: 19) | Divmtgspatlsvt-pgd rvslscrtsqsigdylh wyqqkshespr1-likyv sqsisgipsrf-sgsgsg sdftlsinsvesed-vgv yycqnshsfpltf-gsgt klelkrtvaapt-vsifp psseqltsggasv-vcfl nnfypkdinvkwk-idgs erqngvlnswtdqd-skd stysmsstltltkd-eye rhnsytceathk-tstsp ivksfnrnec (SEQ ID NO: 20) |
| rec0266-0000-0043 | Dvklvesggglvkpggslrlscaa sgftfssytmswvrqapgkglewv atisgggshiyyadsvkgrftisr dnaknslylqmnslraedtavyyc trdgrdgswfaywgqgtlvtvssa stkgpsvfplapcsrstsestaal gclvkdyfpepvtvswnsgaltsg vhtfpavlgssglyslssvvtvps sslgtktytcnvdhkpsntkvdkr veskygppcppcpapeflggpsvf lfppkpkdtlmisrtpevtcvvvd vsgedpevqfnwyvdgvevhnakt kpreeqfnstyrvvsvltvlhqdw lngkeykckvsnkglpssiektis kakgqprepqvytlppsgeemtkn qvsltclvkgfypsdiavewesng qpennykttppvldsdgsfflysr ltvdksrwqegnvfscsvmhealh nhytqkslslslgk (SEQ ID NO: 21) | Divmtgspaflsvt-pge kvtiscrtsqsigdylh wyqqkpdgspkl-likyv sqsisgipsrf-sgsgsg sdftftissleae-daatyycqnshsf-pltfggggt kveikrtvaaps-vfifp psdeqlksgtasv-vcll nnfypreakvqwk-vdna lqsgnsqesvtegd-skd styslsstltl-skadye khkvy-acevthqglssp vtksfnrgec (SEQ ID NO: 22) |

TABLE 11

The DNA sequences of mAbs 0266-0000-0043 and rec0266-0000-0010

| Clone | Heavy chain sequence | Light chain sequence |
|---|---|---|
| rec0266-0000-0010 | | gacgtcaagctggtggaaagcggagGacatcgtgatgac-cca gaggcctggtcaaacccggaggcaggagccctgcta-cactga cctgaagctgagctgcgtggccagcgcgtgacccccgga-gac ggcttcaccttcagcagctacacaaagggtgagcct-gagctg tgagctgggtgaggcagacacccgacaggacctccca-gagca gaagaggctggagtgggtggctacctcggcgactacctg-cac attagcggaggcggcagccacatcttggtaccagca-gaagag actacgccgacagcgtgaagggcagccacgagagcccca-ggc gttcaccatcagcagggacaacgcctgctgatcaag-tacgtg aagaacaccctgtacctgcagatgaagccagagcatca-gcgg cagcctgaagagcgaggacaccgccattcccagcaggt-tca catctactactgcaccagggacggcggcagcg-gaagcgga agagacggcagctggttcgcctactagcgacttcac-cctcag ggggacagggaaccctggtgaccgtcatcaacagcgtg-gaaa gagcgccgccaaaacgacaccccagcgag-gactgggcgtg tctgtctatccgctagcccctggattactactgcca-gaacag ctgctgcccaaactaactccatggtccacagcttc-ccctca gaccctgggatgcctggtcaagggccttcggcagcg-gcacc tatttccctgagccactgacagtgaaagctggagct-gaagag cctggaactctggatccctgtccaggaccgtggcggcgc-caa cggtgtgcacaccttcccagctgtcctgtatccatcttc-cca ctgcagtctgacctctacactctgaccatccagtgagca-gtt gcagctcagtgactgtcccctccagaacatctggaggt-gcct cacctggcccagcgagaccgtcaccagtcgtgtgct-tcttg tgcaacgttgcccaccggccagcaaacaacttctac-cccaa gcaccaaggtggacaagaaaattgtagacatcaatgt-caagt gcccaggagttgtggttgtaagcctggaagattgatg-gcaat tgcatatgtacagtcccagaagtatgaacgacaaaatg-gcgt catctgtcttcatcttcccccccaaacctgaacagttg-gactg gcccaaggatgtgctcaccattactatcaggacag-caaagac ctgactcctaaggtcacgtgtgttgagcacctcagcat-gag tggtagacatcagcaaggatgatcccagcaccctcacgt-tga cgaggtccagttcagctggtttgtaccaaggacgagtat-gaa gatgatgtggaggtgcacacagctccgacataacagc-tatac agacgcaacccgggaggagcagttctgtgaggccact-caca caacagcactttccgctcagtcagtagacatcaact-tcaccc |

TABLE 11-continued

The DNA sequences of mAbs 0266-0000-0043 and rec0266-0000-0010

| Clone | Heavy chain sequence | Light chain sequence |
|---|---|---|
| | | gaacttcccatcatgcaccaggactattgtcaagagct-tcaa |
| | | ggctcaatggcaaggagttcaaatgcaggaatgagtgttag |
| | | cagggtcaacagtgcagctttccct(SEQ ID NO: 24) |
| | | gcccccatcgagaaaaccatctcca |
| | | aaaccaaaggcagaccgaaggctcc |
| | | acaggtgtacaccattccacctccc |
| | | aaggagcagatggccaaggataaag |
| | | tcagtctgacctgcatgataacaga |
| | | cttcttccctgaagacattactgtg |
| | | gagtggcagtggaatgggcagccag |
| | | cggagaactacaagaacactcagcc |
| | | catcatggacacagatggctcttac |
| | | ttcgtctacagcaagctcaatgtgc |
| | | agaagagcaactgggaggcaggaaa |
| | | tactttcacctgctctgtgttacat |
| | | gagggcctgcacaaccaccatactg |
| | | agaagagcctctcccactctcctgg |
| | | taaatga |
| | | (SEQ ID NO: 23) |
| rec0266-0000-0043 | gacgtgaagctggtggaaagcggagGacatcgtgatgac-cca | ccccccaaaacccaaggacactctcagcaggacag-caaggac |
| | gcggcctcgtgaaacctggcggaaggagcccgccttc-ctga | atgatctcccggacccctgaggtcaagcacctacagc-ctcag |
| | cctgagactgagctgcgctgccagcgtgacctgga-gag | cgtgcgtggtggtggacgtgagccacagcaccct-gacgctga |
| | ggcttcaccttcagcagctacaccaaaggtgaccatca-gctg | ggaagaccccgaggtccagttcaacgcaaagcagactac-gag |
| | tgagctgggtgaggcaggctcccggcaggaccagcca-gagca | tggtacgtggatggcgtggaggtgcaaacacaaagtc-tacgc |
| | caaaggactggagtgggtggccacatcggcgactacctg-cac | ataatgccaagacaaagccgcgggactgcgaagtcac-ccatc |
| | attagcggaggcggctcccacatcttggtaccagca-gaagcc | ggagcagttcaacagcacgtaccgtagggcct-gagctcgccc |
| | actacgccgacagcgtcaagggcagcgaccagagc-cccaagc | gtggtcagcgtcctcaccgtcctgcgtcacaaagagct-tcaa |
| | gttcaccatcagcagggacaacgcctgctgatcaag-tacgtg | accaggactggctgaacggcaaggacaggggagagtgttag |
| | aagaacagcctgtacctgcagatgaagccagtccatca-gcgg | gtacaagtgcaaggtctccaacaaa(SEQ ID NO: 26) |
| | acagcctgagggccgaggacaccgccatccccttcca-gattta | ggcctcccgtcctccatcgagaaaa |
| | cgtgtactactgcaccagggacggcgcggcagcggca-gcgga | ccatctccaaagccaaagggcagcc |
| | agggacggaagctggttcgcctactagcgacttcacct-tcac | ccgagagccacaggtgtacaccctg |
| | ggggacagggcaccctcgtgaccgtcatcagcagcctg-gaag | cccccatcccaggaggagatgacca |
| | gagcagcgctagcaccaagggcccaccgaagacgccgc-cacc | agaaccaggtcagcctgacctgcct |
| | tccgtcttcccctggcgccctgcttactactgcca-gaactc | ggtcaaaggcttctaccccagcgac |
| | ccaggagcacctccgagagcacagcccacagcttc-ccctga | atcgccgtggagtgggagagcaatg |
| | cgccctgggctgcctggtcaaggaccattcggcggcg-gcacc | ggcagccggagaacaactacaagac |
| | tacttccccgaaccggtgacggtgtaaggtggagat-caagag | cacgcctcccgtgctggactccgac |
| | cgtggaactcaggcgccctgaccaggactgtggcggcgc-cat | ggctccttcttcctctacagcaggc |
| | cggcgtgcacaccttcccggctgtcctgtcttcatcttc-ccg | taaccgtggacaagagcaggtggca |
| | ctacagtcctcaggactctactcccccatctgatgagca-gtt | ggaggggaatgtcttctcatgctcc |
| | tcagcagcgtggtgaccgtgccctcgaaatctggtac-cgcta | gtgatgcatgaggctctgcacaacc |
| | cagcagcttgggcacgaagacctacgcgttgtgtgcct-gctg | actacacacagaagagcctctccct |
| | acctgcaacgtacatcacaagcccaaataacttctatc-ccag | gtctctgggtaaatga |
| | gcaacaccaaggtggacaagagagtagaggccaaagta-cagt | (SEQ ID NO: 25) |
| | tgagtccaaatatggtccccatgcggaaggtgga-taacgcc | |
| | ccaccatgcccagcacctgagttccctcaatcggg-taactc | |
| | tgggggaccatcagtcttcctgttccaggagagtgt-cacag | |

Recombinant mAb Expression

Plasmid DNA encoding the respective light chain and heavy chain were co-transfected into Freestyle™ 293-F cells (Life Technologies, Cat. # R79007) with amount ratio of 1:1, by using 293Fectin™ reagent (Invitrogen, cat. #12347). Transfected cells were grown in serum-free FreeStyle 293 medium (Gibco, cat. #12338) containing 4 mM glutamine (Life Technologies, Cat. #25030-024), 1% PLURONIC® F68 (Gibco, Cat. #24040-032) and penicillin-streptomycin antibiotics (Life Technologies, Cat. #10378016) at $1 \times 10^6$ cells per ml and incubated with shaking for 5 days at 37° C., 8% $CO_2$. Supernatants were collected on day 5 post transfection and clarified by centrifugation.

DNA Transfection:

The cell density of cultures used for transfection was $0.9\text{-}2.0 \times 10^6$ cells/ml.

A mix of 0.5 µg light chain (LC) vector DNA and 0.5 µg heavy chain (HC) vector DNA was used per ml cell culture.

The DNA was diluted in Opti-MEM media (Gibco) to 30 µl media/µg DNA, mixed and incubated at room temperature (23-25° C.) for 5 min.

293Fectin™ (Invitrogen) was used as transfection reagent at a concentration of 1 µl per µg DNA.

The 293Fectin™ was diluted 30× in Opti-MEM media (Gibco), mixed and incubated at room temperature (23-25° C.) for 5 min.

The DNA and 293Fectin solutions were mixed and left to incubate at room temperature (23-25° C.) for 25 min.

The DNA-293Fectin mix was then added directly to the cell culture.

The transfected cell culture was transferred to a shaker incubator at 37° C., 8% $CO_2$ and 125 rpm.

5 days post transfection, cell culture supernatants were harvested by centrifugation, followed by filtration through a 0.22 μm PES filter (Corning).

Quantitative analysis of antibody production was performed by Biolayer Interferometry directly on clarified cell culture supernatants using the FortéBio Octet system and protein A biosensors.

Purification

Figure 3:
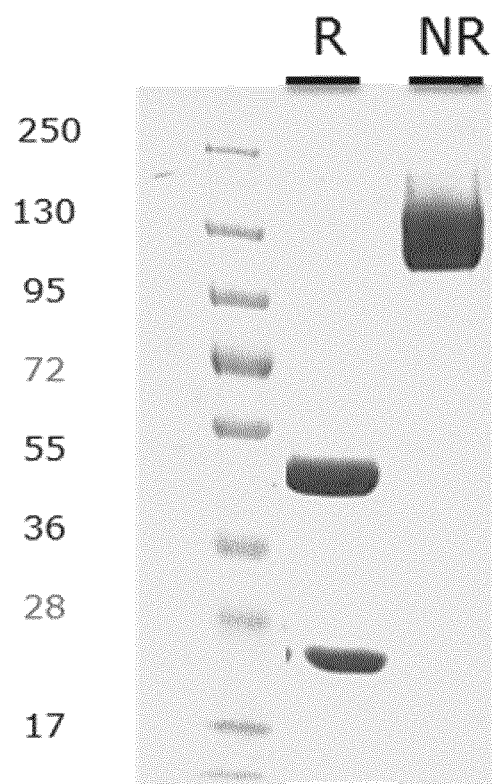
FIG. 3: SDS-PAGE gel of mAb 0266-0000-0043, reduced (R) and non-reduced (NR) (see Example 16).

Culture supernatant containing secreted 0266-0000-0043 was harvested by centrifugation (15,000 rpm×20 min, 4° C.) and then cleared by the filtration with 0.45 μm cellulose nitrate membrane. The cleared supernatant was applied to 5 mL MabSelectSuRe column (GE 17-5438-02), followed by a 10 column volume wash with PBS. The bound mAb was then eluted with 20 mM formic acid and 100 mM arginine pH3.5 and collected as 2 mL fractions into the glass tube with 200 ul 1M Tris-HCl pH9.0. The peak fractions were pooled and buffer-exchanged to Phosphate Buffered Saline (PBS) with Amicon ultra 15 centrifugal units (30 kD MWCO, Millipore). After concentrating, the final protein concentrations were determined by measuring 280 nm absorbance with a NANODROP UV spectrometer. Protein purity was assessed by sodium dodecyl sulphate polyacrylamide gel electrophoresis (SDS-PAGE). Endotoxin levels were evaluated by LAL test (Charles River). The SDS-PAGE gel setup is shown in Table 12, and the result gel is shown in FIG. 3.

TABLE 12

SDS-PAGE Gel Setup

| Gel ID | 8-15% Gradient Gel | Red/Oxidized |
|---|---|---|
| Lane 1 | Marker: 250, 130, 95, 72, 55, 36, 28 KD | Reduced |
| Lane 2 | 0266-0000-0043 10ug | Reduced |
| Lane 3 | 0266-0000-0043 10ug (unheated) | Oxidized |

SE-HPLC Analysis

Figure 4:
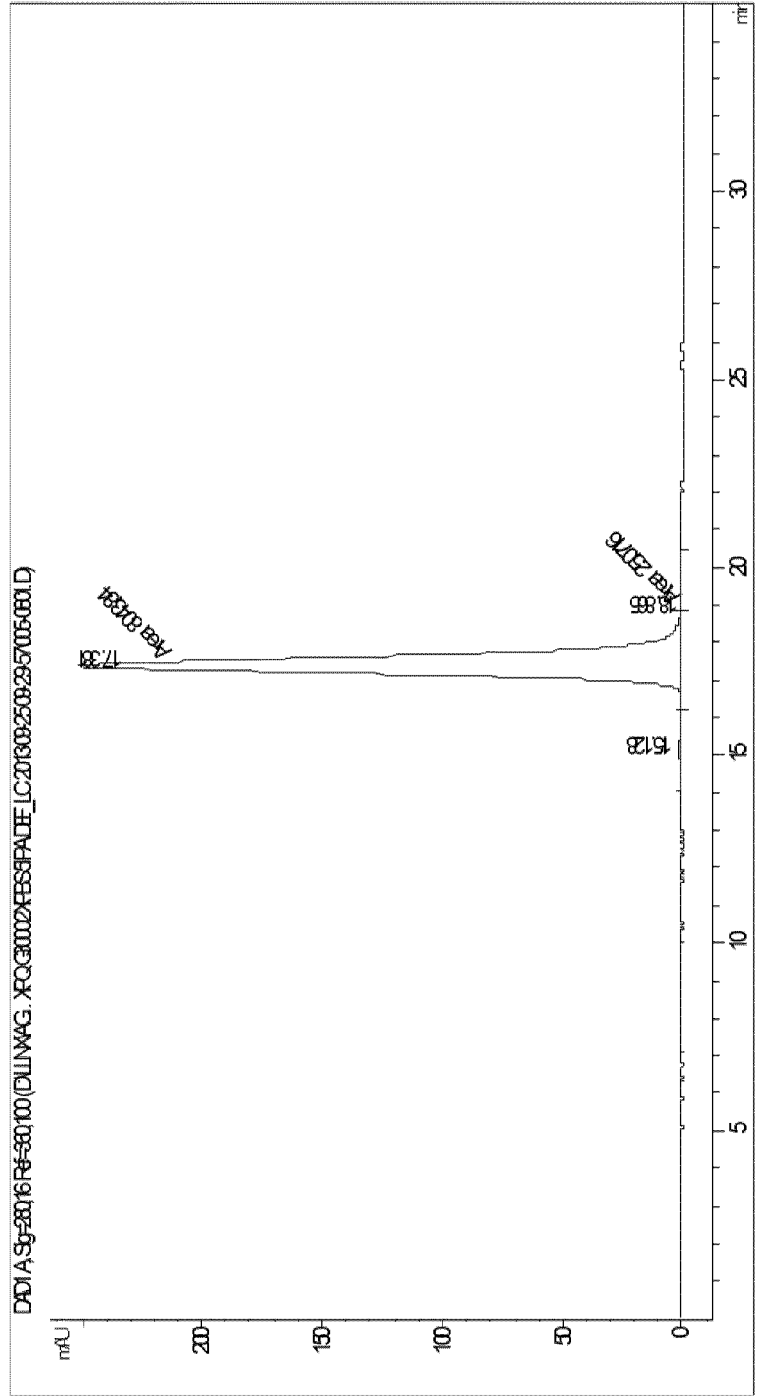
FIG. 4: SE-HPLC analysis of mAb 0266-0000-0043 (see Example 16).

Typically 50 μg protein for SE-HPLC was analysed on a TSKSWxI 3000 column (Tosoh, Part #085410, 300×7.8 mm) using a 1200 HPLC system (Agilent Technologies). The buffer was 16 mM Na2HPO4, 3 mM KH2PO4, 247 mM NaCl, 6 mM KCl, 5% isopropanol v/v pH6.8 and flow rate was 0.5 ml/min unless stated otherwise. The SE-HPLC Results Summary is shown in Table 13. below, and the results in FIG. 4.

TABLE 13

SE-HPLC Results Summary

| # | Time | Area | Height | Width | Symmetry | Area % |
|---|---|---|---|---|---|---|
| 1 | 15.13 | 80.50 | 1.50 | 0.81 | 0.88 | 0.99 |
| 2 | 17.38 | 8043.80 | 251.20 | 0.53 | 0.89 | 98.71 |
| 3 | 18.87 | 25.10 | 0.82 | 0.51 | 0.00 | 0.31 |

Measurement of Binding Kinetics by SPR

In order to compare with murine mAb, the binding profile to recombinant human sc-uPA protein (SEQ ID NO: 1) and cynomolgus sc-uPA (SEQ ID NO: 3) was measured by surface plasmon resonance (SPR).

The experiments were performed on a Biacore™ instrument (GE Healthcare) and analysed with the BIAcore 4000 Evaluation Software. Anti-human uPA rec0266-0000-0010 (SEQ ID NO: 19 and 20) and 0266-0000-0043 (SEQ ID NO: 21 and 22) were directly immobilized at 150-600 RU on flow cells of a CM5 sensor chip (GE Healthcare; cat. # BR-1000-12) via amine coupling, respectively. Recombinant human sc-uPA and cynomolgus sc-uPA proteins were diluted in HBS-N (GE Healthcare Cat BR-1006-70) with 1% BSA buffer with a dilution factor 3× ranging 1000-0.13 nM. Recombinant human sc-uPA and cynomolgus sc-uPA proteins were injected for 60 s, followed by a 600 s dissociation phase. Binding curves were measured at 25° C. with a flow rate of 30 μL/min. Regeneration of the chip surface was performed with pH1.5 Glycine for 25 s at 30 μl/min. Determination of the kinetic parameters was performed by fitting with a 1:1 binding model. Kinetic parameters were calculated and are stated in Table 14 below.

Both rec0266-0000-0010 (SEQ ID NO: 19 and 20) and 0266-0000-0043 (SEQ ID NO: 21 and 22) showed very good binding to both human and cynomolgus sc-uPA. And binding kinetics profiles are similar between rec0266-0000-0010 and 0266-0000-0043.

TABLE 14 rec0266-0000-0010 and 0266-0000-0043 binding kinetic parameters to recombinant human sc-uPA and recombinant cynomolgus sc-uPA.

| NNCD | Analyst | Ka (1/Ms) | Kd (1/s) | KD (M) |
|---|---|---|---|---|
| rec0266-0000-0010 | Human sc-uPA | 5.61E+05 | 5.30E−04 | 9.44E−10 |
| 0266-0000-0043 | | 5.06E+05 | 9.00E−04 | 1.78E−09 |
| rec0266-0000-0010 | Cynomoguls | 1.98E+06 | 1.04E−04 | 5.26E−11 |
| 0266-0000-0043 | sc-uPA | 1.46E+06 | 1.64E−04 | 1.12E−10 |

The Coupled Zymogen Activation Assay

Figure 5:
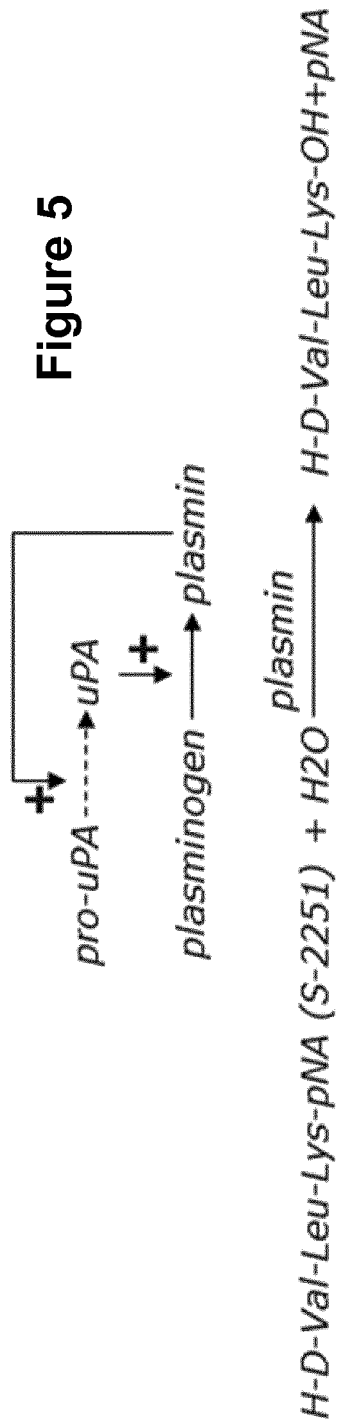
FIG. 5: Principle of the coupled zymogen activation assay (see Example 16).

In vivo, uPA converts the zymogen plasminogen to the active plasmin. In turn, a positive feedback loop exists, in which plasmin also converts sc-uPA (pro-uPA) to tc-uPA (active uPA), thus enhancing the reaction kinetics. This mechanism can be used to measure the activity of uPA by monitoring the amount of plasmin generated using the chromogenic plasmin substrate H-D-Val-Leu-Lys-pNA (S-2251, Chromogenix, cat. #0082033239). See FIG. 5.

The inhibitory effect of anti-uPA binding mAbs which can neutralize uPA mediated plasminogen activation can be measured by hydrolysis of S-2251 in presence of sc-uPA and plasminogen. sc-uPA (0.25 nM) was preincubated with various concentrations of rec0266-0000-0010 or 0266-0000-0043 (0-400 ng/ml) in HBS-B at room temperature for 30 min. The addition of 0.5 M plasminogen (Glu-Plasminogen, Haematologic Technologies, Inc, cat. # HCPG-0130) and 0.5 mM plasmin substrate H-D-Val-Leu-Lys-p-nitroanilide (S-2251) initiated the reaction at 37° C. S-2251 hydrolysis was monitored for the parabolic increase in absorbance at 405 nm.

The HBS-B buffer contained: 30 mM Hepes, 135 mM NaCl, 1 mM EDTA, 0.1% BSA, pH 7.4, filtered.

The Coupled Zymogen Activation Assay (for One Sample):
- Add HBS-B buffer 178.51 μl to Eppendorf tube.
- Human sc-uPA sample diluted ×1000 by PBS, and add 5.68 μl to Eppendorf tube.
- Anti-uPA mAb normalized to 1 mg/ml by PBS, and add 21 μl to tube.
- Mix by vortex, and incubate at R.T. for 30 min
- 5 min before incubation ending, mix 1.25 μl plasminogen and 3.57 μl S-2251 in a new Eppendorf tube by vortex.
- 4.82 μl mixture of plasminogen and S-2251 add into Eppendorf tube containing HBS-B, sc-uPA, and mAb (total vol. 210 μl).
- Mixing by vortex and centrifuge.
- Read plate at R.T., ABS@405, every 5 min (or 10 min) for 4 hours.

Figure 6:
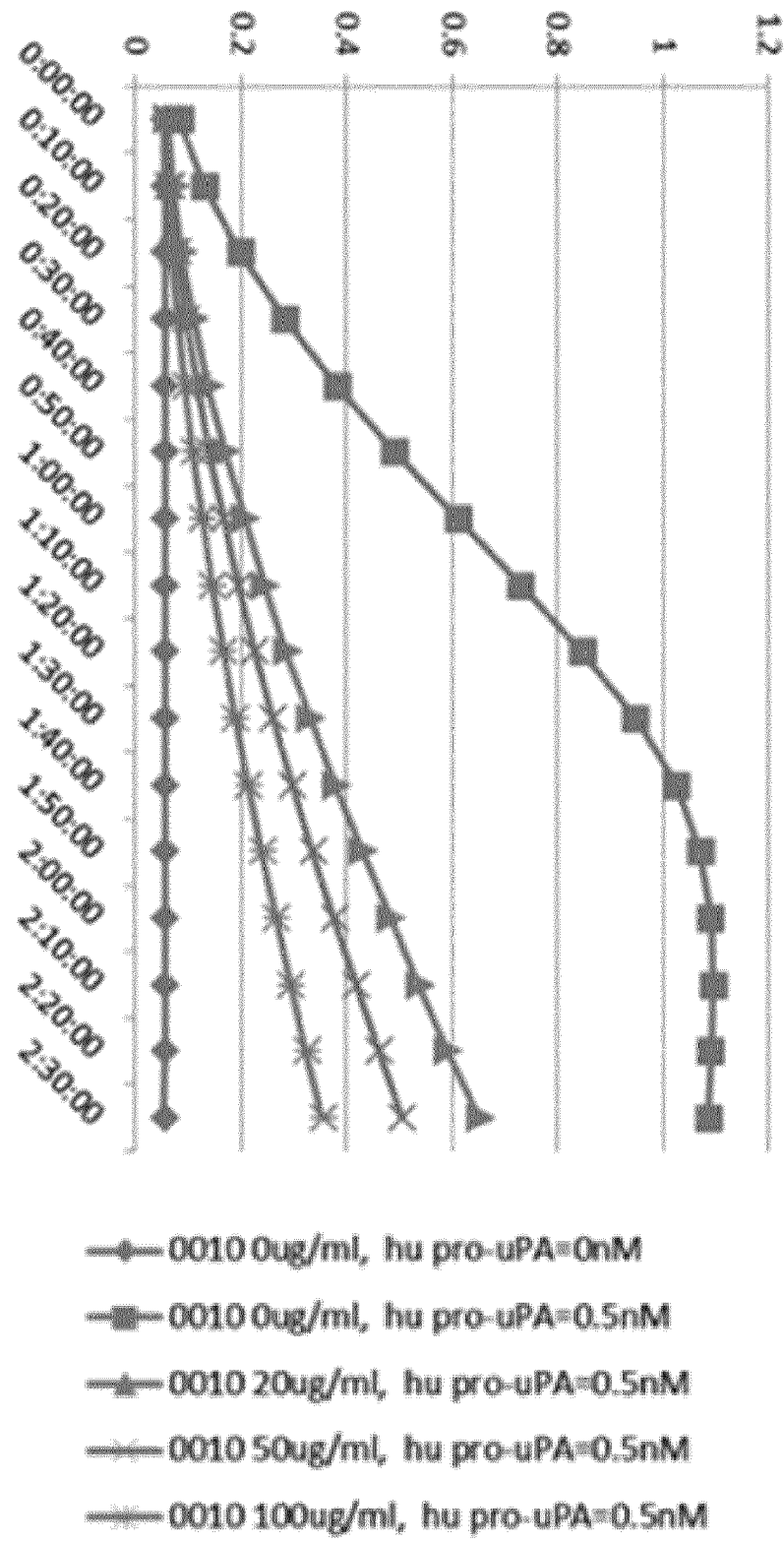
FIG. 6: Inhibition by mAb rec0266-0000-0010 of human uPA in the coupled zymogen activation assay (see Example 16).
Figure 7:
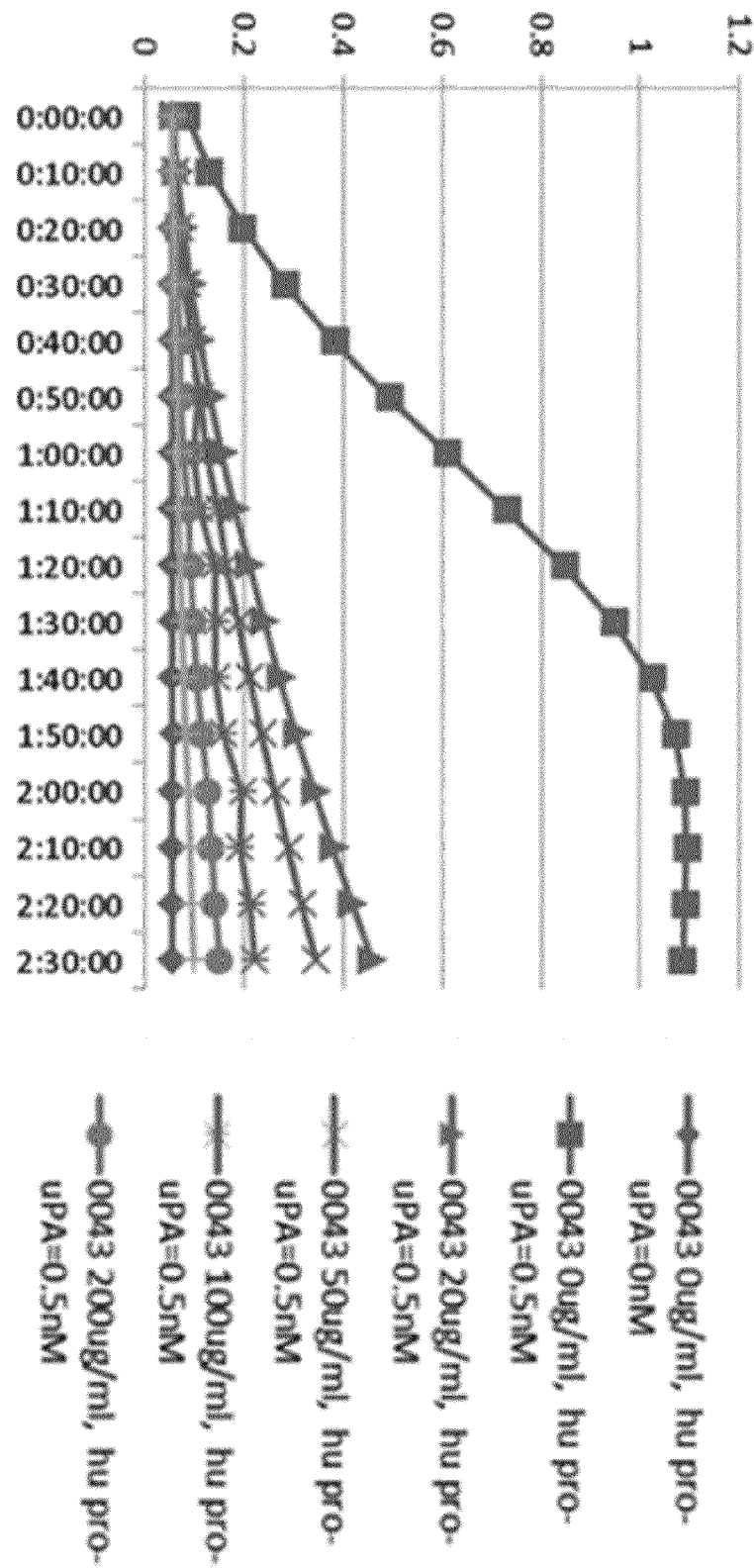
FIG. 7: Inhibition by mAb 0266-0000-0043 of human uPA in the coupled zymogen activation assay (see Example 16).
Figure 8:
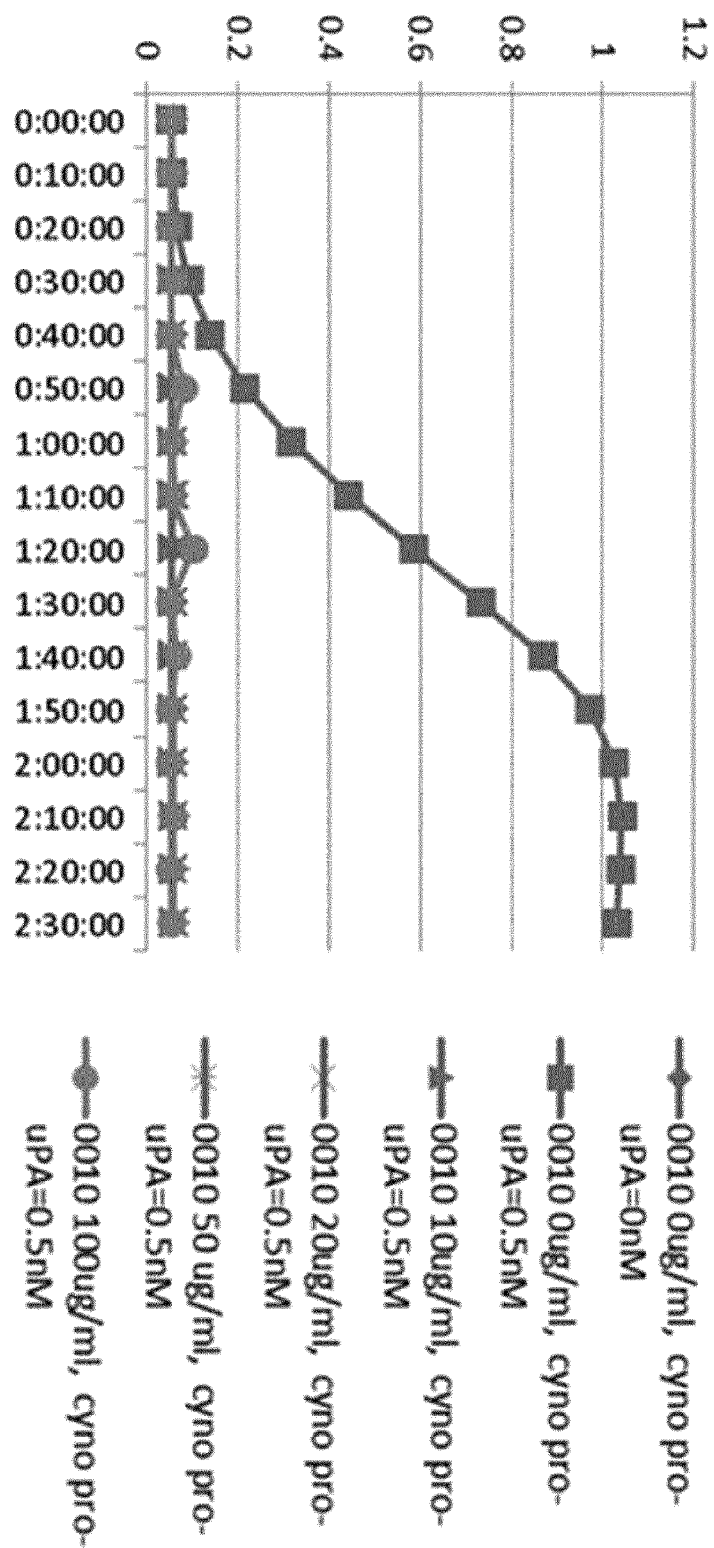
FIG. 8: Inhibition by mAb rec0266-0000-0010 of cynomolgus uPA in the coupled zymogen activation assay (see Example 16).
Figure 9:
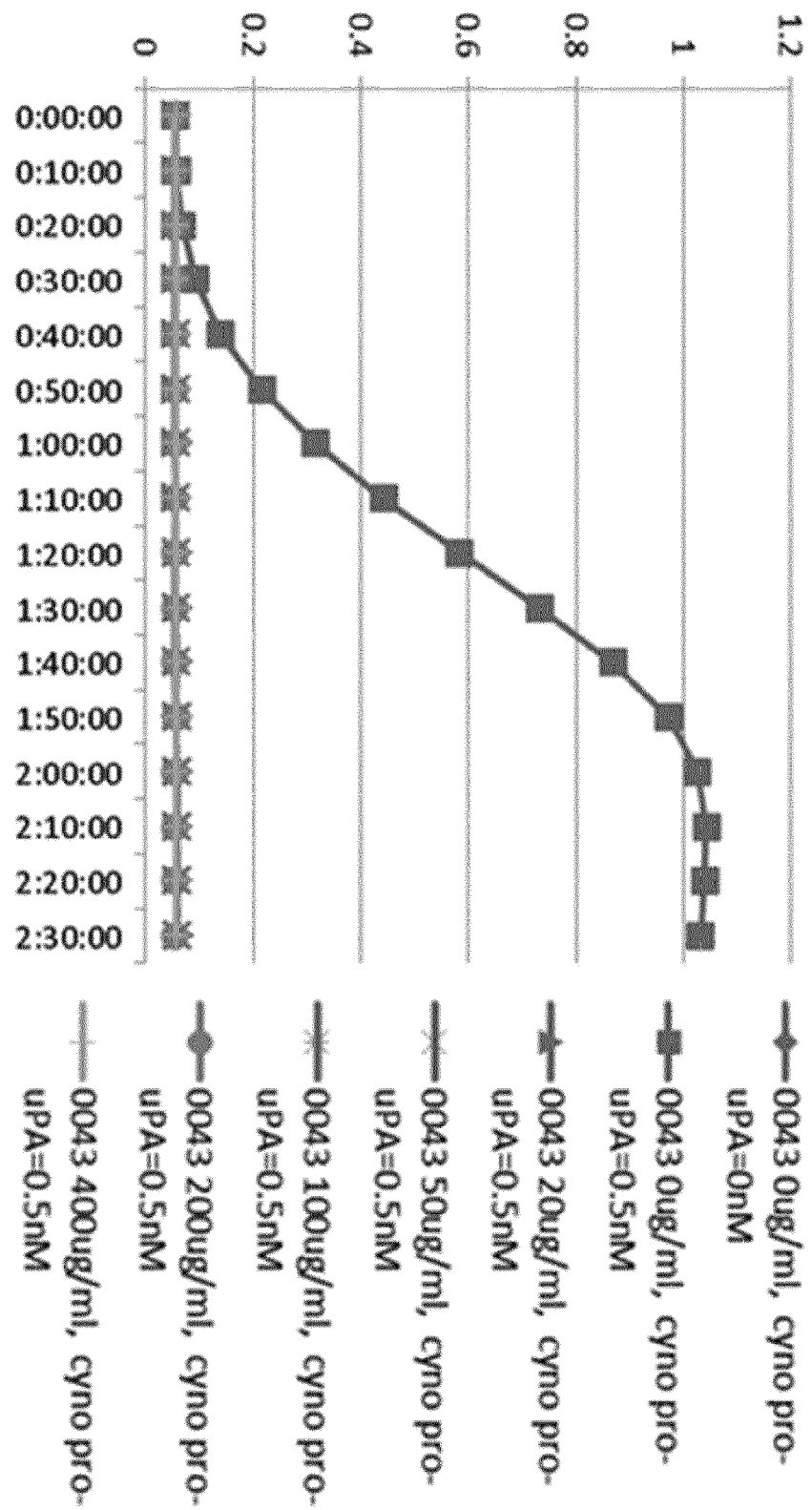
FIG. 9: Inhibition by mAb 0266-0000-0043 of cynomolgus uPA in the coupled zymogen activation assay (see Example 16).

The results of the coupled zymogen activation assay are shown in FIGS. 6-9. FIG. 6 shows mAb rec0266-0000-0010 (0010) at the concentration of 0, 20, 50, 100 μg/ml on human sc-uPA (hu pro-uPA). FIG. 7 shows mAb 0266-0000-0043 (0043) at the concentration of 0, 20, 50, 100, 200, 400 μg/ml on human sc-uPA (hu pro-uPA). FIG. 8 shows the mAb rec0266-0000-0010 (0010) at the concentration of 0, 20, 50, 100 μg/ml on cynomolgus sc-uPA (cyno pro-uPA) and FIG. 9 shows the mAb 0266-0000-0043 (0043) at the concentration of 0, 20, 50, 100, 200, 400 μg/ml on cynomolgus sc-uPA (cyno pro-uPA).

The results from both SPR and the coupled zymogen activation assays demonstrate that rec0266-0000-0010 and 0266-0000-0043 had similar binding profile to human and cynomolgus sc-uPA; and comparable inhibitory effect on plasminogen activation by human and cynomolgus uPA.

Example 17: Production of Humanized Anti-uPA mAbs Containing 1 Back Mutation or 4 Back Mutations Plasmids encoding humanized anti-uPA LC and HC (human IgG4 and human IgG1 isotypes) were used as the starting point for introducing single back mutations into the plasmids. Four candidate back mutation in VL (V21, T22S, V58I and T69S) and four in VH (E1D, Q3K, S49A, A93T) were identified and forward and reverse DNA primers introducing the specific VL or VH point mutations were purchased from Eurofins Genomics, Germany. Site-directed mutagenesis was performed using QuikChange Lightning Site-Directed Mutagenesis Kit from Agilent, the LC or HC expression plasmids as template, the mutation-specific forward and reverses primer pair and using the instructions provided by the manufacturer. The resulting expression plasmids encoded four different humanized anti-uPA LC with one back mutation and 8 different humanized anti-uPA HC with one back mutation (4 different back mutations introduced into IgG4 and into IgG1). The 16 different humanized anti-uPA mAb variants containing one single back mutation together with two anti-uPA mAb variants having either all four back mutations in VL or all four back mutations in VH (human IgG4 isotype) were expressed by transient co-transfection of HEK293 suspension cells using a total of 1 mg DNA (0.5 mg LC and 0.5 mg HC) and 1 mL 293fectin (Invitrogen, catalogue number: 12347-019) pr 1 L HEk293 transfection. Cells were typically cultured for 5-7 days post-transfection and the resulting cell culture supernatants were harvest and purified according protein-A based methods. The 18 humanized anti-uPA mAb variants (16 variants with one back mutation and two with four back mutations) were all tested in the coupled zymogen activation assay, which is described in Example 5 and Example 16. The mAb 0266-0000-0043 is an example of a humanized antibody with a number of the suggested back mutations. The mAb 0266-0000-0043 effectively inhibits human uPA in the coupled zymogen activation assay as demonstrated in Example 16.

Example 18: Removal of Anti-Human uPA Potential Iso-Asp Site on Heavy Chain

To test the possibility for removal of the potential 2 iso-asp sites "D95G96" and "D98G99" in the heavy chain of rec0266-0000-0010 (marked with bold fonts), the single-mutation variants were produced and their binding affinities to human sc-uPA were measured by Biacore.

TABLE 15

Potential iso-asp sites on rec0266-0000-0010 heavy chain (SEQ ID NO: 19):

SEQ ID NO: 19 with potential iso-asp sites marked with bold fonts dvklyesggglykpggslklscvasgftfssytmswyrqtpekrlewva
tisgggshiyyadsvkgrftisrdnakntlylqmsslksedtaiyyctr
dgrdgswfaywgqgtlytysaakttppsyyplapgsaaqtnsmytlgcl
vkgyfpepytytwnsgslssgyhtfpaylqsdlytlsssytypsstwps
etytcnvahpasstkvdkkivprdcgckpcictypevssvfifppkpkd
vltitltpkytcyvvdiskddpevqfswfvddveyhtaqtqpreeqfns
tfrsyselpimhqdwlngkefkcrynsaafpapiektisktkgrpkapq
vytipppkeqmakdkvsltcmitdffpeditvewqwngqpaenykntqp
imdtdgsyfyysklnvqksnweagniftcsylheglhnhhtekslshsp
gk Generation of Single Mutation Variants The mutation was introduced by site-directed mutagenesis with QuikChange II XL Site-Directed Mutagenesis Kit (Agilent Technologies, Cat. #200521), the codon exchange for each mutation is listed as below in Table 16.

TABLE 16

| Mutation codon exchange | | |
|---|---|---|
| Mutation | From | To |
| D95A | GAC | GCC |
| D95R | GAC | AGA |
| D95E | GAC | GAA |
| D95G | GAC | GGC |
| D95H | GAC | CAT |
| D95I | GAC | ATC |
| D95L | GAC | CTG |
| D95K | GAC | AAA |
| D95F | GAC | TTT |
| D95P | GAC | CCC |
| D95S | GAC | AGC |
| D95T | GAC | ACC |
| D95Y | GAC | TAT |
| D95V | GAC | GTG |
| G96A | GGC | GCC |
| G96R | GGC | AGA |
| G96N | GGC | AAC |
| G96E | GGC | GAA |
| G96H | GGC | CAT |
| G96I | GGC | ATC |
| G96L | GGC | CTG |
| G96K | GGC | AAA |
| G96F | GGC | TTT |
| G96P | GGC | CCC |
| G96S | GGC | AGC |
| G96T | GGC | ACC |
| G96Y | GGC | TAT |
| G96V | GGC | GTG |
| D98A | GAC | GCC |
| D98R | GAC | AGA |
| D98E | GAC | GAA |
| D98G | GAC | GGC |
| D98H | GAC | CAT |
| D98I | GAC | ATC |
| D98L | GAC | CTG |
| D98K | GAC | AAA |
| D98F | GAC | TTT |
| D98P | GAC | CCC |
| D98S | GAC | AGC |
| D98T | GAC | ACC |
| D98Y | GAC | TAT |
| D98V | GAC | GTG |
| G99A | GGC | GCC |
| G99R | GGC | AGA |
| G99N | GGC | AAC |
| G99E | GGC | GAA |
| G99H | GGC | CAT |
| G99I | GGC | ATC |

TABLE 16-continued

Mutation codon exchange

| Mutation | From | To |
|---|---|---|
| G99L | GGC | CTG |
| G99K | GGC | AAA |
| G99F | GGC | TTT |
| G99P | GGC | CCC |
| G99S | GGC | AGC |
| G99T | GGC | ACC |
| G99Y | GGC | TAT |
| G99V | GGC | GTG |

Mutant Variants Expression and Purification

Plasmid DNA encoding heavy chain harbouring single mutation were co-transfected with that of wild-type light chain into Freestyle™ 293-F cells (Life Technologies, Cat. # R79007) with amount ratio of 1:1, by using 293Fectin™ reagent (Invitrogen, cat. #12347). Transfected cells were grown in serum-free FreeStyle 293 medium (Gibco, cat. #12338) containing 4 mM glutamine (Life Technologies, Cat. #25030-024), 1% PLURONIC® F68 (Gibco, Cat. #24040-032) and penicillin-streptomycin antibiotics (Life Technologies, Cat. #10378016) at $1 \times 10^6$ cells per ml and incubated with shaking for 5 days at 37° C., 8% $CO_2$. Supernatants were collected on day 5 post transfection and clarified by centrifugation.

DNA Transfection:

The cell density of cultures used for transfection was 0.9-2.0×10⁶ cells/ml.

A mix of 0.5 µg light chain (LC) vector DNA and 0.5 µg heavy chain (HC) vector DNA was used per ml cell culture.

The DNA was diluted in Opti-MEM media (Gibco) to 30 µl media/µg DNA, mixed and incubated at room temperature (23-25° C.) for 5 min.

293Fectin™ (Invitrogen) was used as transfection reagent at a concentration of 1 µl per µg DNA.

The 293Fectin™ was diluted 30× in Opti-MEM media (Gibco), mixed and incubated at room temperature (23-25° C.) for 5 min.

The DNA and 293Fectin solutions were mixed and left to incubate at room temperature (23-25° C.) for 25 min.

The DNA-293Fectin mix was then added directly to the cell culture.

The transfected cell culture was transferred to a shaker incubator at 37° C., 8% $CO_2$ and 125 rpm.

5 days post transfection, cell culture supernatants were harvested by centrifugation, followed by filtration through a 0.22 µm PES filter (Corning).

Quantitative analysis of antibody production was performed by Biolayer Interferometry directly on clarified cell culture supernatants using the FortéBio Octet system and protein A biosensors.

Culture supernatant was harvested by centrifugation (15,000 rpm×20 min, 4° C.) and then cleared by the filtration with 0.45 µm cellulose nitrate membrane. The cleared supernatant was applied to 50 µl PreDictor MabSelect SuRe, 96-well filter plate (GE 28-9258-25). The bound mAb was then eluted with 20 mM formic acid and 100 mM arginine pH3.5, and buffer-exchanged to Phosphate Buffered Saline (PBS) with Amicon ultra 15 centrifugal units (30 kD MWCO, Millipore). Concentration of samples was measured by NanoDrop (Thermo Scientific, Molar Absorbance=1.553). The purity of samples was estimated by SEC-UPLC at 215 nm, with the range between 75% and 99%.

Measurement of Binding Kinetics by SPR

The binding affinity to recombinant human sc-uPA protein (SEQ ID NO:1) was measured by surface plasmon resonance (SPR).

The experiments were performed on a Biacore™ instrument (GE Healthcare) and analysed with the BIAcore 4000 Evaluation Software. Anti-human uPA mAb variants were directly immobilized at 150-600 RU on flow cells of a CM5 sensor chip (GE Healthcare; cat. # BR-1000-12) via amine coupling, respectively. Recombinant human sc-uPA was diluted in HBS-N (GE Healthcare Cat BR-1006-70) with 1% BSA buffer with a dilution factor 3× ranging 1000-0.13 nM. Recombinant human sc-uPA was injected for 60 s, followed by a 600 s dissociation phase. Binding curves were measured at 25° C. with a flow rate of 30 µL/min. Regeneration of the chip surface was performed with pH1.5 Glycine for 25 s at 30 µl/min. Determination of the kinetic parameters was performed by fitting with a 1:1 binding model. Binding affinities were calculated and are stated in Table 17 below.

TABLE 17

Binding affinity of different rec0266-0000-0010 mutants

| Mutant | Biacore KD (M) |
|---|---|
| rec0266-0000-0010 | 4.7E−10 |
| rec0266-0000-0010-VH_D95A | 2.6E−09 |
| rec0266-0000-0010-VH_D95E | 2.0E−09 |
| rec0266-0000-0010-VH_D95F | 1.2E−08 |
| rec0266-0000-0010-VH_D95G | 1.2E−08 |
| rec0266-0000-0010-VH_D95H | 6.5E−09 |
| rec0266-0000-0010-VH_D95I | 1.4E−09 |
| rec0266-0000-0010-VH_D95K | 1.2E−08 |
| rec0266-0000-0010-VH_D95L | 4.7E−09 |
| rec0266-0000-0010-VH_D95P | 2.7E−09 |
| rec0266-0000-0010-VH_D95R | 1.3E−09 |
| rec0266-0000-0010-VH_D95S | 4.0E−09 |
| rec0266-0000-0010-VH_D95T | 1.5E−09 |
| rec0266-0000-0010-VH_D95V | 8.0E−10 |
| rec0266-0000-0010-VH_D95Y | 5.0E−09 |
| rec0266-0000-0010-VH_G96A | 1.5E−09 |
| rec0266-0000-0010-VH_G96E | 2.3E−09 |
| rec0266-0000-0010-VH_G96F | 7.2E−09 |
| rec0266-0000-0010-VH_G96H | 5.8E−09 |
| rec0266-0000-0010-VH_G96I | 1.8E−09 |
| rec0266-0000-0010-VH_G96K | 9.5E−10 |
| rec0266-0000-0010-VH_G96L | 1.9E−09 |
| rec0266-0000-0010-VH_G96N | 2.1E−08 |
| rec0266-0000-0010-VH_G96P | 2.1E−09 |
| rec0266-0000-0010-VH_G96R | 3.0E−09 |
| rec0266-0000-0010-VH_G96S | 1.3E−09 |
| rec0266-0000-0010-VH_G96T | 3.0E−09 |
| rec0266-0000-0010-VH_G96V | 2.1E−09 |
| rec0266-0000-0010-VH_G96Y | 1.3E−08 |
| rec0266-0000-0010-VH_D98A | 9.5E−10 |
| rec0266-0000-0010-VH_D98E | 4.9E−09 |
| rec0266-0000-0010-VH_D98F | 1.5E−09 |
| rec0266-0000-0010-VH_D98G | 2.4E−09 |
| rec0266-0000-0010-VH_D98H | 1.7E−09 |
| rec0266-0000-0010-VH_D98I | 2.0E−09 |
| rec0266-0000-0010-VH_D98K | 2.0E−09 |
| rec0266-0000-0010-VH_D98L | 2.0E−09 |
| rec0266-0000-0010-VH_D98P | 9.8E−10 |
| rec0266-0000-0010-VH_D98R | 1.1E−09 |
| rec0266-0000-0010-VH_D98S | 1.4E−08 |
| rec0266-0000-0010-VH_D98T | 2.2E−09 |
| rec0266-0000-0010-VH_D98V | 2.1E−09 |
| rec0266-0000-0010-VH_D98Y | 1.8E−09 |
| rec0266-0000-0010-VH_G99A | 2.4E−09 |
| rec0266-0000-0010-VH_G99E | 1.4E−09 |
| rec0266-0000-0010-VH_G99F | 1.7E−09 |
| rec0266-0000-0010-VH_G99H | 2.7E−08 |
| rec0266-0000-0010-VH_G99I | 4.6E−09 |
| rec0266-0000-0010-VH_G99K | 4.8E−09 |
| rec0266-0000-0010-VH_G99L | 2.1E−09 |
| rec0266-0000-0010-VH_G99N | 1.8E−08 |

TABLE 17-continued

Binding affinity of different rec0266-0000-0010 mutants

| Mutant | Biacore KD (M) |
| --- | --- |
| rec0266-0000-0010-VH_G99P | 2.5E−09 |
| rec0266-0000-0010-VH_G99R | 1.5E−08 |
| rec0266-0000-0010-VH_G99S | 4.1E−10 |
| rec0266-0000-0010-VH_G99T | 5.4E−09 |
| rec0266-0000-0010-VH_G99V | 2.5E−09 |
| rec0266-0000-0010-VH_G99Y | 1.8E−09 |

The results show that the potential iso-asp site "D95G96" can be removed without loss of affinity by rec0266-0000-0010-VH_D95V and rec0266-0000-0010-VH_G96K; and the potential iso-asp site "D98G99" can be removed without loss of affinity by rec0266-0000-0010-VH_G99S. Both rec0266-0000-0010-VH_D95V and rec0266-0000-0010-VH_G99S are demonstrated to retain the inhibitory effect on plasminogen activation induced by human uPA in the coupled zymogen activation assay.

Example 19: Removal of Anti-Human uPA Potential Deamidation Site on Light Chain To test the possibility for removal of the potential deamidation site "N90S91" in the light chain of rec0266-0000-0010 (marked with bold fonts), the single-mutation variants were produced and their binding affinities to human sc-uPA were measured by Biacore.

TABLE 18

Potential deamidation site on rec0266-0000-0010 light chain (SEQ ID NO: 20)

SEQ ID NO: 20 with potential deamidation site marked with bold fonts

Divmtqspatlsvtpgdryslscrtsqsigdylhwyqqkshesprllik
yvsqsisgipsrfsgsgsgsdftlsinsvesedvgvyyconshsfpltf
gsgtklelkrtvaaptvsifposseqltsggasvvcflnnfypkdinvk
wkidgsemngvlnswtdodskdstysmsstltltkdeyerhnsytceat
hktstspivksfnrnec Generation of Single Mutation Variants The mutation was introduced by site-directed mutagenesis with QuikChange II XL Site-Directed Mutagenesis Kit (Agilent Technologies, Cat. #200521), the codon exchange for each mutation is listed as below.

TABLE 19

Mutation codon exchange

| Mutation | From | To |
| --- | --- | --- |
| N90A | AAC | GCC |
| N90R | AAC | AGA |
| N90Q | AAC | CAA |
| N90E | AAC | GAA |
| N90G | AAC | GGC |
| N90H | AAC | CAT |
| N90I | AAC | ATC |
| N90L | AAC | CTG |
| N90K | AAC | AAA |
| N90F | AAC | TTT |
| N90P | AAC | CCC |
| N90S | AAC | AGC |
| N90T | AAC | ACC |
| N90Y | AAC | TAT |
| N90V | AAC | GTG |
| S91A | AGC | GCC |

TABLE 19-continued

Mutation codon exchange

| Mutation | From | To |
| --- | --- | --- |
| S91R | AGC | AGA |
| S91D | AGC | GAT |
| S91Q | AGC | CAA |
| S91E | AGC | GAA |
| S91H | AGC | CAT |
| S91I | AGC | ATC |
| S91L | AGC | CTG |
| S91K | AGC | AAA |
| S91F | AGC | TTT |
| S91P | AGC | CCC |
| S91T | AGC | ACC |
| S91Y | AGC | TAT |
| S91V | AGC | GTG |

Mutant Variants Expression and Purification

Plasmid DNA encoding light chain harbouring single mutation were co-transfected with that of wild-type heavy chain into Freestyle™ 293-F cells (Life Technologies, Cat. # R79007) with amount ratio of 1:1, by using 293Fectin™ reagent (Invitrogen, cat. #12347). Transfected cells were grown in serum-free FreeStyle 293 medium (Gibco, cat. #12338) containing 4 mM glutamine (Life Technologies, Cat. #25030-024), 1% PLURONIC® F68 (Gibco, Cat. #24040-032) and penicillin-streptomycin antibiotics (Life Technologies, Cat. # 10378016) at $1 \times 10^6$ cells per ml and incubated with shaking for 5 days at 37° C., 8% $CO_2$. Supernatants were collected on day 5 post transfection and clarified by centrifugation.

DNA Transfection:

The cell density of cultures used for transfection was 0.9-2.0×10⁶ cells/ml.

A mix of 0.5 μg light chain (LC) vector DNA and 0.5 μg heavy chain (HC) vector DNA was used per ml cell culture.

The DNA was diluted in Opti-MEM media (Gibco) to 30 μl media/μg DNA, mixed and incubated at room temperature (23-25° C.) for 5 min.

293Fectin™ (Invitrogen) was used as transfection reagent at a concentration of 1 μl per μg DNA.

The 293Fectin™ was diluted 30× in Opti-MEM media (Gibco), mixed and incubated at room temperature (23-25° C.) for 5 min.

The DNA and 293Fectin solutions were mixed and left to incubate at room temperature (23-25° C.) for 25 min.

The DNA-293Fectin mix was then added directly to the cell culture.

The transfected cell culture was transferred to a shaker incubator at 37° C., 8% $CO_2$ and 125 rpm.

5 days post transfection, cell culture supernatants were harvested by centrifugation, followed by filtration through a 0.22 μm PES filter (Corning).

Protein Purification:

Culture supernatant was harvested by centrifugation (15,000 rpm×20 min, 4° C.) and then cleared by the filtration with 0.45 μm cellulose nitrate membrane. The cleared supernatant was applied to 50 μl PreDictor MabSelect SuRe, 96-well filter plate (GE 28-9258-25). The bound mAb was then eluted with 20 mM formic acid and 100 mM arginine pH3.5, and buffer-exchanged to Phosphate Buffered Saline (PBS) with Amicon ultra 15 centrifugal units (30 kD MWCO, Millipore). Concentration of samples was measured by NanoDrop (Thermo Scientific, Molar Absorbance=1.553). The purity of samples was estimated by SEC-UPLC at 215 nm, with the range between 75% and 99%.

Measurement of Binding Kinetics by SPR

The binding affinity to recombinant human sc-uPA protein (SEQ ID NO:27) was measured by surface plasmon resonance (SPR).

The experiments were performed on a Biacore™ instrument (GE Healthcare) and analysed with the BIAcore 4000 Evaluation Software. Anti-human uPA mAb variants were directly immobilized at 150-600 RU on flow cells of a CM5 sensor chip (GE Healthcare; cat. # BR-1000-12) via amine coupling, respectively. Recombinant human sc-uPA was diluted in HBS-N (GE Healthcare Cat BR-1006-70) with 1% BSA buffer with a dilution factor 3× ranging 1000-0.13 nM. Recombinant human sc-uPA was injected for 60 s, followed by a 600 s dissociation phase. Binding curves were measured at 25° C. with a flow rate of 30 µL/min. Regeneration of the chip surface was performed with pH1.5 Glycine for 25 s at 30 µl/min. Determination of the kinetic parameters was performed by fitting with a 1:1 binding model. Binding affinities were calculated and are stated in Table 20 below.

TABLE 20

Binding affinity of different rec0266-0000-0010 mutants

| Mutant | Biacore KD (M) |
| --- | --- |
| rec0266-0000-0010 | 4.7E−10 |
| rec0266-0000-0010-VL_N90E | 4.3E−10 |
| rec0266-0000-0010-VL_N90F | 7.9E−10 |
| rec0266-0000-0010-VL_N90G | 6.8E−10 |
| rec0266-0000-0010-VL_N90H | 4.0E−10 |
| rec0266-0000-0010-VL_N90I | 6.2E−10 |
| rec0266-0000-0010-VL_N90K | 1.1E−09 |
| rec0266-0000-0010-VL_N90L | 6.1E−10 |
| rec0266-0000-0010-VL_N90P | 6.2E−10 |
| rec0266-0000-0010-VL_N90Q | 3.2E−10 |
| rec0266-0000-0010-VL_N90R | 1.9E−09 |
| rec0266-0000-0010-VL_N90S | 3.8E−10 |
| rec0266-0000-0010-VL_N90T | 4.8E−10 |
| rec0266-0000-0010-VL_N90V | 5.8E−10 |
| rec0266-0000-0010-VL_N90Y | 8.0E−10 |
| rec0266-0000-0010-VL_S91A | 1.3E−09 |
| rec0266-0000-0010-VL_S91D | 2.1E−09 |
| rec0266-0000-0010-VL_S91E | 1.0E−08 |
| rec0266-0000-0010-VL_S91F | 1.1E−08 |
| rec0266-0000-0010-VL_S91H | 5.3E−09 |
| rec0266-0000-0010-VL_S91I | 2.9E−09 |
| rec0266-0000-0010-VL_S91K | 3.2E−09 |
| rec0266-0000-0010-VL_S91L | 5.7E−09 |
| rec0266-0000-0010-VL_S91P | 2.0E−09 |
| rec0266-0000-0010-VL_S91Q | 2.2E−09 |
| rec0266-0000-0010-VL_S91R | 3.1E−09 |
| rec0266-0000-0010-VL_S91T | 8.8E−10 |
| rec0266-0000-0010-VL_S91V | 1.2E−08 |
| rec0266-0000-0010-VL_S91Y | 3.6E−09 |

The conclusion is that the potential deamidation site "N90S91" can be removed without loss of affinity to recombinant human sc-uPA by rec0266-0000-0010-VL_N90E, rec0266-0000-0010-VL_N90H, rec0266-0000-0010-VL_N90Q, rec0266-0000-0010-VL_N90S and rec0266-0000-0010-VL_N90T.

Example 20. Epitope Mapping by HDX-MS of mAb 0266-0000-0043 to Human uPA (SEQ ID NO: 1)

Introduction to HDX-MS

The HDX-MS technology exploits that hydrogen exchange (HDX) of a protein can readily be followed by mass spectrometry (MS). By replacing the aqueous solvent containing hydrogen with aqueous solvent containing deuterium, the incorporation of a deuterium atom at a given site in a protein will give rise to an increase in mass of 1 Da. This mass increase can be monitored as a function of time by mass spectrometrical analysis of quenched samples from the exchange reaction. The deuterium labelling information can be localized to specific regions of the protein by pepsin digestion under quenched conditions by following the mass increase of the resulting peptides.

One use of HDX-MS is to probe for sites involved in molecular interactions by identifying regions of reduced hydrogen exchange upon protein-protein complex formation. Usually, binding interfaces will be revealed by marked reductions in hydrogen exchange rates due to steric exclusion of solvent. Binding interfaces are typically revealed by reductions in hydrogen exchange observed during short incubations times (10 sec.-40 sec.). The reduction in hydrogen exchange within the binding interface is often found to level-off when longer incubation times are employed. Another use of HDX-MS is to assign allosteric changes within a molecule, which are characterized by no changes in hydrogen exchange level for short incubation times, (i.e., 10 sec.-20 sec.), while a reduction in hydrogen exchange is observed after long incubation times (40 s and longer). Protein-protein complex formation and allosteric changes induced by complex formation can be detected by HDX-MS simply by measuring the total amount of deuterium incorporated in either protein members in the presence and absence of the respective binding partner as a function of time. The HDX-MS technique uses the native components, i.e. target protein and antibody/Fab fragment, and is performed in solution (for a recent review on the HDX-MS technology, see Wales and Engen, Mass Spectrom. Rev. 25, 158 (2006)).

Materials and Methods

The protein batches used were human uPA (huPA): human recombinant sc-uPA (SEQ ID NO: 1) and mAb 0266-0000-0043 (SEQ ID NO: 21 and 22). All proteins were buffer exchanged into PBS pH 7.4 before experiments.

The HDX experiments were performed on a nanoACQUITY UPLC System with HDX Technology (Waters Inc.) coupled to a Synapt G2 mass spectrometer (Waters Inc.). The Waters HDX system contained a Leap robot (H/D-x PAL; Waters Inc.) operated by the LeapShell software (Leap Technologies Inc/Waters Inc.), which performed initiation of the deuterium exchange reaction, reaction time control, quench reaction, injection onto the UPLC system and digestion time control. The Leap robot was equipped with two temperature controlled stacks maintained at 20° C. for buffer storage and HDX reactions and maintained at 2° C. for storage of protein and quench solution, respectively. The Waters HDX system furthermore contained a temperature controlled chamber holding the pre- and analytical columns, and the LC tubing and switching valves at 1° C. A temperature controlled chamber held the pepsin column at 25° C. For the inline pepsin digestion, 100 µL quenched sample containing 300 pmol human uPA was loaded and passed over a Poroszyme® Immobilized Pepsin Cartridge (2.1×30 mm (Applied Biosystems)) placed at 25° C. using a isocratic flow rate of 100 µL/min (0.1% formic acid:CH$_3$CN 95:5). The resulting peptides were trapped and desalted on a VanGuard pre-column BEH C18 1.7 µm (2.1×5 mm (Waters Inc.)). Subsequently, the valves were switched to place the pre-column inline with the analytical column, UPLC-BEH C18 1.7 µm (1×100 mm (Waters Inc.)), and the peptides separated using a 9 min gradient of 10-50% B delivered at 40 µl/min from the nanoAQUITY UPLC system (Waters Inc.). The mobile phases consisted of A: 0.1% formic acid and B: 0.1% formic acid in CH$_3$CN. The ESI MS data, and the separate elevated energy (MS$^E$) experiments were acquired in positive ion mode using a Synapt G2 mass spectrometer (Waters Inc.). Leucine-enkephalin was used as the lock mass ([M+H]$^+$ ion at m/z 556.2771) and data was collected in continuum mode (For further description, see Andersen and Faber, Int. J. Mass Spec., 302, 139-148 (2011)).

Data Analysis

Peptic peptides were identified in separate experiments using standard MS$^E$ methods where the peptides and fragments are further aligned utilizing the ion mobility properties of the Synapt G2 (Waters Inc.). MS$^E$ data were processed using Protein Lynx Global Server version 2.5 (Waters Inc.). The HDX-MS raw data files were processed in the DynamX 2.0 software (Waters Inc.). DynamX automatically performs the lock mass-correction and deuterium incorporation determination, i.e., centroid determination of deuterated peptides. Furthermore, all peptides were inspected manually to ensure correct peak and deuteration assignment by the software.

Epitope Mapping Experiment

Amide hydrogen/deuterium exchange (HDX) was initiated by a 16-fold dilution of huPA in the presence or absence of mAb 0266-0000-0043 into the corresponding deuterated buffer (i.e. PBS prepared in D$_2$O, 96% D$_2$O final, pH 7.4 (uncorrected value)). All HDX reactions were carried out at 20° C. and contained 4 µM huPA in the absence or presence of 2.4 µM mAb, thus giving a 1.2 fold molar excess of mAb binding sites. At appropriate time intervals ranging from 10 sec to 480 sec, 50 µl aliquots of the HDX reaction were quenched by addition of 50 µl ice-cold quenching buffer (1.35 M Tris(2-carboxyethyl)phosphine) resulting in a final pH of 2.5 (uncorrected value).

Results and Discussion

The HDX-MS time-course of 163 peptides, covering 93% of the primary sequence of huPA was monitored in the absence or presence of the anti-uPA for 10, 20, 40, 60, 120, 240, and 480 sec.

The obtained data allowed the epitope binding site of anti-uPA to huPA to be assigned to two linear sequences covering residues 167-175 and 218-224, respectively. This is shown in Table 22, that demonstrates the identification of epitope by HDX-MS analysis of Anti-uPA (mAb 0266-0000-0043) to human uPA (SEQ ID NO: 1). After deuterium exchange reaction huPA is digested with pepsin yielding the present peptic peptides identified to show HDX protection in the presence of Anti-uPA at short incubation times at least 10 sec, 20 sec and 40 sec. Peptic peptides that were identified to show unaffected exchange in the presence of Anti-uPA and contributed to the assigned allosteric regions are likewise present.

Furthermore, the HDX-MS study reveal an extended network of allosterically coupled sites, which displayed lowered deuterium incorporation upon binding to anti-uPA covering the residues 1-33, 67-80, 187-215, 225-234, 243-256, 260-274, 291-306, 322-341, 375-389, and 397-410. This is shown in Table 21, allosteric regions identified by HDX-MS analysis of Anti-uPA (mAb 0266-0000-0043) to human uPA (SEQ ID NO: 1). After deuterium exchange reaction, huPA is digested with pepsin yielding the present peptic peptides identified to show hydrogen to deuterium exchange (HDX) protection in the presence of Anti-uPA at incubation times longer than 40 sec. Peptic peptides that were identified to show unaffected HDX in the presence of Anti uPA and contributed to the assigned allosteric regions are likewise present.

The alteration of deuterium incorporation is only observed as lowered upon binding to anti-uPA. Thus the data incorporate an allosteric population shift from the flexible unliganded ensemble to a more rigid anti-uPA bound ensemble.

Furthermore, HDX-MS enabled the assignment of the epitope binding site of anti-uPA (mAb 0266-0000-0043) to huPA (SEQ ID NO: 1) to two linear sequences covering residues 167-175 and 218-224. Hints of an allosteric population shift from the flexible unliganded ensemble to a more rigid anti-uPA bound ensemble was afforded by lowered deuterium incorporation upon binding to anti-uPA covering the residues 1-33, 67-80, 187-215, 225-234, 243-256, 260-274, 291-300, 320-341, 375-389, and 402-410.

TABLE 21

Allosteric regions identified by HDX-MS analysis of Anti-uPA (mAb 0266-0000-0043) to human uPA (SEQ ID NO: 1)

| Start | End | Sequence | Deuterium profile* |
|---|---|---|---|
| 1 | 12 | SNELHQVPSNCD | A-EX |
| 1 | 13 | SNELHQVPSNCDC | A-EX |
| 12 | 24 | DCLNGGTCVSNKY | A-EX |
| 13 | 24 | CLNGGTCVSNKY | A-EX |
| 16 | 31 | GGTCVSNKYFSNIHWC | A-EX |
| 18 | 32 | TCVSNKYFSNIHWCN | A-EX |
| 25 | 33 | FSNIHWCNC | A-EX |
| 65 | 77 | DTMGRPCLPWNSA | A-EX |
| 65 | 80 | DTMGRPCLPWNSATVL | A-EX |
| 67 | 77 | MGRPCLPWNSA | A-EX |
| 67 | 80 | MGRPCLPWNSATVL | A-EX |
| 71 | 86 | CLPWNSATVLQQTYHA | A-EX |
| 78 | 93 | TVLQQTYHAHRSDALQ | A-EX |
| 79 | 93 | VLQQTYHAHRSDALQ | A-EX |
| 187 | 193 | YVCGGSL | A-EX |
| 194 | 205 | SPCWVISATHC | A-EX |
| 194 | 206 | SPCWVISATHCF | A-EX |
| 199 | 205 | ISATHC | A-EX |
| 206 | 215 | FIDYPKKEDY | A-EX |
| 225 | 234 | NSNTQGEMKF | A-EX |
| 229 | 240 | QGEMKFEVENLI | A-EX |
| 235 | 241 | EVENLIL | N |
| 243 | 256 | KDYSADTLAHHNDI | A-EX |
| 260 | 274 | KIRSKEGRCAQPSRT | A-EX |
| 261 | 274 | IRSKEGRCAQPSRT | A-EX |
| 275 | 290 | IQTICLPSMYNDPQFG | N |

TABLE 21-continued

Allosteric regions identified by HDX-MS analysis of Anti-uPA (mAb 0266-0000-0043) to human uPA (SEQ ID NO: 1)

| Start | End | Sequence | Deuterium profile* |
|---|---|---|---|
| 277 | 283 | TICLPSM | N |
| 291 | 306 | TSCEITGFGKENSTDY | A-EX |
| 301 | 315 | ENSTDYLYPEQLKMT | N |
| 320 | 330 | ISHRECQQPHY | A-EX |
| 320 | 334 | ISHRECQQPHYYGSE | A-EX |
| 322 | 334 | HRECQQPHYYGSE | A-EX |
| 335 | 341 | VTTKMLC | A-EX |
| 375 | 382 | SWGRGCAL | A-EX |
| 375 | 389 | SWGRGCALKDKPGVY | A-EX |
| 380 | 389 | CALKDKPGVY | A-EX |
| 390 | 401 | TRVSHFLPWIRS | A-EX |
| 397 | 410 | PWIRSHTKEENGLA | A-EX |
| 400 | 408 | RSHTKEENG | A-EX |

A-EX: HDX protection upon antibody binding indicating allosteric region (>2 SD.) on at least three time-points at incubation 40s and longer.
N: No HDX protection upon antibody binding (>2 SD.).

TABLE 22

Epitope identified by HDX-MS analysis of Anti-uPA (mAb 0266-0000-0043) to human uPA (SEQ ID NO: 1)

| Start | End | Sequence | Deuterium level* |
|---|---|---|---|
| 157 | 164 | FKIIGGEF | E-EX |
| 158 | 164 | KIIGGEF | E-EX |
| 165 | 173 | TTIENQPWF | E-EX |
| 165 | 175 | TTIENQPWFAA | E-EX |
| 177 | 186 | YRRHRGGSVT | N |
| 216 | 224 | IVYLGRSRL | E-EX |
| 217 | 223 | VYLGRSR | E-EX |
| 217 | 224 | VYLGRSRL | E-EX |

Example 21. Mode of Action of mAb 0266-0000-0043

Four segments have been defined as involved in significant conformation changes upon activation of serine proteases (Freer et al., 1970, Biochemistry 9, 1997-2009; Huber & Bode 1978, Acc Chem Res 11, 114-122; Jiang et al., 2013, Biochem J 449, 161-166). The activation loop (16-21 bovine chymotrypsinogen; 159-164 human sc-uPA), which is repositioned after cleavage of the Lys158-Ile159 peptide bond resulting in the formation of an internal ion pair between the α-amino group of Ile159 and the buried side-chain carboxyl group of Asp355.

The autolysis loop (142-154 bovine chymotrypsinogen; 299-311 human sc-uPA) that stabilizes the activation loop in the active enzyme by direct interactions from Phe298 and Gly299 to Ile159. The oxyanion-stabilizing loop (184-194 bovine chymotrypsinogen; 343-355 human sc-uPA) forms a pocket of backbone mediated positive charge in the active enzyme that activates the carbonyl of the scissile peptide bond and stabilizes the negatively charged oxyanion of the tetrahedral intermediate. Finally, and the S1 entrance frame (216-223 bovine chymotrypsinogen; 377-384 human sc-uPA) forms the S1 pocket that determines the specificity of the protease and interacts with the peptide substrate to promote substrate hydrolysis.

While mAb-112 inhibits human uPA activity by interaction with the autolysis loop leading to displacement of the N-terminus from the activation pocket (Jiang et al., 2013, Biochem J 449, 161-166) and mouse mU1 cannot inhibit human uPA but only mouse uPA by interaction with residues corresponding to human sc-uPA amino acid residues Gly183, Val185 (Pro in mouse uPA), Thr186 (Pro in mouse uPA), Arg223 (Lys in mouse uPA), Asn225 (Ser in mouse uPA), Asn227 (Tyr in mouse uPA), Thr228 (Asn in mouse uPA), Gln229 (Pro in mouse uPA) leading to allosteric inhibition of autolysis loop docking and S1 pocket and oxyanion hole distortion (Kromann-Hansen et al., 2013, Biochemistry 52, 7114-7126); mAb 0266-0000-0043 is unique by inhibiting human uPA through an epitope covering Ile167-Ala175 and Tyr218-Leu224 that induces a synergistic change in the conformation of the 1-33, 67-80, 187-215, 230-234, 243-256, 260-274, 291-306, 322-341, 375-389 and 397-410 areas, which involves but is not limited to the reorganisation of the autolysis loop and the S1 entrance frame and concomitant allosteric inhibition of uPA activation and activity. The extensive network of conformational changes induced through the Ile167-Ala175 and Tyr218-Leu224 epitope implies that equivalent conformational changes can be induced by mAb targeting of any of the allosterically affected sites.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An antibody or antigen-binding fragment thereof that is capable of binding to human uPA, wherein the heavy chain of said antibody comprises:
   a CDR1 sequence of amino acid residues 31 (Kabat and sequential) to 35 (Kabat and sequential) (SYTMS) of SEQ ID NO: 7; and
   a CDR2 sequence of amino acids 50 (Kabat and sequential) to 65 (Kabat; 66 sequential) (TISGGGSHIYY-ADSVKG) of SEQ ID NO: 7; and
   a CDR3 sequence of amino acid residues 95 (Kabat; 99 sequential) to 102 (Kabat; 108 sequential) (DGRDG-SWFAY) of SEQ ID NO: 7 and wherein the light chain of said antibody comprises:
   a CDR1 sequence of amino acid residues 24 (Kabat and sequential) to 34 (Kabat and sequential) (RTSQSIGDYLH) of SEQ ID NO: 8; and
   a CDR2 sequence of amino acid residues 50 (Kabat and sequential) to 56 (Kabat and sequential) (YVSQSIS) of SEQ ID NO: 8; and
   a CDR3 sequence of amino acid residues 89 (Kabat and sequential) to 97 (Kabat and sequential) (QNSHSF-PLT) of SEQ ID NO: 8.

2. An antibody or antigen-binding fragment thereof that is capable of binding to human uPA, wherein the antibody is humanized and wherein the heavy chain comprises:
   a CDR-H1 comprising SEQ ID NO: 9, located in amino acid residues 31-35 (Kabat); and
   a CDR-H2 comprising SEQ ID NO: 10, located in amino acid residues 50-65 (Kabat); and
   a CDR-H3 comprising SEQ ID NO: 11, located in amino acid residues 95-102 (Kabat)
   and wherein the light chain comprises:
   a CDR-L1 comprising SEQ ID NO: 12, located in amino acid residues 24-34 (Kabat); and
   a CDR-L2 comprising SEQ ID NO: 13, located in amino acid residues 50-56 (Kabat); and
   a CDR-L3 comprising SEQ ID NO: 14, located in amino acid residues 89-97 (Kabat).

3. An antibody or antigen-binding fragment thereof that is capable of binding to human uPA wherein said antibody comprises a heavy chain comprising SEQ ID NO: 21 and a light chain comprising SEQ ID NO:22.

* * * * *